(12) United States Patent
Posada et al.

(10) Patent No.: US 12,077,790 B2
(45) Date of Patent: Sep. 3, 2024

(54) OPTIMIZED BINUCLEASE FUSIONS AND METHODS

(71) Applicant: Resolve Therapeutics, LLC, St. Petersburg, FL (US)

(72) Inventors: James Arthur Posada, St. Petersburg, FL (US); Sanjay Patel, San Diego, CA (US); Weihong Yu, San Diego, CA (US); Chris Gabel, Seattle, WA (US)

(73) Assignee: Resolve Therapeutics, LLC, Miami, FL (US)

( * ) Notice: Subject to any disclaimer, the term of this patent is extended or adjusted under 35 U.S.C. 154(b) by 140 days.

(21) Appl. No.: 17/560,522

(22) Filed: Dec. 23, 2021

(65) Prior Publication Data

US 2022/0112474 A1 Apr. 14, 2022

Related U.S. Application Data

(63) Continuation of application No. 16/313,656, filed as application No. PCT/US2017/040267 on Jun. 30, 2017, now abandoned.

(60) Provisional application No. 62/357,756, filed on Jul. 1, 2016.

(51) Int. Cl.
  *C12N 9/22* (2006.01)
  *A61K 38/00* (2006.01)

(52) U.S. Cl.
  CPC ........ *C12N 9/22* (2013.01); *C12Y 301/21001* (2013.01); *C12Y 301/27005* (2013.01); *A61K 38/00* (2013.01); *C07K 2317/72* (2013.01); *C07K 2319/30* (2013.01)

(58) Field of Classification Search
  None
  See application file for complete search history.

(56) References Cited

U.S. PATENT DOCUMENTS

| | | |
|---|---|---|
| 3,773,919 A | 11/1973 | Boswell et al. |
| 3,941,763 A | 3/1976 | Sarantakis |
| 4,179,337 A | 12/1979 | Davis et al. |
| 4,301,144 A | 11/1981 | Iwashita et al. |
| 4,496,689 A | 1/1985 | Mitra |
| 4,640,835 A | 2/1987 | Shimizu et al. |
| 4,670,417 A | 6/1987 | Iwasaki et al. |
| 4,683,202 A | 6/1987 | Mullis |
| 4,683,195 A | 7/1987 | Mullis et al. |
| 4,791,192 A | 12/1988 | Nakagawa et al. |
| 4,800,159 A | 1/1989 | Mullis et al. |
| 4,965,188 A | 10/1990 | Mullis et al. |
| 4,973,556 A | 11/1990 | Bove et al. |
| 5,423,269 A | 6/1995 | Saxton et al. |
| 5,428,130 A | 6/1995 | Capon et al. |
| 5,453,269 A | 9/1995 | Haber et al. |
| 5,525,491 A | 6/1996 | Huston et al. |
| 5,559,212 A | 9/1996 | Ardelt |
| 5,624,821 A | 4/1997 | Winter et al. |
| 5,637,481 A | 6/1997 | Ledbetter et al. |
| 5,648,260 A | 6/1997 | Winter et al. |
| 5,643,749 A | 7/1997 | Revel et al. |
| 5,658,570 A | 8/1997 | Newman et al. |
| 5,821,333 A | 1/1998 | Carter et al. |
| 5,731,168 A | 3/1998 | Carter et al. |
| 5,731,169 A | 3/1998 | Mogensen et al. |
| 5,739,277 A | 4/1998 | Presta et al. |
| 5,780,027 A | 7/1998 | Maroun |
| 5,807,706 A | 9/1998 | Carter et al. |
| 5,827,516 A | 10/1998 | Urban et al. |
| 5,834,250 A | 11/1998 | Wells et al. |
| 5,840,296 A | 11/1998 | Raines et al. |
| 5,840,840 A | 11/1998 | Rybak et al. |
| 5,869,046 A | 2/1999 | Presta et al. |
| 5,876,969 A | 3/1999 | Fleer et al. |
| 5,932,462 A | 8/1999 | Harris et al. |
| 5,955,073 A | 9/1999 | Rybak et al. |
| 5,973,116 A | 10/1999 | Epenetos et al. |
| 5,989,830 A | 11/1999 | Davis et al. |
| 5,994,514 A | 11/1999 | Jardieu et al. |
| 6,096,871 A | 8/2000 | Presta et al. |
| 6,121,022 A | 9/2000 | Presta et al. |
| 6,175,003 B1 | 1/2001 | Saxena |
| 6,194,551 B1 | 2/2001 | Idusogie et al. |
| 6,239,257 B1 | 5/2001 | Ardelt |

(Continued)

FOREIGN PATENT DOCUMENTS

| | | |
|---|---|---|
| BR | 112012010202 | 9/2015 |
| CL | 2013-02438 A | 8/2014 |

(Continued)

OTHER PUBLICATIONS

Achord et al., "Human beta-Glucuronidase. II. Fate of Infused Human Placental beta- Glucuronidase in the Rat," Pediat. Res 1977;11: 816-822.

Achord et al., "Human beta-Glucuronidase: In Vivo Clearance and in Vitro Uptake by a Glycoprotein Recognition System on Reticuloendothelial Cells," Cell 1978; 15: 269-278.

Ahlin et al., "Autoantibodies associated with RNA are more enriched than anti-dsDNA antibodies in circulating immune complexes in SLE," Lupus 2012:21:586-595.

Aplin et al., "Preparation, Properties and Applications of Carbohydrate Conjugates of Proteins and Lipids," CRC Crit Rev Biochem 1981; 259-306.

Arai et al., "Design of the linkers which effectively separate domains of a bifunctional fusion protein," Protein Eng 2001;14: 529-532.

(Continued)

*Primary Examiner* — Phuong Huynh
(74) *Attorney, Agent, or Firm* — Foley Hoag LLP; Amy E. Mandragouras; Samantha N. Devenport

(57) ABSTRACT

The invention provides for optimized binuclease fusion proteins with increased pharmacokinetic properties. The optimized binuclease fusion proteins of the invention two or more nuclease domains (e.g., RNase and DNase domain) operably coupled to an Fc domain. The invention also provides methods of treating or preventing a condition associated with an abnormal immune response.

28 Claims, 3 Drawing Sheets

Specification includes a Sequence Listing.

(56) References Cited

U.S. PATENT DOCUMENTS

| | | |
|---|---|---|
| 6,242,195 B1 | 6/2001 | Idusogie et al. |
| 6,277,375 B1 | 8/2001 | Ward |
| 6,280,991 B1 | 8/2001 | Raines |
| 6,331,396 B1 | 12/2001 | Silverman et al. |
| 6,348,343 B2 | 2/2002 | Lazarus et al. |
| 6,372,207 B1 | 4/2002 | Tepper et al. |
| 6,391,607 B1 | 5/2002 | Lazarus et al. |
| 6,475,983 B1 | 11/2002 | Eid et al. |
| 6,482,626 B2 | 11/2002 | Baker et al. |
| 6,528,624 B1 | 3/2003 | Idusogie et al. |
| 6,538,124 B1 | 3/2003 | Idusogie et al. |
| 6,635,416 B2 | 10/2003 | Palese et al. |
| 6,653,104 B2 | 11/2003 | Goldenberg |
| 6,660,843 B1 | 12/2003 | Feige et al. |
| 6,716,974 B1 | 4/2004 | Maciag et al. |
| 6,737,056 B1 | 5/2004 | Presta |
| 6,787,634 B2 | 9/2004 | Benoit et al. |
| 6,821,505 B2 | 11/2004 | Ward |
| 6,998,253 B1 | 2/2006 | Presta et al. |
| 7,033,572 B2 | 4/2006 | Goldenberg |
| 7,067,298 B2 | 6/2006 | Latham et al. |
| 7,074,592 B2 | 7/2006 | Ashkenazi et al. |
| 7,083,784 B2 | 8/2006 | Dall'Acqua et al. |
| 7,087,726 B2 | 8/2006 | Chuntharapai et al. |
| 7,098,016 B2 | 8/2006 | Raines et al. |
| 7,118,751 B1 | 10/2006 | Ledbetter et al. |
| 7,176,278 B2 | 2/2007 | Prior |
| 7,247,302 B1 | 7/2007 | Rosok et al. |
| 7,317,091 B2 | 1/2008 | Lazar et al. |
| 7,364,731 B2 | 4/2008 | Idusogie et al. |
| 7,407,785 B2 | 8/2008 | Lazarus et al. |
| 7,416,875 B2 | 8/2008 | Raines et al. |
| 7,442,527 B2 | 10/2008 | Palese et al. |
| 7,544,487 B2 | 6/2009 | Goldenberg et al. |
| 7,608,395 B2 | 10/2009 | Pascual et al. |
| 7,642,228 B2 | 1/2010 | Carter et al. |
| 7,655,757 B2 | 2/2010 | Raines et al. |
| 7,662,925 B2 | 2/2010 | Lazar et al. |
| 7,695,936 B2 | 4/2010 | Carter et al. |
| 7,732,167 B2 | 6/2010 | Smith et al. |
| 7,749,735 B2 | 7/2010 | Schreiber |
| 7,754,208 B2 | 7/2010 | Ledbetter et al. |
| 7,754,209 B2 | 7/2010 | Ledbetter et al. |
| 7,807,409 B2 | 10/2010 | Kopetzki |
| 7,829,084 B2 | 11/2010 | Ledbetter et al. |
| 7,892,740 B2 | 2/2011 | Weichselbaum et al. |
| 7,910,707 B2 | 3/2011 | Chuntharapai et al. |
| 8,029,782 B2 | 10/2011 | Klink et al. |
| 8,067,548 B2 | 11/2011 | Wang et al. |
| 8,133,699 B2 | 3/2012 | Chatellard et al. |
| 8,158,579 B2 | 4/2012 | Ballance et al. |
| 8,198,063 B1 | 6/2012 | Baginski et al. |
| 8,216,805 B2 | 7/2012 | Carter et al. |
| 8,349,331 B2 | 1/2013 | Chuntharapai et al. |
| 8,586,713 B2 | 11/2013 | Davis et al. |
| 8,642,752 B2 | 2/2014 | Swayze et al. |
| 8,679,785 B2 | 3/2014 | Carter et al. |
| 8,697,065 B2 | 4/2014 | Strong et al. |
| 8,828,393 B2 | 9/2014 | Pickford et al. |
| 8,841,416 B2 * | 9/2014 | Ledbetter .................. A61P 7/06 424/193.1 |
| 8,871,912 B2 | 10/2014 | Davis et al. |
| 8,937,157 B2 * | 1/2015 | Ledbetter .................. A61P 5/14 424/193.1 |
| 9,150,663 B2 | 10/2015 | Labrijn et al. |
| 9,181,345 B2 | 11/2015 | Zmuda et al. |
| 9,249,226 B2 | 2/2016 | De Weers et al. |
| 9,493,570 B2 | 11/2016 | Higgs et al. |
| 9,499,634 B2 | 11/2016 | Dixit et al. |
| 9,505,848 B2 | 11/2016 | Davis et al. |
| 9,540,433 B2 | 1/2017 | Verploegen et al. |
| 9,562,109 B2 | 2/2017 | Von Kreudenstein et al. |
| 9,574,010 B2 | 2/2017 | Spreter Von Kreudenstein et al. |
| 9,636,420 B2 | 5/2017 | Song et al. |
| 9,790,479 B2 * | 10/2017 | Ledbetter ................ A61P 19/08 |
| 9,822,173 B2 | 11/2017 | Kannan et al. |
| 9,861,681 B2 | 1/2018 | Golden et al. |
| 9,895,433 B2 | 2/2018 | Portnoy et al. |
| 9,919,062 B2 | 3/2018 | Kirn |
| 10,000,745 B2 * | 6/2018 | Ledbetter ................ A61P 27/02 |
| 10,150,800 B2 | 12/2018 | Roschke et al. |
| 10,202,588 B2 | 2/2019 | Ledbetter et al. |
| 10,947,295 B2 | 3/2021 | Posada et al. |
| 10,988,745 B2 | 4/2021 | Posada et al. |
| 11,034,944 B2 * | 6/2021 | Ledbetter .................. A61P 3/10 |
| 11,306,295 B2 | 4/2022 | Hori et al. |
| 11,306,297 B2 * | 4/2022 | Ledbetter ................ A61P 19/08 |
| 2002/0103125 A1 | 8/2002 | Ashkenazi et al. |
| 2002/0160974 A1 | 10/2002 | Banchereau et al. |
| 2003/0108548 A1 | 6/2003 | Bluestone et al. |
| 2003/0175778 A1 | 9/2003 | Ni et al. |
| 2004/0132101 A1 | 7/2004 | Lazar et al. |
| 2004/0266993 A1 | 12/2004 | Evans |
| 2005/0013813 A1 | 1/2005 | Maroun |
| 2005/0054832 A1 | 3/2005 | Lazar et al. |
| 2005/0136049 A1 | 6/2005 | Ledbetter et al. |
| 2005/0158307 A1 | 7/2005 | Spies et al. |
| 2005/0175614 A1 | 8/2005 | Ledbetter et al. |
| 2005/0180970 A1 | 8/2005 | Ledbetter et al. |
| 2005/0186216 A1 | 8/2005 | Ledbetter et al. |
| 2005/0202012 A1 | 9/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0238646 A1 | 10/2005 | Ledbetter et al. |
| 2006/0040262 A1 | 2/2006 | Morris et al. |
| 2006/0235208 A1 | 10/2006 | Lazar et al. |
| 2006/0240419 A1 | 10/2006 | Nakamura et al. |
| 2006/0074225 A1 | 11/2006 | Clark et al. |
| 2006/0263774 A1 | 11/2006 | Clark et al. |
| 2007/0025982 A1 | 2/2007 | Ledbetter et al. |
| 2007/0059306 A1 | 3/2007 | Grosmaire et al. |
| 2007/0105127 A1 | 5/2007 | Gerngross |
| 2007/0111281 A1 | 5/2007 | Sondermann et al. |
| 2007/0178552 A1 | 8/2007 | Arathoon et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0237779 A1 | 10/2007 | Ledbetter et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0057056 A1 | 3/2008 | Lazar et al. |
| 2008/0181892 A1 | 7/2008 | Ledbetter et al. |
| 2008/0227958 A1 | 9/2008 | Thompson et al. |
| 2008/0242845 A1 | 10/2008 | Lazar et al. |
| 2008/0274958 A1 | 11/2008 | DeFrees |
| 2008/0279850 A1 | 11/2008 | Brady et al. |
| 2008/0293121 A1 | 11/2008 | Lazarus et al. |
| 2009/0148447 A1 | 6/2009 | Ledbetter et al. |
| 2009/0148462 A1 | 6/2009 | Chevrier et al. |
| 2009/0155286 A1 | 6/2009 | Gilliet et al. |
| 2009/0175867 A1 | 7/2009 | Thompson et al. |
| 2009/0182127 A1 | 7/2009 | Kjaergaard et al. |
| 2009/0196870 A1 | 8/2009 | Ledbetter et al. |
| 2009/0214539 A1 | 8/2009 | Grosmaire et al. |
| 2009/0252729 A1 | 10/2009 | Farrington et al. |
| 2009/0258005 A1 | 10/2009 | Gill et al. |
| 2009/0263474 A1 | 10/2009 | Banchereau et al. |
| 2009/0274692 A1 | 11/2009 | Tan et al. |
| 2010/0015661 A1 | 1/2010 | Dubel et al. |
| 2010/0034820 A1 | 2/2010 | Ledbetter et al. |
| 2010/0099101 A1 | 4/2010 | Behrens et al. |
| 2010/0104564 A1 | 4/2010 | Hansen et al. |
| 2010/0203052 A1 | 8/2010 | Ledbetter et al. |
| 2010/0254986 A1 | 10/2010 | Carter et al. |
| 2010/0273220 A1 | 10/2010 | Yanik et al. |
| 2010/0279932 A1 | 11/2010 | Ledbetter et al. |
| 2010/0330089 A1 | 12/2010 | Damle et al. |
| 2011/0033483 A1 | 2/2011 | Thompson et al. |
| 2011/0081345 A1 | 4/2011 | Moore et al. |
| 2011/0091461 A1 | 4/2011 | Ledbetter et al. |
| 2011/0105729 A1 | 5/2011 | Ledbetter et al. |

(56) References Cited

U.S. PATENT DOCUMENTS

| | | |
|---|---|---|
| 2011/0123440 A1 | 5/2011 | Hansen et al. |
| 2011/0151515 A1 | 6/2011 | Heifetz et al. |
| 2011/0154516 A1 | 6/2011 | Stafford et al. |
| 2011/0171208 A1 | 7/2011 | Tan et al. |
| 2011/0171218 A1 | 7/2011 | Seehra et al. |
| 2012/0010387 A1 | 1/2012 | Niwa et al. |
| 2012/0149876 A1 | 6/2012 | Von Kreudenstein et al. |
| 2012/0201746 A1 | 8/2012 | Liu et al. |
| 2012/0208278 A1 | 8/2012 | Yanik et al. |
| 2012/0225066 A1 | 9/2012 | Ledbetter et al. |
| 2013/0089546 A1 | 4/2013 | Ledbetter et al. |
| 2013/0177555 A1 | 7/2013 | Wilkinson et al. |
| 2013/0177561 A1 | 7/2013 | Ledbetter et al. |
| 2013/0183308 A1 | 7/2013 | Ledbetter et al. |
| 2013/0184334 A1 | 7/2013 | Ledbetter et al. |
| 2013/0209445 A1 | 8/2013 | Lazar et al. |
| 2013/0330345 A1 | 12/2013 | Igawa et al. |
| 2013/0336973 A1 | 12/2013 | Spreter Von Kreudenstein et al. |
| 2014/0044711 A1 | 2/2014 | Ledbetter et al. |
| 2014/0051835 A1 | 2/2014 | Dixit et al. |
| 2014/0154253 A1 | 6/2014 | Ng et al. |
| 2014/0154254 A1 | 6/2014 | Kannan et al. |
| 2014/0170148 A1 | 6/2014 | De Goeij et al. |
| 2014/0170149 A1 | 6/2014 | Neijssen et al. |
| 2014/0178379 A1 | 6/2014 | Ledbetter et al. |
| 2014/0178479 A1 | 6/2014 | Bakhru et al. |
| 2014/0227269 A1 | 8/2014 | Ledbetter et al. |
| 2014/0227300 A1 | 8/2014 | Chin et al. |
| 2014/0303356 A1 | 10/2014 | Gramer et al. |
| 2015/0037871 A1 | 2/2015 | Ledbetter et al. |
| 2015/0152399 A1 | 6/2015 | Ledbetter et al. |
| 2016/0046727 A1 | 2/2016 | Labrijn et al. |
| 2016/0051696 A1 | 2/2016 | Song et al. |
| 2016/0102135 A1 | 4/2016 | Escobar-Cabrera |
| 2017/0100488 A1 | 4/2017 | Park et al. |
| 2017/0158779 A1 | 6/2017 | Dixit et al. |
| 2017/0166650 A1 | 6/2017 | Niwa et al. |
| 2017/0173151 A1 | 6/2017 | Verploegen et al. |
| 2017/0233497 A1 | 8/2017 | Labrijn et al. |
| 2017/0257763 A1 | 9/2017 | Christian et al. |
| 2017/0313769 A1 | 11/2017 | Gulla et al. |
| 2017/0368169 A1 | 12/2017 | Loew et al. |
| 2017/0369590 A1 | 12/2017 | De Goeij et al. |
| 2017/0369594 A1 | 12/2017 | Neijssen et al. |
| 2018/0009908 A1 | 1/2018 | Aldaz et al. |
| 2018/0016347 A1 | 1/2018 | Spreter Von Kreudenstein et al. |
| 2018/0016354 A1 | 1/2018 | Wozniak-Knopp et al. |
| 2018/0057567 A1 | 3/2018 | Rao et al. |
| 2018/0080082 A1 | 3/2018 | Mougeot et al. |
| 2018/0187174 A1 | 7/2018 | Ledbetter et al. |
| 2019/0030024 A1 | 1/2019 | Wen et al. |
| 2019/0119660 A1 | 4/2019 | Ledbetter et al. |
| 2019/0194293 A1 | 6/2019 | Posada et al. |
| 2019/0241878 A1 | 8/2019 | Posada et al. |
| 2021/0155673 A1 | 5/2021 | Posada et al. |
| 2021/0395711 A1 | 12/2021 | Ledbetter et al. |
| 2022/0089786 A1 | 3/2022 | Posada et al. |
| 2023/0057085 A1 | 2/2023 | Ledbetter et al. |
| 2023/0355722 A1 | 11/2023 | Posada et al. |

FOREIGN PATENT DOCUMENTS

| | | |
|---|---|---|
| CL | 201302438 | 8/2014 |
| CN | 1852976 A | 10/2006 |
| CN | 101990439 A | 3/2011 |
| CN | 102770533 A | 11/2012 |
| CN | 103930127 | 7/2014 |
| DE | 102005009219 | 8/2006 |
| EP | 0036676 A1 | 9/1981 |
| EP | 0058481 A1 | 8/1982 |
| EP | 0088046 A2 | 9/1983 |
| EP | 0133988 A2 | 3/1985 |
| EP | 0143949 A1 | 6/1985 |
| EP | 0369877 A1 | 5/1990 |
| EP | 0495907 A1 | 7/1992 |
| EP | 0601052 A1 | 6/1994 |
| EP | 0679717 A2 | 11/1995 |
| EP | 1037658 A1 | 9/2000 |
| EP | 1277716 A1 | 1/2003 |
| EP | 1675956 A1 | 7/2006 |
| EP | 0812357 B1 | 1/2007 |
| EP | 2496691 A2 | 9/2012 |
| EP | 2704737 A2 | 3/2014 |
| EP | 2543727 B1 | 8/2016 |
| EP | 3248618 A1 | 11/2017 |
| JP | 2004-525630 A | 8/2004 |
| JP | 2006-071409 A | 3/2006 |
| JP | 2006-512407 A | 4/2006 |
| JP | 2007-524686 A | 8/2007 |
| JP | 2007-525443 A | 9/2007 |
| JP | 2008-502590 A | 1/2009 |
| JP | 2013-509201 A | 3/2013 |
| JP | 2014-508143 A | 4/2014 |
| JP | 2014-519809 A | 8/2014 |
| JP | 2018-087224 A | 6/2018 |
| WO | WO-87/05330 A1 | 9/1987 |
| WO | WO 88/07089 A1 | 9/1988 |
| WO | WO-93/004699 A1 | 3/1993 |
| WO | WO 93/15722 A1 | 8/1993 |
| WO | WO 96/14339 A1 | 5/1996 |
| WO | WO-96/027011 A1 | 9/1996 |
| WO | WO 98/05787 A1 | 2/1998 |
| WO | WO 98/23289 A1 | 6/1998 |
| WO | WO-98/050431 A2 | 11/1998 |
| WO | WO 99/25044 A1 | 5/1999 |
| WO | WO 99/51642 A1 | 10/1999 |
| WO | WO 99/58572 A1 | 11/1999 |
| WO | WO 00/009560 A2 | 2/2000 |
| WO | WO-2000/024417 A1 | 5/2000 |
| WO | WO 00/032767 A1 | 6/2000 |
| WO | WO 00/042072 A2 | 7/2000 |
| WO | WO 01/002440 A1 | 1/2001 |
| WO | WO 02/044215 A2 | 6/2002 |
| WO | WO 02/060919 A2 | 8/2002 |
| WO | WO 02/060955 A2 | 8/2002 |
| WO | WO 02/072605 A2 | 9/2002 |
| WO | WO 02/096948 A2 | 12/2002 |
| WO | WO 03/074569 A2 | 9/2003 |
| WO | WO 2004/016750 A2 | 2/2004 |
| WO | WO 2004/029207 A2 | 4/2004 |
| WO | WO 2004/035752 A2 | 4/2004 |
| WO | WO 2004/063351 A2 | 7/2004 |
| WO | WO 2004/074455 A2 | 9/2004 |
| WO | WO 2004/099249 A2 | 11/2004 |
| WO | WO 2005/018572 A2 | 3/2005 |
| WO | WO 2005/040217 A2 | 5/2005 |
| WO | WO-2005/044859 A2 | 5/2005 |
| WO | WO 2005/047327 A2 | 5/2005 |
| WO | WO 2005/063808 A1 | 7/2005 |
| WO | WO 2005/063815 A2 | 7/2005 |
| WO | WO 2005/070963 A1 | 8/2005 |
| WO | WO 2005/077981 A2 | 8/2005 |
| WO | WO 2005/080586 A1 | 9/2005 |
| WO | WO 2005/092925 A2 | 10/2005 |
| WO | WO 2005/123780 A2 | 12/2005 |
| WO | WO 2006/019447 A1 | 2/2006 |
| WO | WO 2006/047350 A2 | 5/2006 |
| WO | WO 2006/085967 A2 | 8/2006 |
| WO | WO 2006/138610 A2 | 12/2006 |
| WO | WO 2007/122511 A2 | 11/2007 |
| WO | WO-2007/136789 A2 | 11/2007 |
| WO | WO 2007/141580 A2 | 12/2007 |
| WO | WO 2008/037311 A1 | 4/2008 |
| WO | WO 2009/015345 A1 | 1/2009 |
| WO | WO-2009/023386 A2 | 2/2009 |
| WO | WO 2009/064777 A2 | 5/2009 |
| WO | WO-2009/089004 A1 | 7/2009 |
| WO | WO 2011/053982 A2 | 5/2011 |
| WO | WO-2011/124718 A1 | 10/2011 |
| WO | WO-2012/068630 A1 | 5/2012 |
| WO | WO-2012/068636 A1 | 5/2012 |
| WO | WO 2012/149440 A2 | 11/2012 |
| WO | WO-2013/059299 A1 | 4/2013 |
| WO | WO 2013/063702 A1 | 5/2013 |

(56) References Cited

FOREIGN PATENT DOCUMENTS

| | | |
|---|---|---|
| WO | WO 2014/009707 A1 | 1/2014 |
| WO | WO 2014/012085 A2 | 1/2014 |
| WO | WO-2014/150973 A1 | 9/2014 |
| WO | WO-2014/194274 A2 | 12/2014 |
| WO | WO 2015/066550 A1 | 5/2015 |
| WO | WO 2015/066557 A1 | 5/2015 |
| WO | WO-2015/107025 A1 | 7/2015 |
| WO | WO-2016/069889 A1 | 5/2016 |
| WO | WO 2016/087648 A1 | 6/2016 |
| WO | WO 2016/179707 A1 | 11/2016 |
| WO | WO 2017/185177 A1 | 11/2017 |
| WO | WO 2018/005954 A2 | 1/2018 |
| WO | WO 2019/040674 A1 | 2/2019 |
| WO | WO-2020/142740 A1 | 7/2020 |
| WO | WO-2022/006153 A1 | 1/2022 |

OTHER PUBLICATIONS

Atwell et al., "Stable heterodimers from remodeling the domain interface of a homodimer using a phage display library," J. Mol. Biol., vol. 270: 26-35 (1997).

Bennett, L. et al., "Interferon and Granulopoiesis Signatures in Systemic Lupus Erythematosus Blood," J. Exp. Med., vol. 197 (6): 711-723 (2003).

Bowman et al., "Measurement of fatigue and discomfort in primary Sjogren's syndrome using a new questionnaire tool," Rheumatology 2004; 43:758-764.

Bowman et al., "Randomized Controlled Trial of Rituximab and Cost-Effectiveness Analysis in Treating Fatigue and Oral Dryness in Primary Sjogren's Syndrome," Arthritis & Rheumatology, vol. 69, No. 7, Jul. 2017, pp. 1440-1450.

Brkic et al., "Prevalence of interferon type I signature in CD14 monocytes of patients with Sjögren's syndrome and association with disease activity and BAFF gene expression," Ann. Rheum. Dis. 2013, 72(5): 728-735.

Burge et al., "Evaluation of RNase therapy in systemic lupus erythematosus: a randomised phase 2a clinical trial of RSLV-132," Lupus Science & Medicine, 2024; 11; e001113.

Chandran et al., "Functional Assessment of Chronic Illness Therapy-Fatigue Scale is valid in patients with psoriatic arthritis," Ann Rheum Dis 2007; 66:936-939.

Chen et al., "Effects of Receptor Binding on Plasma Half-life of Bifunctional Transferrin Fusion Proteins," Mol Pharm 2011;8: 457-465.

Chiang et al., "Immune Complex-Mediated Cell Activation from Systemic Lupus Erythematosus and Rheumatoid Arthritis Patients Elaborate Difference Requirements for IRAK1/4 Kinase Activity across Human Cell Types," J Immunol 2011;186 (2): 1279-1288.

Chiche et al., "Modular Transcriptional Repertoire Analyses of Adults With Systemic Lupus Erythematosus Reveal Distinct Type I and Type II Interferon Signatures," Arthritis & Rheumatology, vol. 66, No. 6, Jun. 2014, pp. 1583-1595.

Clinical Trials "A Study of RSLV-132 in Subjects with Primary Sjogren's Syndrome (RSLV-132)," US National Library of Medicine, ClinicalTrials.gov, Feb. 23, 2018, 5 pages, May Be Retrieved at https://clinicaltrials.gov/ct2/show/study/NCT03247686>.

Database UniProt [Online] "Deoxyribonuclease gamma, Dnase1L3", Accession No. Q13609 (Nov. 1, 1997), https://www.uniprot.org/uniprotkb/Q13609/entry.

Database UniProt [Online] "Deoxyribonuclease-1, DNase1", Accession No. P24855 (Mar. 1, 1992), https://www.uniprot.org/uniprotkb/P24855/entry.

DATABASE UniProt [Online] "Deoxyribonuclease-2-alpha", Accession No. O00115 (Jul. 15, 1998), https://www.uniprot.org/uniprotkb/O00115/entry.

Database UniProt [Online] "Deoxyribonuclease-2-beta", Accession No. Q8WZ79 (Mar. 1, 2002) https://www.uniprot.org/uniprotkb/Q8WZ79/entry.

Database UniProt [Online] "Interferon Regulatory factor 7", Accession No. P70434 (Feb. 1, 1997), https://www.uniprot.org/uniprotkb/P70434/entry.

Database UniProt [Online] "Interferon-induced GTP-binding protein Mx1", Accession No. P09922 (Jul. 1, 1989), https://www.uniprot.org/uniprotkb/P09922/entry.

Database UniProt [Online] "Interferon-induced protein with tetratricopeptide repeats 1", Accession No. Q64282 (Nov. 1, 1996), https://www.uniprot.org/uniprotkb/Q64282/entry.

Database UniProt [Online] "Ribonuclease Pancreatic, RNase", Accession No. P07998 (Feb. 1, 2005), https://www.uniprot.org/uniprotkb/P07998/entry.

Database UniProt [Online] "S-adenosylmethionine-dependent nucleotide dehydratase RSAD2", Accession No. Q8CBB9 (Mar. 1, 2003), https://www.uniprot.org/uniprotkb/Q8CBB9/entry.

Database UniProt [Online] "Three-prime repair exonuclease 1", Accession No. Q9NSU2 (Oct. 1, 2000), https://www.uniprot.org/uniprotkb/Q9NSU2/entry.

Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel., vol. 23(4):195-202 (2010).

De Weerd, N. et al., "Type I Interferon Receptors: Biochemistry and Biological Functions," The Journal of Biological Chemistry, vol. 282(28): 20053-20057 (2007).

Doedens, J. et al., "Blood-Borne RNA Correlates with Disease Activity and IFN-Stimulated Gene Expression in Systemic Lupus Erythematosus," The Journal of Immunology, vol. 197: 18 pages (2016).

Driedonks et al., "Circulating Y-RNAs in Extracellular Vesicles and Ribonucleoprotein Complexes; Implications for the Immune System," Front Immunol. 2019: 9, Article 3164.

Dulaglutide, Drug Bank, Accession No. DB09045, Drug created Apr. 29, 2015, 6 pages.

Dörner et al., "THU0313 Double-Blind, Randomized Study of VAY736 Single Dose Treatment in Patients with Primary Sjögren's Syndrome (PSS)," Annals of the Rheumatic Diseases, Jun. 9, 2016, pp. 300-301.

Eloranta et al., "Regulation of the Interferon-alpha Production Induced by RNA-Containing Immune Complexes in Plasmacytoid Dendritic Cells," Arthritis & Rheumatology 2009; 60(8): 2418-2427.

Extended European Search Report for EP Application No. 18167227.0 dated Feb. 4, 2019, 7 pages.

Extended European Search Report for EP Application No. 18190143.0 dated Dec. 12, 2018, 6 pages.

Fisher et al., "OP0202: Effect of RSLV-132 on Fatigue in Patients with Primary Sjögren's Syndrome—Results of a Phase II Randomised, Double-Blind, Placebo-Controlled, Proof of Concept Study", Scientific Abstracts, Oral Presentations, Jun. 13, 2019, p. 177.1-177.

Furie, R. et al., "Anifrolumab, an Anti-Interferon-a Receptor Monoclonal Antibody, in Moderate-to-Severe Systemic Lupus Erythematosus," Arthritis & Rheumatology, vol. 69(2): 376-386 (2017).

George et al., "An analysis of protein domain linkers: their classification and role in protein folding," Protein Engineering 2002;15: 871-879.

Guo, J. et al., "Clinical Applications of DNaseq," International Journal of Pathology and Clinical Medicine, Apr. 2009, pp. 125-129, vol. 29, No. 2 (with English abstract).

Haak-Frendscho, M et al., "Inhibition of interferon-γ by an interferon-γ receptor immunoadhesin," Immunology, vol. 79:594-599 (1993).

Haldorsen et al., "A five-year prospective study of fatigue in primary Sjögren's syndrome," Arthritis Research & Therapy 2001, 13:R167.

Hall et al., "Molecular Subsetting of Interferon Pathways in Sjögren's Syndrome," Sep. 2015, Arth. & Rheum. 67(9), 2437-2446.

Hickman et al., "A recognition marker required for uptake of a lysosomal enzyme by cultured fibroblasts," Biochemical and Biophysical Research Communications, Mar. 1974;57(1): 55-61.

(56) References Cited

OTHER PUBLICATIONS

Huang et al., "Matrix-assisted laser desorption/ionization mass spectometry compatible beta-elimination of O-linked oligosaccharides" Rapid Communiaction in Mass Specrometry, vol. 16, p. 1199-1204 (2002).
Hur et al, "Potential Implications of Long Noncoding RNAs in Autoimmune Diseases," Immune Network 2019; 19(1):e4.
International Nonproprietary Names for Pharmaceutical Substances (INN): Recommended INN: List 75, WHO Drug Information vol. 30 (1) 78 pages (2016 ).
International Preliminary Report on Patentability for International Application No. PCT/US2010/055131, dated May 8, 2012, 9 pages.
International Preliminary Report on Patentability for International Application No. PCT/US2012/035614, dated Mar. 25, 2014, 8 pages.
International Preliminary Report on Patentability for International Application No. PCT/US2020/012258 dated Jul. 15, 2021, 10 pages.
International Preliminary Report on Patentability for International Application No. PCT/US2021/039683 dated Jan. 12, 2023, 8 pages.
International Preliminary Report on Patentability, PCT/US2018/047614, dated Feb. 25, 2020, 7 pages.
International Search Report and Written Opinion for International Application No. PCT/US2020/012258 dated Jun. 25, 2020, 6 pages.
International Search Report and Written Opinion for International Application No. PCT/US2021/039683 dated Oct. 26, 2021.
Invitation to Pay Additional Fees in International Application No. PCT/US2020/012258 dated Apr. 7, 2020, 8 pages.
Iyoda et al., "All-trans-retinoic acid aggravates cryoglobulin-associated membranoproliferative glomerulonephritis in mice," Nephrol Dial Transplant (2007) 22: 3451-3461.
Jaeger, "Digit Symbol Substitution Test: The Case for Sensitivity Over Specificity in Neuropsychological Testing," Journal of Clinical Psychopharmacology, vol. 38, No. 5, Oct. 2018, pp. 513-519.
Kattah et al., "The U1-snRNP complex: structural properties relating to autoimmune pathogenesis in rheumatic diseases," Immunol. Rev. 2010; 233: 126-145.
Katze et al., "Innate immune modulation by RNA viruses: emerging insights from functional genomics," Nat. Rev. Immunol. 2008; 8: 644-654.
Kennedy, W. et al., "Association of the interferon signature metric with serological disease manifestations but not global activity scores in multiple cohorts of patients with SLE," Lupus Science & Medicine, vol. 2:e000080: 12 pages (2015).
Khamashta, M. et al., "Sifalimumab, an anti-interferon-? monoclonal antibody, in moderate to severe systemic lupus erythematosus: a randomised, double-blind, placebo-controlled study," Ann Rheum Dis., pp. 1-8 (2016).
Klein et al., "Progress in overcoming the chain association issue in bispecific heterodimeric IgG antibodies," mAbs, vol. 4(6):653-663 (2012).
Labrijn et al., "Efficient generation of stable bispecific IgG1 by controlled Fab-arm exchange," PNAS, vol. 110 (13):5145-5150 (2013).
Langer, J.A., et al., "Bovine type I interferon receptor protein BoIFNAR-1 has high-affinity and broad specificity for human type I interferons," FEBS Letters, vol. 421: 131-135 (1998).
Lau et al., "RNA-associated autoantigens activate B cells by combined B cell antigen receptor/Toll-like receptor 7 engagement,", J. Exp. Med. 202(9): 1171-1177.
Li, "Clinical and Histopathologic Dermatology" World Publishing Xi'an Co., Ltd., p. 246, published in Jan. 2015.
Li, H. et al., "Dynamic Modulation of Binding Affinity as a Mechanism for Regulating Interferon Signaling," J Mol Biol., vol. 429(16):2571-2589 (2017).
Malladi et al., "Primary Sjögren's Syndrome as a systemic disease: a study of participants enrolled in an international Sjögren's Syndrome registry," Arthritis Care Res. Jun. 2012; 64(6): 911-918.
Marinaro et al., "O-glycosylation delays the clearance of human IGF-binding protein-6 from the circulation," European Journal of Endocrinology 2000;142: 512-516.
Mathsson et al., "Cytokine induction by circulating immune complexes and signs of in-vivo complement activation in systemic lupus erythematosus are associated with the occurrence of anti-Sjogren's syndrome A antibodies," Clin Expt Immunol 2007; 147: 513-520.
Means et al., "Human lupus autoantibody-DNA complexes activate DCs through cooperation of CD32 and TLR9," J. Clin. Invest. 2005; 115(2): 407-417.
Merchant et al., "An efficient route to human bispecific IgG," Nat Biotechnol., vol. 16(7):677-681 (1998).
Moutsopoulos et al., "Anti-Ro (SSA)/La (SSB) antibodies and Sjögren's syndrome", Clin. Rheumatol. 1990; 9: 123-130.
Nezos et al., "Type I and II interferon signatures in Sjögren's syndrome pathogenesis: Contributions in distinct clinical phenotypes and Sjögren's related lymphomagenesis," J. Autoimmun. 2015, 63: 47-58.
Noll et al., "Self-extracellular RNA acts in synergy with exogenous danger signals to promote inflammation," PLoS ONE, 2017; 12:e0190002.
Notice of Allowance for U.S. Appl. No. 17/167,725 dated Jul. 27, 2023, 8 pages.
Notice of Allowance issued Feb. 17, 2021, in U.S. Appl. No. 16/229,431, filed Dec. 21, 2018; 8 pages.
Nuclease (biology), Brittanica Online Encyclopedia, 1 page, [Online] [Retrieved on Feb. 20, 2013], Retrieved from the Internet <URL:http://www.britannica.com/EBchecked/topic/421887/nuclease?sections=421887main&vie . . . >.
Payes et al., "Genetic Engineering of Antibody Molecules Biomolecules Sensing View project Effect of glycosylation on antibody function View project", Rev. Cell Biol. Mol. Medicine, vol. 1, No. 3, Jan. 1, 2015, pp. 1-53.
Piehler, J. et al., "Structural and dynamic determinants of type I interferon receptor assembly and their functional interpretation," Immunological Reviews, vol. 250: 317-334 (2012).
Posada et al., "Improvement of Severe Fatigue Following Nuclease Therapy in Patients with Primary Sjögren's Syndrome: A Randomized Clinical Trial," Arthritis & Rheumatology, vol. 73, No. 1, Jan. 2021, pp. 143-150.
Pottier et al., "Rethinking the INN system for therapeutic antibodies", mAbs, vol. 9, No. 1, Jan. 2, 2017, pp. 5-11.
Ramos-Casals et al., "Primary Sjogren's syndrome: new clinical and therapeutic concepts," Ann Rheum Dis. 2005; 64: 347-354.
Roth et al. "Identification and Quantification of Protein Glycosylation," International Journal of Carbohydrate Chemistry 2012; pp. 1-10.
Sampei et al., "Identification and Multidimensional Optimization of an Asymmetric Bispecific IgG Antibody Mimicking the Function of Factor VIII Cofactor Activity," PLOS One, vol. 8(2): e57479: 13 pages (2013).
Segal et al., "Prevalence, Severity and Predictors of Fatigue in Primary Sjogren's Syndrome," Arthritis Rheum. Dec. 15, 2005; 59(12): 1780-1787.
Seror et al., "EULAR Sjogren's syndrome disease activity index: development of a consensus systemic disease activity index for primary Sjogren's syndrome," Ann Rheum Dis. 2010; 69(6): 1103-1109.
Seror et al., "EULAR Sjögren's syndrome disease activity index (ESSDAI): a user guide," RMD Open 2015; 1:e000022.
Seror et al., "EULAR Sjögren's Syndrome Patient Reported Index (ESSPRI): development of a consensus patient index for primary Sjögren's syndrome," Ann Rheum Dis 2011; 70:968-972.
Skopouli et al., "Clinical Evolution, and Morbidity and Mortality of Primary Sjögren's Syndrome,", Semin. Arthritis Rheum. 29: 296-304.
Sojar et al., "[27] Chemical deglycosylation of glycoproteins," Methods Enzymol 1987; 138: 341-350.
Sojar et al., "Characterization of Rat Ovarian Lutropin Receptor," Journal of Biological Chemistry; 1989; 264(5): 2552-2559.
Stahl et al., "Evidence for specific recognition sites mediating clearance of lysosomal enzymes in vivo," PNAS 1976; 73(11): 4045-4049.

(56) References Cited

OTHER PUBLICATIONS

Strop et al., "Generating bispecific human IgG1 and IgG2 antibodies from any antibody pair," J. Mol. Biol., vol. 420 (3):204-219 (2012).
Strombeck et al., "Assessment of fatigue in primary Sjögren's syndrome: the Swedish version of the Profile of Fatigue," Scandinavian Journal of Rheumatology, 34:6, 455-459.
Tennant, "Assessment of Fatigue in Older Adults: The FACIT Fatigue Scale (Version 4)," Try This: Best Practices in Nursing Care to Older Adults, Issue 30, 2012; revised 2019.
Theofilopoulos et al., "Sensors of the innate immune system: their link to rheumatic diseases," 2010, Nat. Rev. Rheumatol., 6(3): 146-156.
Thorpe et al., "Modification of the carbohydrate in ricin with metaperiodate-cyanoborohydride mixtures," Eur J Biochem 1985; 147, 197-206.
Thotakura et al., "[28] Enzymatic deglycosylation of glycoproteins," Methods Enzymol 1987; 138: 350-359).
United States Advisory Action, U.S. Appl. No. 14/174,167, filed Oct. 17, 2014, 4 pages.
United States Office Action in U.S. Appl. No. 15/679,746; mailed Jul. 21, 2020, 13 pages.
United States Office Action in U.S. Appl. No. 15/679,746; mailed Mar. 25, 2021, 14 pages.
United States Office Action in U.S. Appl. No. 16/229,431; mailed Feb. 24, 2020, 6 pages.
United States Office Action in U.S. Appl. No. 16/229,431; mailed Jun. 18, 2019, 6 pages.
United States Office Action, U.S. Appl. No. 13/505,421, filed Jun. 12, 2014, 13 pages.
United States Office Action, U.S. Appl. No. 13/197,731, filed Feb. 27, 2013, 17 pages.
United States Office Action, U.S. Appl. No. 13/505,421, filed Oct. 22, 2013, 13 pages.
United States Office Action, U.S. Appl. No. 13/822,215, filed Feb. 28, 2018, 9 pages.
United States Office Action, U.S. Appl. No. 14/174,167, filed Aug. 25, 2014, 12 pages.
United States Office Action, U.S. Appl. No. 14/174,167, filed May 8, 2014, 18 pages.
United States Office Action, U.S. Appl. No. 14/599,567, filed Jul. 21, 2017, 9 pages.
United States Restriction Requirement in U.S. Appl. No. 13/822,215; mailed Jul. 21, 2017, 8 pages.
United States Restriction Requirement in U.S. Appl. No. 15/679,746; mailed Jan. 23, 2020, 6 pages.
United States Restriction Requirement in U.S. Appl. No. 15/679,746; mailed May 21, 2019, 5 pages.
United States Restriction Requirement, U.S. Appl. No. 14/174,167, filed Apr. 15, 2014, 6 pages.
United States Restriction Requirement, U.S. Appl. No. 13/197,731, filed Aug. 17, 2012, 11 pages.
United States Restriction Requirement, U.S. Appl. No. 13/197,731, filed Aug. 3, 2012, 11 pages.
United States Restriction Requirement, U.S. Appl. No. 13/197,731, filed Nov. 16, 2012, 7 pages.
United States Restriction Requirement, U.S. Appl. No. 13/505,421, filed Apr. 16, 2013, 8 pages.
United States Restriction Requirement, U.S. Appl. No. 13/505,421, filed Aug. 6, 2013, 8 pages.
United States Restriction Requirement, U.S. Appl. No. 14/516,161, filed Jan. 26, 2017, 6 pages.
United States Restriction Requirement, U.S. Appl. No. 14/599,567, filed Apr. 6, 2017, 5 pages.
Van den Steen et al., "Concepts and Principles of O-Linked Glycosylation," Critical Reviews in Biochemistry and Molecular Biology, 1998; 33(3): 151-208.
Wang et al., "An Overview of Methodologies in Studying lncRNAs in the High-Throughput Era: When Acronyms ATTACK!", Methods in Molecular Biology, 2019; 1933: 1-30.
Weenen et al., "Long-Acting Follicle-Stimulating Hormone Analogs Containing N-Linked Glycosylation Exhibited Increased Bioactivity Compared with O-Linked Analogsin Female Rats," J Clin Endocrinol Metab 2004; 89(1): 5204-5212.
Wu et al., "Internal Medicine" China Medical Science Press, p. 699, published in Jun. 2017.
"A Study of RSLV-132 in Subjects with Primary Sjogren's Syndrome (RSLV-132)," US National Library of Medicine, ClinicalTrials. gov, Feb. 23, 2018, 5 pages; retrieved from: https://clinicaltrials.gov/ct2/show/study/NCT0324 7686>.
"Autoimmune Disorders," MedlinePlus, National Institutes of Health/ U.S. National Library of Medicine, Review Date May 21, 2017, Last Updated Feb. 7, 2018, 4 pages; retrieved from: https://medlineplus.gov/ency/article/000816.htm.
"Nuclease (biology)," Britannica Online Encyclopedia, 1 page, [Online] [Retrieved on Feb. 20, 2013], Retrieved from the Internet <URL:http://www.britannica.com/EBchecked/topic/421887/nuclease?sections=421887main&vie . . . >.
Båve, U. et al., "Activation of the Type I Interferon System in Primary Sjögren's Syndrome," Arthritis & Rheumatism, Apr. 2005, pp. 1185-1195, vol. 52, No. 4.
Beintema J.J. et al., "Differences in Glycosylation Pattern of Human Secretory Ribonucleases," Biochem. J., 1988, pp. 501-505, vol. 255.
Berland, R., et al., "Toll-like Receptor 7-Dependent Loss of B Cell Tolerance in Pathogenic Autoantibody Knockin Mice," Immunity, Sep. 2006, pp. 429-440, vol. 25.
Bitonti, A.J. et al., "Pulmonary Delivery of an Erythropoietin Fc Fusion Protein in Non-Human Primates Through an Immunoglobulin Transport Pathway," PNAS, Jun. 29, 2004, pp. 9763-9768, vol. 101, No. 26.
Boix, E. et al., "Mammalian Antimicrobial Proteins and Peptides: Overview on the RNase A Superfamily Members Involved in Innate Host Defence," Molecular Biosystems, 2007, pp. 317-335, vol. 3.
Brekke, O.H. et al., "Human IgG Isotype-Specific Amino Acid Residues Affecting Complement-Mediated Cell Lysis and Phagocytosis," European Journal of Immunology, 1994, pp. 2542-2547, vol. 24.
Brekke, O.H. et al., "Therapeutic Antibodies for Human Diseases at the Dawn of the Twenty-First Century," Nature Reviews, Jan. 2003, pp. 52-62, vol. 2.
Burge, D.J. et al., "Safety, Pharmacokinetics, and Pharmacodynamics of RSLV-132, an RNase-Fc Fusion Protein in Systemic Lupus Erythematosus: A Randomized, Double-Blind, Placebo-Controlled Study," Lupus, 2017, pp. 825-834, vol. 26.
Canfield, S.M. et al., "The Binding Affinity of Human IgG for its High Affinity Fc Receptor Is Determined by Multiple Amino Acids in the CH2 Domain and Is Modulated by the Hinge Region," J. Exp. Med., vol. 173:1483-1491 (1991).
Carsana, A. et al. "Structure of the Bovine Pancreatic Ribonuclease Gene: The Unique Intervening Sequence in the 5' Untranslated Region Contains a Promoter-Like Element," Nucleic Acids Research, Jun. 24, 1988, pp. 5491-5550, vol. 16, No. 12.
Chan, A.C. et al., "Therapeutic Antibodies for Autoimmunity and Inflammation," Nature Reviews Immunology, May 2010, pp. 301-316, vol. 10.
Clark, E.A. et al., "CD16-Mediated Antibody Dependent Cellular Cytotoxicity is Required for B Cell Depletion by a Small Modular ImmunoPharmaceutical Specific for CD20," Blood, 2003, p. 646a, Abstract #2388, vol. 102, No. 11.
Davis, Jr., J.C. et al., "Recombinant Human Dnase I (rhDNase) in Patients with Lupus Nephritis," Lupus, 1999, pp. 68-76, vol. 8.
Definition of Antibody-dependent cell-mediated cytotoxicity (ADDC). Dictionary of Biology, 1st Ed. p. 434 (2010)—2 pages submitted.
English Translation of "Reference A"—Definition of Antibody-dependent cell-mediated cytotoxicity (ADDC). Dictionary of Biology, 1st Ed. p. 434 (2010); 2 pages submitted.
Deshpande, A. et al., "Kinetic analysis of cytokine-mediated receptor assembly using engineered FC heterodimers," Protein Science, vol. 22 (8):1100-1108 (2013).
Dübel, S., "Novel Recombinant Antibody Constructs and Fusion Proteins for Therapy and Research," Department of Biotechnology, Technical University of Braunschweig, Germany, Jun. 17, 2008, 15 pages.

(56) References Cited

OTHER PUBLICATIONS

Dwyer, M.A. et al., "Expression and Characterization of a DNase I-Fc Fusion Enzyme," The Journal of Biological Chemistry, Apr. 2, 1999, pp. 9738-9743, vol. 274, No. 14.

Fenton et al., "Anti-dsDNA Antibodies Promote Initiation, and Acquired Loss of Renal Dnase1 Promotes Progression of Lupus Nephritis in Autoimmune (NZBxNZW)F1 Mice," PloS One, 2009 (published online Dec. 2009), e8474, vol. 4, No. 12.

Fujihara, J. et al., "Comparative Biochemical Properties of Vertebrate Deoxyribonuclease I," Comparative Biochemistry and Physiology, Part B, 2012, pp. 263-273, vol. 163.

Gavalchin, J. et al. "The NZB X SWR Model of Lupus Nephritis. I. Cross-Reactive Idiotypes of Monoclonal Anti-DNA Antibodies in Relation to Antigenic Specificity, Charge, and Allotype. Identification of Interconnected Idiotype Families Inherited from the Normal SWR and the Autoimmune NZB Parents," The Journal of Immunology, Jan. 1, 1987, pp. 128-137, vol. 138.

GenBank Accession No. CAA11830, Nov. 20, 1998, 2 pages, [Online] Retrieved from the Internet: http://www.ncbi.nlm.nih.gov/protein/CAA 11830>.

GenBank Accession No. CAA55817.1 (May 20, 1994), Filipenko, M.L. et al., NCBI Sequence Viewer v2.0, 3 pages, [online] [Retrieved on Dec. 12, 2013] Retrieved from the Internet: http://www.ncbi.nlm.nih.gov/protein/CAA55817.1.

Gillies, S.D. et al., "Improving the Efficacy of Antibody-Interleukin 2 Fusion Proteins by Reducing Their Interaction with Fc Receptros", Cancer Res. (1999) vol. 59, p. 2159-2166.

Gunasekaran, K. et al., "Enhancing antibody Fc heterodimer formation through electrostatic steering effects: applications to bispecific molecules and monovalent IgG," J. Biol. Chem., 285(25):19637-19646 (2010).

Ha, J-H. et al. "Immunoglobulin Fc Heterodimer Platform Technology: From Design to Applications in Therapeutic Antibodies and Proteins," Frontier in Immunology, vol. 7:394, 16 pages (2016).

Jefferis, R. et al., "Interaction Sites on Human IgG-Fc for FcgammaR: Current Models," Immunology Letters, Jun. 3, 2002, pp. 57-65, vol. 82, No. 1-2.

Johnson, R.J. et al., "Inhibition of Human Pancreatic Ribonuclease by the Human Ribonuclease Inhibitor Protein," J. Mol. Biol., 2007, pp. 434-449, vol. 368.

Karasinska, J.M., "Searching for the Aircardi-Goutieres Syndrome Genes: TREX1 and Ribonuclease H2 Make the Cut," Clin. Genet., 2006, pp. 457-461, vol. 70.

Krauss, J. et al., "Efficient killing of CD22+ tumor cells by a humanized diabody-RNase fusion protein", Biochemical and Biophysical Research Communications, 331(2):595-602 (2005).

Ledbetter, J.A., "Discovery of Biological Drugs: Seattle at the Leading Edge," Grand Rounds, Department of Medicine, University of Washington, Feb. 4, 2010, 36 pages.

Lewis, S. et al., "Generation of bispecific IgG antibodies by structure-based design of an orthogonal Fab interface," Nature Biotechnology, 32(2), 45 pages (2014).

Linsley, P.S. et al., "CTLA-4 Is a Second Receptor for the B Cell Activation Antigen B7," J. Exp. Med., Sep. 1991, pp. 561-569, vol. 174.

Lovgren, T., et al., "Induction of Interferon-alpha by Immune Complexes or Liposomes Containing Systemic Lupus Erythematosus Autoantigen and Sjogren's Syndrome Autoantigen-Associated RNA", Arthritis and Rheumatism (2006) vol. 54, No. 6, p. 1917-1927.

Macanovic, M. et al., "The treatment of systemic lupus erythematosus (SLE) in NZB/W F1 hybrid mice; studies with recombinant murine DNase and with dexamethasone," Clin Exp Immunol, 1996, pp. 243-252, vol. 106.

Man & Zhong, "Advances in the pathogenesis and etiology of Sjogren's syndrome" Journal of Clinical Stomatology, vol. 24, Issue 4; pp. 251-253 (Apr. 2008) (English abstract only).

Martinez-Valle, F. et al., "DNase 1 Activity in Patients with Systemic Lupus Erythematosus: Relationship with Epimediological, Clinical Immunological and Therapeutical Features," Lupus, 2009, pp. 418-423, vol. 18, No. 5.

Mathew, et al., "Humanized immunotoxins: A new generation of immunotoxins for targeted cancer therapy," Cancer Sci (Aug. 2009) vol. 100(8):1359-1365.

Menzel, et al., "Human Antibody RNase Fusion Protein Targeting CD30+ Lymphomas," Blood, Apr. 2008, pp. 3830-3837, vol. 111, No. 7.

Moore, G., et al. "A novel bispecific antibody formal enables simultaneous bivalent and monovalent co-engagement of distinct target antigens," MABS, vol. 3(6):546-557 (2011).

Ni, Y. et al., "Research Progress of DNaseq," International Journal of Pathology and Clinical Medicine, Dec. 2006, pp. 531-535, vol. 26, No. 6.

Pan, C.Q. et al., "Ca2+-Dependent Activity of Human DNase I and Its Hyperactive Variants," Protein Science, 1999, pp. 1780-1788, vol. 8.

Pan, C.Q et al., "Improved Potency of Hyperactive and Actin-Resistant Human DNase I Variants for Treatment of Cystic Fibrosis and Systemic Lupus Erythematosus," The Journal of Biological Chemistry, Jul. 17, 1998, pp. 18374-18381, vol. 273, No. 29.

Prince, W.S. et al., "Pharmacodynamics of Recombinant Human DNase I in Serum," Clin. Exp. Immunol., 1998, pp. 289-296, vol. 113.

Ridgway, J. et al., "Knobs-into-holes' engineering of antibody CH3 domains for heavy chain heterodimerization," Protein Engineering, vol. 9(7):617-621 (1996).

Rodriguez, A.M. et al., "Identification, Localization and Expression of Two Novel Human Genes Similar to Deoxyribonuclease I," Genomics, 1997, pp. 507-513, vol. 42.

Rutkoski, T.J. and Raines, R.T., "Evasion of ribonuclease inhibitor as a determinant of ribonuclease cytotoxicity" Curr. Pharm. Biotechnol., (2008), vol. 9, pp. 185-199.

Shak, S. et al., "Recombinant Human DNase I Reduces the Viscosity of Cystic Fibrosis Sputum," Proc. Natl. Acad. Sci., Dec. 1990, vol. 87, pp. 9188-9192.

Shields, R.L. et al., "High resolution mapping of the binding site on human IgGI for FcγRI, FcγRII, FcγRIII, and FcRn and design of IgGI variants with improved binding to the FcγR" J Biol Chem, 276(9):6591-6604 (Mar. 2001).

Skolnick, J. et al., "From Genes to Protein Structure and Function: Novel Applications of Computational Approaches in the Genomic Era," TIBTECH, Jan. 2000, vol. 18, pp. 34-39.

Sondermann, P. et al., "The 3.2-angstrom Crystal Structure of the Human IgG1 Fc Fragment-FcgammaRIII Complex," Nature, Jul. 20, 2000, pp. 267-273, vol. 406, No. 6793.

Spiess, C. et al., "Alternative molecular formats and therapeutic applications for bispecific antibodies," Molecular Immunology, vol. 67(2 Pt A):95-106 (2015).

Stavenhagen, J.B. et al., "Fc Optimization of Therapeutic Antibodies Enhances Their Ability to Kill Tumor Cells in Vitro and Controls Tumor Expansion in Vivo Via Low-Affinity Activating Fcgamma Receptors," Cancer Research, 2007, pp. 8882-8890, vol. 67.

Strohl, W.R., "Optimization of Fc-mediated effector functions of monoclonal antibodies," Curr. Opin. Biotechnol., (Nov. 11, 2009) vol. 20, p. 685-691.

Sun, X. et al., "Increased RNase Expression Reduces Inflammation and Prolongs Survival in TLR7 Transgenic Mice," The Journal of Immunology, Feb. 4, 2013, 9 pages.

Tew, M.B. et al., "A molecular analysis of the low serum deoxyribonuclease activity in lupus patients" Arthritis and Rheumatism, (2001), vol. 44, No. 10, pp. 2446-2447.

Van Der Neut Kolfschoten, M. et al., "Anti-Inflammatory Activity of Human IgG4 Antibodies by Dynamic Fab Arm Exchange," Science, vol. 317(5844):1554-1557 (2007).

Video of Medicine Grand Rounds on Feb. 4, 2010 by Jeffrey Ledbetter, Research Professor of Medicine, Division of Rheumatology; Affiliate Associate Professor of Microbiology University of Washington School of Medicine, Can be Viewed at <http://depts.washington.edu/medweb/conferences/GRarchive.html#ledbetter>.

(56) References Cited

OTHER PUBLICATIONS

Von Kreudenstein, T.S. et al., "Improving biophysical properties of a bispecific antibody scaffold to aid developability: Quality by molecular design," MABS, vol. 5(5):646-654 (2013).

Whisstock, J.C. et al., "Prediction of Protein Function from Protein Sequence and Structure," Quarterly Reviews of Biophysics, Cambridge University Press, 2003, pp. 307-340, vol. 36, No. 3.

Yasuda, T. et al., "A Biochemical and Genetic Study on All Non-Synonymous Single Nucleotide Polymorphisms of the Gene Encoding Human Deoxyribonuclease I Potentially Relevant to Autoimmunity," The International Journal of Biochemistry & Cell Biology, 2010, pp. 1216-1225, vol. 42.

Zeng, Z. et al., "Cloning and Characterization of a Novel Human DNase," Biochemical and Biophysical Research Communication, 1997, pp. 499-504, vol. 231.

Zhao, W-P. et al., "Relationship Between RNA Released from Mouse Apoptotic Murine Splenocytes and Autoimmune Disease," Chinese Journal of Biochemistry and Molecular Biology, 2003, pp. 662-666, vol. 19, No. 5 (with English abstract).

European Extended Search Report, European Application No. 10827655.1, Jun. 24, 2013, 11 pages.

European Extended Search Report, European Application No. 12777116.0, Jun. 3, 2015, 6 pages.

European Extended Search Report, European Application No. 16198956.1, mailed May 4, 2017, 3 pages.

Extended European Search Report, European Patent Application No. 10827655.1, Jun. 24, 2013, 10 pages.

Office Action issued Mar. 25, 2021, in U.S. Appl. No. 15/679,746, filed Aug. 17, 2017; 21 pages.

International Patent Application No. PCT/US2010/055131: Invitation to Pay Additional Fees, And, Where Applicable, Protest Fee, mailed Feb. 9, 2011, 2 pages.

International Patent Application No. PCT/US2010/055131: International Search Report and Written Opinion with Notification of Transmittal, mailed Apr. 29, 2011, 18 pages.

International Patent Application No. PCT/US2010/055131: International Preliminary Report on Patentability, mailed May 8, 2012, 9 pages.

International Patent Application No. PCT/US2012/035614: International Search Report and Written Opinion, mailed Sep. 4, 2012, 17 pages.

International Patent Application No. PCT/US2012/035614: International Preliminary Report on Patentability, mailed Mar. 25, 2014, 8 pages.

International Patent Application No. PCT/US2017/040267: Invitation to Pay Additional Fees and Protest Where Applicable, mailed Dec. 19, 2017, 28 pages.

International Patent Application No. PCT/US2017/040267: International Search Report and Written Opinion with Notification of Transmittal, mailed Feb. 14, 2018, 28 pages.

International Patent Application No. PCT/US2017/040267: International Preliminary Report on Patentability, mailed Jan. 1, 2019, 18 pages.

International Patent Application No. PCT/US2018/047614: International Search Report and Written Opinion, mailed Jan. 4, 2019, 11 pages.

* cited by examiner

OPTIMIZED BINUCLEASE FUSIONS AND METHODS

RELATED APPLICATIONS

This application is a continuation of U.S. patent application Ser. No. 16/313,656, filed on Dec. 27, 2018, allowed, which is a 35 U.S.C. § 371 national stage filling of International Application No. PCT/US2017/040267, filed on Jun. 30, 2017, which claims the benefit of U.S. provisional Patent Application No. 62/357,756, filed Jul. 1, 2016. The entire contents of each of these applications are incorporated herein by reference in their entirety.

STATEMENT REGARDING SEQUENCE LISTING

The application contains a Sequence Listing which has been submitted in ASCII format via EFS-Web and is hereby incorporated by reference in its entirety. Said ASCII copy, created on Dec. 22, 2021, is named "RSLV_013_C01US_Sequence-Listing.txt" and is 145,273 bytes in size.

BACKGROUND

Accumulation of (ribo)nucleoprotein particles from dead and dying cells is known to induce an inflammatory cascade in patients with systemic lupus erythematosus (SLE) by at least two mechanisms: (i) Deposition or in situ formation of chromatin/anti-chromatin complexes causes nephritis and leads to loss of renal function; and (ii) nucleic acids complexed with autoantibodies activate innate immunity through toll-like receptor (TLR) 7, 8, and 9 as well as TLR-independent pathway(s). Release of nucleoproteins can serve as a potent antigen for autoantibodies in SLE, providing amplification of B cell and DC activation through co-engagement of antigen receptors and TLRs. Thus, there exists a need for a means to remove the nucleic acid bound to autoantibody antigens and/or attenuate immune stimulation, immune amplification, and immune complex mediated disease in subjects in need thereof, for example, with long-acting nuclease molecules that attack circulating immune complexes by digesting nucleic acids contained therein.

SUMMARY OF THE INVENTION

The invention relates, in part, to optimized binuclease fusion proteins which are tandem binuclease fusion proteins or heterodimeric binuclease fusion proteins which are capable of binding multiple substrates with high nuclease activity. In some aspects, the tandem binuclease fusion proteins comprise one or more DNase1 and one or more RNase1 domains operably linked in tandem to one or more Fc domains. In some aspects, the heterodimeric binuclease fusion proteins comprise a single DNase1 domain and a single RNase1 domain operably linked to one or more Fc domains, such that the DNase1 and RNase1 domains are positioned at either the N- or C-terminus of the Fc domain. In some aspects, the optimized binuclease fusion proteins alleviate the problem of expressing dual-functional nuclease-Fc chains and mitigate potential steric hindrance of one or more nuclease domains. In some aspects, the heterodimeric binuclease fusion proteins comprise one or more mutations in the Fc domain(s) to maximize formation of heterodimers.

In some embodiments the optimized binuclease fusion proteins are tandem binuclease fusion proteins comprising a first nuclease domain, a second nuclease domain and an Fc region, wherein the first nuclease domain is DNase1 and the second nuclease domain is RNase1, wherein the DNase1 is operably linked with or without a linker in tandem from N- to C-terminus to the RNase1, and the RNase1 is operably linked to the N- or C-terminus of an Fc region. The tandem binuclease fusion protein exhibits enhanced pharmacokinetic activity relative to the either first or second nuclease domain alone. Such tandem binuclease fusion proteins exhibit altered, e.g., improved, serum half-life relative to either the first or second nuclease domain alone.

In some aspects the optimized binuclease fusion proteins are heterodimeric binuclease fusion proteins comprising a first nuclease domain, a second nuclease domain and an Fc region, wherein the first nuclease domain is DNase1 and the second nuclease domain is RNase1, wherein the DNase1 is operably linked with or without a linker to the N- or C-terminus of an Fc region, and the RNase1 is operably linked with or without a linker to the N- or C-terminus of an Fc region, thereby forming a heterodimer. The heterodimeric binuclease fusion protein exhibits enhanced pharmacokinetic activity relative to the either first or second nuclease domain alone. Such heterodimeric binuclease fusion proteins exhibit altered, e.g., improved, serum half-life relative to either the first or second nuclease domain alone.

In some aspect the optimized binuclease fusion proteins are those represented in FIG. 1.

In some aspects, the invention provides an optimized binuclease fusion protein comprising human DNase1, human RNase1, and a mutant human IgG1 Fc, wherein the human DNase1 is operably linked via a linker (e.g., a gly-ser linker) to human RNase1, from N-terminus to C terminus, and wherein the human RNase1 is operably linked via a linker to the mutant human IgG1 Fc domain wherein the mutant human IgG1 has a mutant hinge region (e.g., a cysteine substitution, such as with serine, e.g., SCC), and one or more CH2 mutations to reduce Fcγ receptor binding (e.g., P238S, P331S or both P238S and P331S, numbering according to EU index). In one embodiment, the optimized binuclease fusion protein comprises human DNase1 operably linked via a peptide linker (e.g., a gly-ser linker) to human RNase1 (N-terminus-DNase1-linker-RNase1-C terminus) and the human RNase1 is operably linked via a peptide linker (e.g., a gly-ser linker) to a mutant human IgG1 Fc domain having a mutant hinge region, SCC hinge, and P238S and P331S mutations. In yet another embodiment, the Fc domain further includes a mutation at a site of N-linked glycosylation, such as a substitution at N297 (numbering by Kabat).

In some embodiments, the optimized binuclease fusion protein further includes a first linker domain, and the first nuclease domain is operably coupled to the second nuclease domain, via the first linker domain.

In some embodiments, the optimized binuclease fusion protein further includes a second linker domain, and the second nuclease domain is operably coupled to Fc domain, via the second linker domain.

In some embodiments, the RNase domain is a wild-type RNase, such as wild-type human RNase1. In other embodiments, the RNase domain is a mutant RNase, such as an aglycosylated, underglycosylated, or deglycosylated RNase 1, such as human RNase1 N34S/N76S/N88S (SEQ ID NO: 28). In some embodiments, the RNase containing optimized binuclease fusion protein degrades circulating RNA and RNA in immune complexes, or inhibits interferon-alpha production, or both. In yet other embodiments, the activity of the RNase is not less than about 10-fold less, such as 9-fold less, 8-fold less, 7-fold less, 6-fold less, 5-fold less, 4-fold less, 3-fold less, or 2-fold less than the activity of a control RNase molecule. In yet other embodiments, the activity of the RNase is about equal to the activity of a control RNase molecule.

In some embodiments, the DNase domain is wild type DNase, such as wild type, human DNase1. In other embodiments, the DNase domain is a mutant DNase domain, such as mutant, human DNase1 A114F (SEQ ID NO: 21) or an aglycosylated, underglycosylated, or deglycosylated human DNase, such as mutant, human DNase1 N18S/N106S/A114F (SEQ ID NO: 24). In some embodiments, the DNase containing optimized binuclease fusion protein degrades circulating DNA and DNA in immune complexes, or inhibits interferon-alpha production, or both. In yet other embodiments, the activity of the DNase is not less than about 10-fold less, such as 9-fold less, 8-fold less, 7-fold less, 6-fold less, 5-fold less, 4-fold less, 3-fold less, or 2-fold less than the activity of a control DNase molecule. In yet other embodiments, the activity of the DNase is about equal to the activity of a control DNase molecule.

In some embodiments, the optimized binuclease fusion protein has a gly-ser linker separating the first and second nuclease domains, and/or the second nuclease domain from the Fc domain.

In some embodiments, the optimized binuclease fusion protein has an increased serum half-life and/or activity relative to a molecule that does not contain the Fc domain.

In some aspects, the optimized binuclease fusion protein may include the mutant, human DNase1 A114F domain set forth in SEQ ID NO: 21. In another embodiment, the optimized binuclease fusion protein may include the mutant, human DNase1 N18S/N106S/A114F domain set forth in SEQ ID NO: 24. In some embodiments, the DNase domain is mutant human DNase1 E13R/N74K/A114F/T205K (SEQ ID NO: 25). In other embodiments, the DNase domain is mutant human DNase1 E13R/N74K/A114F/T205K/N18S/N106S (SEQ ID NO: 26).

In some embodiments, DNase1 and RNase1 domains are aglycosylated, underglycosylated, or deglycosylated. In some embodiments, the DNase domain is a mutant DNase domain, such as mutant, human DNase1 and an aglycosylated, underglycosylated, or deglycosylated DNase domain, such as an aglycosylated, underglycosylated, or deglycosylated human DNase1. In one embodiment, the human DNase1 includes an alteration (e.g., a substitution) at one or more sites of N-linked glycosylation, such as N18 and N106 and at least one additional mutation selected from A114, E13, N74, T205, and combinations thereof. In another embodiment, the human DNase1 includes an alteration (e.g., a substitution) at N18, N106, or both N18 and N106 and an additional alertation (e.g., a substitution) at A114, E13, N74, T205, and combinations thereof. In yet another embodiment, the human DNase1 includes an alteration at N18, N106, A114, E13, N74 and T205, such as a substitution, e.g., N18S/N106S/A114F/E13R/N74K/T205K (SEQ ID NO: 26). In another embodiment, the optimized binuclease fusion protein with altered glycosylation includes the human, wild-type RNase1 domain set forth in SEQ ID NO: 27 In another embodiment, the optimized binuclease fusion protein with altered glycosylation includes the human, mutant RNase1 N34S/N76S/N88S domain set forth in SEQ ID NO: 28.

In some aspects, the invention provides an optimized binuclease fusion protein comprising the polypeptides having an amino acid sequence set forth in SEQ ID NOs: 1-17.

In other aspects, the optimized binuclease fusion protein have an amino acid sequence at least 90% identical or at least 95% identical to an amino acid sequence set forth in SEQ ID NOs: 1-17.

In some aspects, the optimized binuclease fusion protein comprises a polypeptide comprising a first nuclease domain, a second nuclease domain and an Fc domain, wherein the first nuclease domain is DNase1 and the second nuclease domain is RNase1, wherein the DNase1 is operably linked with or without a linker in tandem from N- to C-terminus to the RNase1, and the RNase1 is operably linked with or without a linker to the Fc region. In some aspects, the RNase 1 is operably linked to the N-terminus of the Fc domain without a linker. In some aspects, the RNase 1 is operably linked to the C-terminus of the Fc domain without a linker. In some aspects, the DNase1 is operably linked to the RNase1 via a linker. In some aspects, the polypeptide comprise an amino acid sequence set forth in SEQ ID NO: 1 or SEQ ID NO:2, or a tandem binuclease fusion protein comprising an amino acid sequence at least 90% identical to the amino acid sequence set forth in SEQ ID NO:1 or SEQ ID NO:2. In some aspects, the tamdem binuclease fusion protein is a homodimer comprising any of the foregoing polypeptides.

In some aspects, the optimized binuclease fusion protein is a heterodimer comprising a first nuclease domain, a second nuclease domain, a first Fc domain and a second Fc domain, wherein the first nuclease domain is DNase1 and the second nuclease domain is RNase1, wherein the DNase1 is operably linked with or without a linker to the N- or C-terminus of the first Fc domain, and the RNase1 is operably linked with or without a linker to the N- or C-terminus of the second Fc domain. In some aspects of the foregoing heterodimer, the DNase1 is operably linked without a linker to the N-terminus of the first Fc domain and the RNase1 is operably linked without a linker to the N-terminus of the second Fc domain.

In some aspects, the DNase1 is operably linked with a linker to the N-terminus of the first Fc domain and the RNase1 is operably linked with a linker to the N-terminus of the second Fc domain. In some aspects, the DNase1 is operably linked with a linker to the N-terminus of the first Fc domain and the RNase1 is operably linked without a linker to the C-terminus of the second Fc domain. In some aspects, the DNase1 is operably linked without a linker to the N-terminus of the first Fc domain and the RNase1 is operably linked without a linker to the C-terminus of the second Fc domain. In some aspects the DNase1 is operably linked with a linker to the N-terminus of the first Fc domain and the RNase1 is operably linked with a linker to the C-terminus of the second Fc domain. In some aspects, the DNase1 is operably linked with a linker to the C-terminus of the first Fc domain and the RNase1 is operably linked with a linker to the C-terminus of the second Fc domain. In some aspects, the DNase1 is operably linked without a linker to the C-terminus of the first Fc domain and the RNase1 is operably linked without a linker to the C-terminus of the second Fc domain. In some aspects, the DNase1 is operably linked with a linker to the C-terminus of the first Fc domain and the RNase1 is operably linked without a linker to the N-terminus of the second Fc domain. In some aspects, the DNase1 is operably linked with a linker to the C-terminus of the first Fc domain and the RNase1 is operably linked with a linker to the N-terminus of the second Fc domain.

In some aspects, the optimized binuclease fusion protein is a heterodimer comprising a first and second polypeptide sequence selected from the group consisting of:

(i) a first polypeptide comprising an amino acid sequence set forth in SEQ ID NO: 3, or a polypeptide comprising an amino acid sequence at least 90% identical to the amino acid sequence set forth in SEQ ID NO:3; and a second polypeptide comprising an amino acid sequence set forth in SEQ ID NO: 4, or a polypeptide comprising an amino acid sequence at least 90% identical to the amino acid sequence set forth in SEQ ID NO: 4, or (ii) a first polypeptide comprising an amino acid sequence set forth in SEQ ID NO: 7, or a polypeptide comprising an amino acid sequence at least 90% identical to the amino acid sequence set forth in SEQ ID NO:7; and a second polypeptide comprising an amino acid sequence set forth in SEQ ID NO: 8, or a polypeptide comprising an amino acid sequence at least 90% identical to the amino acid sequence set forth in SEQ ID NO:8, or (iii) a first polypeptide comprising an amino acid sequence set forth in SEQ ID NO:9, or a polypeptide comprising an amino acid sequence at least 90% identical to the amino acid sequence set forth in SEQ ID NO:9; and a second polypeptide comprising an amino acid sequence set forth in SEQ ID NO: 10, or a polypeptide comprising an amino acid sequence at least 90% identical to the amino acid sequence set forth in SEQ ID NO:10, or (iv) a first polypeptide comprising an amino acid sequence set forth in SEQ ID NO:11, or a polypeptide comprising an amino acid sequence at least 90% identical to the amino acid sequence set forth in SEQ ID NO:11; and a second polypeptide comprising an amino acid sequence set forth in SEQ ID NO: 12, or a polypeptide comprising an amino acid sequence at least 90% identical to the amino acid sequence set forth in SEQ ID NO:12, or (v) a first polypeptide comprising an amino acid sequence set forth in SEQ ID NO:15, or a polypeptide comprising an amino acid sequence at least 90% identical to the amino acid sequence set forth in SEQ ID NO:15; and a second polypeptide comprising an amino acid sequence set forth in SEQ ID NO:16, or a polypeptide comprising an amino acid sequence at least 90% identical to the amino acid sequence set forth in SEQ ID NO:16.

Other aspects relate to a heterodimer comprising a first nuclease domain, a second nuclease domain and a first Fc domain and a second Fc domain, wherein the first nuclease domain is DNase1 and the second nuclease domain is RNase1, wherein (i) the DNase1 is operably linked with or without a linker to the N-terminus of the first Fc domain, and the RNase1 is operably linked with or without a linker to the C-terminus of the first Fc domain, or (ii) the RNase1 is operably linked with or without a linker to the N-terminus of the first Fc domain, and the DNase1 is operably linked with or without a linker to the C-terminus of the first Fc domain.

In some aspects of the foregoing heterodimer, the DNase1 is operably linked without a linker to the N-terminus of the first Fc domain and the RNase1 is operably linked with a linker to the C-terminus of the first Fc domain. In some aspects, the DNase 1 is operably linked with a linker to the N-terminus of the first Fc domain and the RNase1 is operably linked with a without a linker to the C-terminus of the first Fc domain. In some aspects, the RNase 1 is operably linked without a linker to the N-terminus of the first Fc domain and the DNase1 is operably linked with a linker to the C-terminus of the first Fc domain. In some aspects, the RNase 1 is operably linked with a linker to the N-terminus of the first Fc domain and the DNase1 is operably linked with a linker to the C-terminus of the first Fc domain.

In some aspects, a heterodimer comprises a first and second polypeptide sequence selected from the group consisting of:

(i) a first polypeptide comprising an amino acid sequence set forth in SEQ ID NO:5, or a polypeptide comprising an amino acid sequence at least 90% identical to the amino acid sequence set forth in SEQ ID NO:5; and a second polypeptide comprising an amino acid sequence set forth in SEQ ID NO:6, or a polypeptide comprising an amino acid sequence at least 90% identical to the amino acid sequence set forth in SEQ ID NO:6, or (ii) a first polypeptide comprising an amino acid sequence set forth in SEQ ID NO:13, or a polypeptide comprising an amino acid sequence at least 90% identical to the amino acid sequence set forth in SEQ ID NO:13; and a second polypeptide comprising an amino acid sequence set forth in SEQ ID NO:14, or a polypeptide comprising an amino acid sequence at least 90% identical to the amino acid sequence set forth in SEQ ID NO:14.

In some aspects, any of the foregoing heterodimers comprise one or more CH3 mutations in the Fc domains to preferentially form heterodimers. In some aspects, the heterodimer comprises a first Fc domain comprising CH3 mutations T350V, L351Y, F405A, and Y407V, and a second Fc domain comprising CH3 mutations T350V, T366L, K392L, T394W, numbering according to the EU index.

Other aspects of the disclosure relate to compositions comprising any of the foregoing heterodimer and a pharmaceutically acceptable carrier. Nucleic acid molecules encoding the foregoing heterodimers, recombinant expression vectors and host cell transformed with the recombinant expression vectors, as well as methods of making the foregoing heterodimers are also disclosed.

Also disclosed herein is a method of making a tandem optimized binuclease fusion protein disclosed herein involving providing a host cell comprising a nucleic acid sequence that encodes the optimized binuclease fusion protein; and maintaining the host cell under conditions in which the optimized binuclease fusion protein is expressed.

Also disclosed herein is a method for treating or preventing a condition associated with an abnormal immune response by administering to a patient in need thereof an effective amount of a optimized binuclease fusion protein disclosed herein. In some embodiments, the condition is an autoimmune disease. In some embodiments, the autoimmune disease is selected from the group consisting of insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, IgG4 related disease, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, systemic lupus erythematosus (SLE), and connective tissue disease. In some embodiments, the autoimmune disease is SLE or Sjogren's syndrome.

Also disclosed herein is a method of treating SLE or Sjogren's syndrome comprising administering to a subject a optimized binuclease fusion protein containing composition in an amount effective to degrade immune complexes containing RNA, DNA or both RNA and DNA. In some aspects, the composition includes a pharmaceutically acceptable carrier and a optimized binuclease fusion protein as described herein. In other aspects, the composition includes a optimized binuclease fusion protein having an amino acid sequence set forth in SEQ ID NO: 1.

In another aspect, the invention relates to optimized binuclease fusion proteins for use in treating diseases characterized by defective clearance or processing of apoptotic cells and cell debris, such as SLE. In some embodiments, the optimized binuclease fusion protein comprises amino acid sequences set forth in SEQ ID NOs: 4 and 5.

In another aspect, the invention relates to the use of the optimized binuclease fusion proteins for manufacturing a medicament for treating diseases characterized by defective clearance or processing of apoptotic cells and cell debris, such as SLE. In some embodiments, the optimized binuclease fusion protein comprises amino acid sequences set forth in SEQ ID NOs: 5 and 6.

In another aspect, the invention relates to the use of the optimized binuclease fusion proteins for manufacturing a medicament for treating diseases characterized by defective clearance or processing of apoptotic cells and cell debris, such as SLE. In some embodiments, the optimized binuclease fusion protein comprises amino acid sequences set forth in SEQ ID NOs: 7 and 8.

In another aspect, the invention relates to the use of the optimized binuclease fusion proteins for manufacturing a medicament for treating diseases characterized by defective clearance or processing of apoptotic cells and cell debris, such as SLE. In some embodiments, the optimized binuclease fusion protein comprises amino acid sequences set forth in SEQ ID NOs: 13 and 14.

In another aspect, the invention relates to the use of the optimized binuclease fusion proteins for manufacturing a medicament for treating diseases characterized by defective clearance or processing of apoptotic cells and cell debris, such as SLE. In some embodiments, the optimized binuclease fusion protein comprises amino acid sequences set forth in SEQ ID NOs: 15 and 16.

BRIEF DESCRIPTION OF THE DRAWINGS

These and other features, aspects, and advantages of the present invention will become better understood with regard to the following description, and accompanying drawing, where.

DETAILED DESCRIPTION

Figure 1:
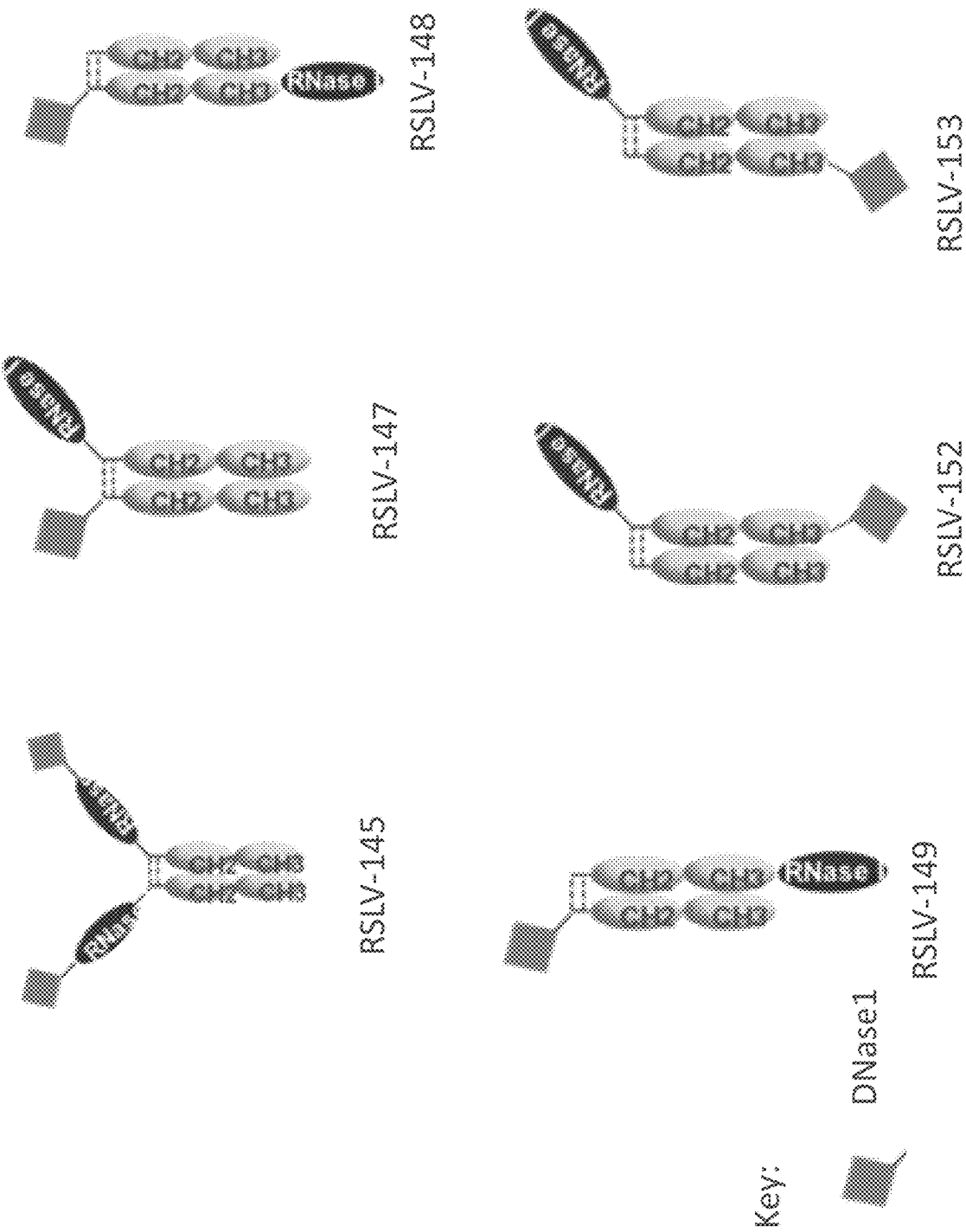
FIG. 1 is a depiction of exemplary optimized binuclease fusion proteins.

Systemic lupus erythematosus (SLE) is a multisystem autoimmune disease characterized by the presence of high titer autoantibodies directed against self nucleoproteins. There is strong evidence that defective clearance or processing of dead and dying cells in SLE leads to disease, predominantly through accumulation of ribo- and deoxyribonucleoproteins (abbreviated nucleoproteins). The nucleoproteins cause damage through three mechanisms: i) activation of the innate immune system to produce inflammatory cytokines; ii) serve as antigens to generate circulating immune complexes; and iii) serve as antigens to generate in situ complex formation at local sites such as the kidney.

The present invention provides methods for treating diseases characterized by defective clearance or processing of apoptotic cells and cell debris, such as SLE and Sjogren's syndrome, by administering an effective amount of a long-acting nuclease activity to degrade extracellular RNA and DNA containing immune complexes. Such treatment can inhibit production of Type I interferons (IFNs) which are prominent cytokines in SLE and are strongly correlated with disease activity and nephritis.

The present invention relates, in part, to the provision of such long-acting nucleases. In particular, the invention relates to an optimized binuclease fusion protein, such as a tandem binuclease fusion protein comprising a first nuclease domain, a second nuclease domain and an Fc region, wherein the first nuclease domain is DNase1 and the second nuclease domain is RNase1, wherein the DNase1 is operably linked with or without a linker in tandem from N- to C-terminus to the RNase1, and the RNase1 is operably linked to the N- or C-terminus of an Fc region.

In other embodiments, the invention relates to an optimized binuclease fusion protein, such as a heterodimeric binuclease fusion protein comprising a first nuclease domain, a second nuclease domain and an Fc region, wherein the first nuclease domain is DNase1 and the second nuclease domain is RNase1, wherein the DNase1 is operably linked with or without a linker to the N- or C-terminus of an Fc region, and the RNase1 is operably linked with or without a linker to the N- or C-terminus of an Fc region, thereby forming a heterodimer.

In some aspects, the optimized binuclease fusion protein exhibits enhanced pharmacokinetic activity relative to the either first or second nuclease domain alone. Such optimized binuclease fusion proteins exhibit altered, e.g., improved, serum half-life relative to either the first or second nuclease domain alone.

In some aspects, the invention provides a optimized binuclease fusion protein comprising human DNase1, human RNase1, and a mutant human IgG1 Fc, wherein the human DNase1 is operably linked via a linker (e.g., a gly-ser linker) to human RNase1, from N-terminus to C terminus, and wherein the human RNase1 is operably linked via a linker to the mutant human IgG1 Fc domain wherein the mutant human IgG1 has a mutant hinge region (e.g., a cysteine substitution, such as with serine, e.g., SCC), and one or more CH2 mutations to reduce Fcγ receptor binding (e.g., P238S, P331S or both P238S and P331S, numbering according to EU index). In one embodiment, the optimized binuclease fusion protein comprises human DNase1 operably linked via a peptide linker (e.g., a gly-ser linker) to human RNase1 (N-terminus-DNase1-linker-RNase1-C terminus) and the human RNase1 is operably linked via a peptide linker (e.g., a gly-ser linker) to a mutant human IgG1 Fc domain having a mutant hinge region, SCC hinge, and P238S and P331S mutations.

Accordingly, in one embodiment, a subject with a disease characterized by defective clearance or processing of apoptotic cells and cell debris is treated by administering a optimized binuclease fusion protein, which includes both DNase1 and RNase1, such that the optimized binuclease fusion protein has increased bioavailability and/or serum half-life relative to the non-conjugated nuclease domains.

Definitions

Terms used in the claims and specification are defined as set forth below unless otherwise specified.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions" can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res* 1991; 19:5081; Ohtsuka et al., *JBC* 1985; 260: 2605-8); Rossolini et al., *Mol Cell Probes* 1994; 8:91-8). For arginine and leucine, modifications at the second base can also be conservative. The term nucleic acid is used interchangeably with gene, cDNA, and mRNA encoded by a gene.

Polynucleotides of the present invention can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "operably linked" or "operably coupled" refers to a juxtaposition wherein the components described are in a relationship permitting them to function in their intended manner.

As used herein, the term "glycosylation" or "glycosylated" refers to a process or result of adding sugar moieties to a molecule (e.g., an optimized binuclease fusion protein).

As used herein, the term "altered glycosylation" refers to a molecule that is aglycosylated, deglycosylated, or underglycosylated.

As used herein, "glycosylation site(s)" refers to both sites that potentially could accept a carbohydrate moiety, as well as sites within the protein on which a carbohydrate moiety has actually been attached and includes any amino acid sequence that could act as an acceptor for an oligosaccharide and/or carbohydrate.

As used herein, the term "aglycosylation" or "aglycosylated" refers to the production of a molecule (e.g., an optimized binuclease fusion protein) in an unglycosylated form (e.g., by engineering an optimized binuclease fusion protein to lack amino acid residues that serve as acceptors of glycosylation). Alternatively, the optimized binuclease fusion protein can be expressed in, e.g., *E. coli*, to produce an aglycosylated optimized binuclease fusion protein.

As used herein, the term "deglycosylation" or "deglycosylated" refers to the process or result of enzymatic removal of sugar moieties on a molecule.

As used herein, the term "underglycosylation" or "underglycosylated" refers to a molecule in which one or more carbohydrate structures that would normally be present if produced in a mammalian cell has been omitted, removed, modified, or masked.

As used herein, the term "Fc region" and "Fc domain" is the portion of a native immunoglobulin formed by the respective Fc domains (or Fc moieties) of its two heavy chains without the variable regions which bind antigen. In some embodiments, an Fc domain begins in the hinge region just upstream of the papain cleavage site and ending at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In other embodiments, an Fc domain comprises a complete Fc domain (i.e., a hinge domain, a CH2 domain, and a CH3 domain). In one embodiment, an Fc domain comprises a hinge domain (or portion thereof) fused to a CH3 domain (or portion thereof). In another embodiment, an Fc domain comprises a CH2 domain (or portion thereof) fused to a CH3 domain (or portion thereof). In another embodiment, an Fc domain consists of a CH3 domain or portion thereof. In another embodiment, an Fc domain consists of a hinge domain (or portion thereof) and a CH3 domain (or portion thereof). In another embodiment, an Fc domain consists of a CH2 domain (or portion thereof) and a CH3 domain. In another embodiment, an Fc domain consists of a hinge domain (or portion thereof) and a CH2 domain (or portion thereof). In one embodiment, an Fc domain lacks at least a portion of a CH2 domain (e.g., all or part of a CH2 domain). In one embodiment, an Fc domain of the invention comprises at least the portion of an Fc molecule known in the art to be required for FcRn binding. In one embodiment, an Fc domain of the invention comprises at least the portion of an Fc molecule known in the art to be required for Protein A binding. In one embodiment, an Fc domain of the invention comprises at least the portion of an Fc molecule known in the art to be required for protein G binding. An Fc domain herein generally refers to a polypeptide comprising all or part of the Fc domain of an immunoglobulin heavy-chain. This includes, but is not limited to, polypeptides comprising the entire CHI, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As with Fc variants and native Fc's, the term Fc domain includes molecules in monomeric or multimeric form, whether digested from whole antibody or produced by other means.

As set forth herein, it will be understood by one of ordinary skill in the art that any Fc domain may be modified such that it varies in amino acid sequence from the native Fc domain of a naturally occurring immunoglobulin molecule.

The Fc domains of an optimized binuclease fusion protein of the disclosure may be derived from different immunoglobulin molecules. For example, an Fc domain of an optimized binuclease fusion protein may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule. The wild type human IgG1 Fc domain has the amino acid sequence set forth in SEQ ID NO: 45.

As used herein, the term "serum half-life" refers to the time required for the in vivo serum optimized binuclease fusion protein concentration to decline by 50%. The shorter the serum half-life of the optimized binuclease fusion protein, the shorter time it will have to exert a therapeutic effect.

As used herein, the term "optimized binuclease fusion protein" refers to polypeptides that comprise at least two nuclease domains operably linked, with or without a linker, to an Fc domain, or a variant or fragment thereof, and nucleic acids encoding such polypeptides. In some embodiments, an optimized binuclease fusion protein is a tandem binuclease fusion protein, e.g., a one or more DNase 1 domains and one or more RNase 1 domains linked in tandem to either the N- or C-terminus of one or more Fc domain. In some embodiments, an optimized binuclease fusion protein is a heterodimeric binuclease fusion protein.

As used herein, the term "tandem binuclease fusion protein" refers to a polypeptide that comprises at least two nuclease domains linked in tandem (from N- to C-terminus) and an Fc domain, or a variant or fragment thereof, and nucleic acids encoding such polypeptides. For example, in one embodiment, a tandem binuclease fusion protein is a polypeptide comprising at least one DNase1 domain and at least one RNase1 domain operably linked in tandem to at least one Fc domain. As another example, a tandem binuclease fusion protein includes from N- to C-terminus a DNase1 domain, a first linker, an RNase1 domain, a second linker, and an Fc domain, or a variant or fragment thereof.

As used herein, the term "heterodimeric binuclease fusion protein" refers to a heterodimer comprising a first and a second polypeptide, which together comprise at least two nuclease domains and two Fc domains, variants or fragment thereof, and nucleic acids encoding such polypeptides. In some embodiments, a heterodimeric binuclease fusion protein is a heterodimer comprising at least one DNase1 domain and at least one RNase1 domain operably linked to at least one Fc domain, wherein the DNase1 domain is operably linked with or without a linker to the N- or C-terminus of a first Fc domain and an RNase1 domain is operably linked with or without a linker the N- or C-terminus of a same (first Fc domain) or a different Fc domain (second Fc domain), such that the DNase 1 domain and the RNase 1 domain are located on opposite ends (N- or C-terminus) of either the same (first Fc domain) or different Fc domain (second Fc domain). In some embodiments, the heterodimer comprises a DNase 1 domain operably linked with or without a linker to the N- or C-terminus of a first Fc domain, and a RNase 1 operably linked with or without a linker to the N- or C-terminus of the second Fc domain, such that the DNase 1 and RNase 1 domains are located at the same end (N- or C-terminus) of the heterodimer in tandem. In some embodiments, the heterodimer comprises a DNase 1 domain operably linked with or without a linker to the N-terminus of a first Fc domain, and a RNase 1 operably linked with or without a linker to the C-terminus of the first Fc domain. In some embodiments, the RNase1 is operably linked with or without a linker to the N-terminus of the first Fc domain, and the DNase1 is operably linked with or without a linker to the C-terminus of the first Fc domain.

As used herein, the term "variant" refers to a polypeptide derived from a wild-type nuclease or Fc domain and differs from the wild-type by one or more alteration(s), i.e., a substitution, insertion, and/or deletion, at one or more positions. A substitution means a replacement of an amino acid occupying a position with a different amino acid. A deletion means removal of an amino acid occupying a position. An insertion means adding 1 or more, such as 1-3 amino acids, immediately adjacent to an amino acid occupying a position. Variant polypeptides necessarily have less than 100% sequence identity or similarity with the wild-type polypeptide. In some embodiments, the variant polypeptide will have an amino acid sequence from about 75% to less than 100% amino acid sequence identity or similarity with the amino acid sequence of wild-type polypeptide, or from about 80% to less than 100%, or from about 85% to less than 100%, or from about 90% to less than 100% (e.g., 91%, 92%, 93%, 94%, 95%, 96%, 97%, 98% o, 99%) or from about 95% to less than 100%, e.g., over the length of the variant polypeptide.

In certain aspects, the optimized binuclease fusion proteins employ one or more "linker domains," such as polypeptide linkers. As used herein, the term "linker domain" refers to one or more amino acids which connect two or more peptide domains in a linear polypeptide sequence. As used herein, the term "polypeptide linker" refers to a peptide or polypeptide sequence (e.g., a synthetic peptide or polypeptide sequence) which connects two or more polypeptide domains in a linear amino acid sequence of a protein. For example, polypeptide linkers may be used to operably link a first and second nuclease domain to each other, or a first or second nuclease domain to an Fc domain. Such polypeptide linkers in some embodiments provide flexibility to the polypeptide molecule. In some embodiments the polypeptide linker is used to connect (e.g., genetically fuse) a DNase1 to an RNase1 and/or RNase1 to an Fc domain. An optimized binuclease fusion protein may include more than one linker domain or peptide linker. Various peptide linkers are known in the art.

As used herein, the term "gly-ser polypeptide linker" refers to a peptide that consists of glycine and serine residues. An exemplary gly/ser polypeptide linker comprises the amino acid sequence $(Gly_4Ser)n$. In some embodiments, n is 1 or more, such as 2 or more, 3 or more, 4 or more, 5 or more, 6 or more, 7 or more, 8 or more, 9 or more, or 10 or more (e.g., $(Gly_4Ser)10$). Another exemplary gly/ser polypeptide linker comprises the amino acid sequence Ser $(Gly_4Ser)n$. In some embodiments, n is 1 or more, such as 2 or more, 3 or more, 4 or more, 5 or more, 6 or more, 7 or more, 8 or more, 9 or more, or 10 or more (e.g., $Ser(Gly_4Ser)$ 10).

As used herein, the terms "coupled," "linked," "fused," or "fusion," are used interchangeably. These terms refer to the joining together of two more elements or components or domains, by whatever means including chemical conjugation or recombinant means. Methods of chemical conjugation (e.g., using heterobifunctional crosslinking agents) are known in the art.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

In one embodiment, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity.

In one embodiment, a polypeptide of the disclosure consists of, consists essentially of, or comprises an amino acid sequence as set forth in the Sequence Listing or Sequence Table disclosed herein and functionally active variants thereof. In an embodiment, a polypeptide includes an amino acid sequence at least 80%, such as at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence set forth in the Sequence Listing or Sequence Table disclosed herein. In some embodiments, a polypeptide includes a contiguous amino acid sequence at least 80%, such as at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a contiguous amino acid sequence set forth in the Sequence Listing or Sequence Table disclosed herein. In some embodiments, a polypeptide includes an amino acid sequence having at least 10, such as at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, or at least 500 (or any integer within these numbers) contiguous amino acids of an amino acid sequence set forth in Sequence Listing or Sequence Table disclosed herein.

In some embodiments, the optimized binuclease fusion proteins of the disclosure are encoded by a nucleotide sequence. Nucleotide sequences of the disclosure can be useful for a number of applications, including: cloning, gene therapy, protein expression and purification, mutation introduction, DNA vaccination of a host in need thereof, antibody generation for, e.g., passive immunization, PCR, primer and probe generation, siRNA design and generation (see, e.g., the Dharmacon siDesign website), and the like. In some embodiments, the nucleotide sequence of the disclosure comprises, consists of, or consists essentially of, a nucleotide sequence that encodes the amino acid sequence of the optimized binuclease fusion proteins selected from the Sequence Table or Sequence Listing. In some embodiments, a nucleotide sequence includes a nucleotide sequence at least 80%, such as at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a nucleotide sequence encoding an amino acid sequence of the Sequence Listing or Sequence Table disclosed herein. In some embodiments, a nucleotide sequence includes a contiguous nucleotide sequence at least 80%, such as at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a contiguous nucleotide sequence encoding an amino acid sequence set forth in the Sequence Listing or Sequence Table disclosed herein. In some embodiments, a nucleotide sequence includes a nucleotide sequence having at least 10, such as at least 15, such as at least 20, at least 25, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, or at least 500 (or any integer within these numbers) contiguous nucleotides of a nucleotide sequence encoding an amino acid sequence set forth in the Sequence Listing or Sequence Table disclosed herein.

It will also be understood by one of ordinary skill in the art that the optimized binuclease fusion proteins may be altered such that they vary in sequence from the naturally occurring or native sequences from which their components (e.g., nuclease domains, linker domains, and Fc domains) are derived, while retaining the desirable activity of the native sequences. For example, nucleotide or amino acid substitutions leading to conservative substitutions or changes at "non-essential" amino acid residues may be made. An isolated nucleic acid molecule encoding a non-natural variant can be created by introducing one or more nucleotide substitutions, additions or deletions into the nucleotide sequence of the optimized binuclease fusion protein such that one or more amino acid substitutions, additions or deletions are introduced into the encoded protein. Mutations may be introduced by standard techniques, such as site-directed mutagenesis and PCR-mediated mutagenesis.

The optimized binuclease fusion proteins may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan, beta-branched side chains (e.g., threonine, valine, isoleucine), and aromatic side chains (e.g., tyrosine, phenylalanine, tryptophan, histidine). Thus, a nonessential amino acid residue in an optimized binuclease fusion protein is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into the optimized binuclease fusion proteins and screened for their ability to bind to the desired target.

The term "ameliorating" refers to any therapeutically beneficial result in the treatment of a disease state, e.g., an autoimmune disease state (e.g., SLE, Sjogren's syndrome), including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism. The term "mammal" or "subject" or "patient" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv Appl Math* 1981; 2:482, by the homology alignment algorithm of Needleman & Wunsch, *J Mol Biol* 1970; 48:443, by the search for similarity method of Pearson & Lipman, *PNAS* 1988; 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al, infra).

One example of an algorithm that is suitable for determining percent sequence identity and sequence similarity is the BLAST algorithm, which is described in Altschul et al., *J Mol Biol* 1990; 215:403-10. Software for performing BLAST analyses is publicly available through the National Center for Biotechnology Information website.

The term "sufficient amount" means an amount sufficient to produce a desired effect.

The term "therapeutically effective amount" is an amount that is effective to ameliorate a symptom of a disease. A therapeutically effective amount can be a "prophylactically effective amount" as prophylaxis can be considered therapy.

The term "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

It must be noted that, as used in the specification and the appended claims, the singular forms "a," "an" and "the" include plural referents unless the context clearly dictates otherwise.

Optimized Binuclease Fusion Proteins

The optimized binuclease fusion proteins of the disclosure include an Fc domain, or a variant or fragment thereof, that alters the serum half-life of the nuclease molecules to which it is fused compared to nuclease molecules that are not fused to the Fc domain, or a variant or fragment thereof.

In some embodiments, a composition of the disclosure includes an optimized binuclease fusion protein. In some embodiments, an optimized binuclease fusion protein includes a nuclease domain operably coupled to an Fc domain, or a variant or fragment thereof.

In some embodiments, the nuclease domain is operably coupled to the Fc domain, or a variant or fragment thereof, via a linker domain. In some embodiments, the linker domain is a linker peptide. In some embodiments, the linker domain is a linker nucleotide.

In some embodiments, the optimized binuclease fusion protein includes a leader molecule, e.g., a leader peptide. In some embodiments, the leader molecule is a leader peptide positioned at the N-terminus of the nuclease domain. In some embodiments, an optimized binuclease fusion protein of the invention comprises a leader peptide at the N-terminus of the molecule, wherein the leader peptide is later cleaved from the optimized binuclease fusion protein. Methods for generating nucleic acid sequences encoding a leader peptide fused to a recombinant protein are well known in the art. In some embodiments, any of the optimized binuclease fusion proteins of the present invention can be expressed either with or without a leader fused to their N-terminus. The protein sequence of an optimized binuclease fusion protein of the present disclosure following cleavage of a fused leader peptide can be predicted and/or deduced by one of skill in the art.

In some embodiments the leader is a VK3 leader peptide (VK3LP), wherein the leader peptide is fused to the N-terminus of the optimized binuclease fusion protein. Such leader sequences can improve the level of synthesis and secretion of the optimized binuclease fusion protein in mammalian cells. In some embodiments, the leader is cleaved, yielding optimized binuclease fusion proteins. In some embodiments, an optimized binuclease fusion protein of the present invention is expressed without a leader peptide fused to its N-terminus, and the resulting optimized binuclease fusion protein has an N-terminal methionine.

In some embodiments, the optimized binuclease fusion protein includes two nuclease domains operably coupled to each other in tandem and further operably coupled to the N- or C-terminus of the same or different Fc domains, or a variant or fragment thereof.

FIG. 1 displays exemplary configurations of the optimized binuclease fusion proteins, and the Sequence Table provides the sequences of exemplary optimized binuclease fusion proteins of various configurations.

In some embodiments, an optimized binuclease fusion protein is a multi-nuclease protein (e.g., both RNase and DNase or two RNA or DNA nucleases with different specificity for substrate) fused to the same or different Fc domains, or a variant or fragment thereof, that specifically binds to extracellular immune complexes.

In one embodiment, the nuclease domain is operably coupled (e.g., chemically conjugated or genetically fused (e.g., either directly or via a polypeptide linker)) to the N-terminus of a Fc domain, or a variant or fragment thereof. In another embodiment, the nuclease domain is operably coupled (e.g., chemically conjugated or genetically fused (e.g., either directly or via a polypeptide linker)) to the C-terminus of a Fc domain, or a variant or fragment thereof. In other embodiments, a nuclease domain is operably coupled (e.g., chemically conjugated or genetically fused (e.g., either directly or via a polypeptide linker)) via an amino acid side chain of a Fc domain, or a variant or fragment thereof.

In certain embodiments, the optimized binuclease fusion proteins of the disclosure comprise two or more nuclease domains and at least one Fc domain, or a variant or fragment thereof. For example, nuclease domains may be operably coupled to both the N-terminus and C-terminus of the same or different Fc domains, or variants or fragments thereof, with optional linkers between the nuclease domains and the Fc domain(s), variant(s) or fragment(s) thereof. In some embodiments, the nuclease domains are identical, e.g., RNase and RNase, or DNase1 and DNase1. In other embodiments, the nuclease domains are different, e.g., DNase and RNase.

In some embodiments, two or more nuclease domains are operably coupled to each other (e.g., via a polypeptide linker) in series, and the tandem array of nuclease domains is operably coupled (e.g., chemically conjugated or genetically fused (e.g., either directly or via a polypeptide linker)) to either the C-terminus or the N-terminus of the same or different Fc domains, or variants or fragments thereof. In other embodiments, the tandem array of nuclease domains is operably coupled to both the N-terminus and the C-terminus of the same Fc domain, or a variant or fragment thereof. In some embodiments, the nuclease domains are operably linked in tandem (e.g., N-DNase-RNase-C or N-RNase-DNase-C) with or without a linker to the N- or C-terminus of the same or different Fc domains. In some embodiments, the tandem binuclease fusion proteins form a homodimer or a heterodimer.

In other embodiments, one or more nuclease domains may be inserted between two Fc domains, or variants or fragments thereof. For example, one or more nuclease domains may form all or part of a polypeptide linker of a optimized binuclease fusion protein of the disclosure.

In some embodiments, the optimized binuclease fusion proteins comprise at least two nuclease domains (e.g., RNase and DNase), at least one linker domain, and at least one Fc domain, or a variant or fragment thereof.

In some embodiments, the optimized binuclease fusion proteins of the disclosure comprise a Fc domain, or a variant or fragment thereof, as described supra, thereby increasing serum half-life and bioavailability of the optimized binuclease fusion proteins.

In some embodiments, an optimized binuclease fusion protein comprises one or more polypeptides such as a polypeptide comprising an amino acid sequence as shown in any of SEQ ID NOs: 1-17.

It will be understood by the skilled artisan that other configurations of the nuclease domains and Fc domains are possible, with the inclusion of optional linkers between the nuclease domains and/or between the nuclease domains and Fc domain. It will also be understood that domain orientation can be altered, so long as the nuclease domains are active in the particular configuration tested.

In certain embodiments, the optimized binuclease fusion proteins of the disclosure have at least one nuclease domain specific for a target molecule which mediates a biological effect. In another embodiment, binding of the optimized binuclease fusion proteins of the disclosure to a target molecule (e.g. DNA or RNA) results in the reduction or elimination of the target molecule, e.g., from a cell, a tissue, or from circulation.

In other embodiments, the optimized binuclease fusion proteins of the disclosure may be assembled together or with other polypeptides to form binding proteins having two or more polypeptides ("multimers"), wherein at least one polypeptide of the multimer is an optimized binuclease fusion protein of the invention. Exemplary multimeric forms include dimeric, trimeric, tetrameric, and hexameric altered binding proteins and the like. In one embodiment, the polypeptides of the multimer are the same (i.e., homomeric altered binding proteins, e.g., homodimers, homotetramers). In another embodiment, the polypeptides of the multimer are different (e.g., heteromeric).

In some embodiments, an optimized binuclease fusion protein has a serum half-life that is increased at least about 1.5-fold, such as at least 3-fold, at least 5-fold, at least 10-fold, at least about 20-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1000-fold, or 1000-fold or greater relative to the corresponding nuclease molecules not fused to the Fc domain, or a variant or fragment thereof. In other embodiments, an optimized binuclease fusion protein has a serum half-life that is decreased at least about 1.5-fold, such as at least 3-fold, at least 5-fold, at least 10-fold, at least about 20-fold, at least about 50-fold, at least about 100-fold, at least about 200-fold, at least about 300-fold, at least about 400-fold, at least about 500-fold, or 500-fold or lower relative to the corresponding nuclease molecules not fused to the Fc domain, or a variant or fragment thereof. Routine art-recognized methods can be used to determine the serum half-life of optimized binuclease fusion proteins of the disclosure.

In some embodiments, the activity of the RNase in the optimized binuclease fusion protein is not less than about 10-fold less, such as 9-fold less, 8-fold less, 7-fold less, 6-fold less, 5-fold less, 4-fold less, 3-fold less, or 2-fold less than the activity of a control RNase molecule. In some embodiments, the activity of the RNase in the optimized binuclease fusion protein is about equal to the activity of a control RNase molecule.

In some embodiments, the activity of the DNase in the optimized binuclease fusion protein is not less than about 10-fold less, such as 9-fold less, 8-fold less, 7-fold less, 6-fold less, 5-fold less, 4-fold less, 3-fold less, or 2-fold less than the activity of a control DNase molecule. In some embodiments, the activity of the DNase in the optimized binuclease fusion protein is about equal to the activity of a control DNase molecule.

In some embodiments, the optimized binuclease fusion proteins can be active towards extracellular immune complexes containing DNA and/or RNA, e.g., either in soluble form or deposited as insoluble complexes.

In some embodiments, the activity of the optimized binuclease fusion protein is detectable in vitro and/or in vivo. In some embodiments, the optimized binuclease fusion protein binds to a cell, a malignant cell, or a cancer cell and interferes with its biologic activity.

In another aspect, a multifunctional RNase or DNase molecule is provided that is attached to another enzyme or antibody having binding specificity, such as an scFv targeted to RNA or DNA or a second nuclease domain with the same or different specificities as the first domain.

In some embodiments, linker domains include (gly4ser) 3, 4 or 5 variants that alter the length of the linker by 5 amino acid progressions. In another embodiment, a linker domain is approximately 18 amino acids in length and includes an N-linked glycosylation site, which can be sensitive to protease cleavage in vivo. In some embodiments, an N-linked glycosylation site can protect the optimized binuclease fusion proteins from cleavage in the linker domain. In some embodiments, an N-linked glycosylation site can assist in separating the folding of independent functional domains separated by the linker domain.

In some embodiments, the linker domain is an NLG linker (VDGASSPVNVSSPSVQDI) (SEQ ID NO: 41).

In some embodiments, the optimized binuclease fusion protein includes substantially all or at least an enzymatically active fragment of a DNase. In some embodiments, the DNase is a Type I secreted DNase, preferably a human DNase such as mature human pancreatic DNase 1 (UniProtKB entry P24855, SEQ ID NO: 20). In some embodiments, a naturally occurring variant allele, A114F (SEQ ID NO: 21), which shows reduced sensitivity to actin is included in a DNase1 optimized binuclease fusion protein (see Pan et al., JBC 1998; 273:18374-81; Zhen et al., BBRC 1997; 231:499-504; Rodriguez et al., Genomics 1997; 42:507-13). In other embodiments, a naturally occurring variant allele, G105R (SEQ ID NO: 22), which exhibits high DNase activity relative to wild type DNase1, is included in a DNase1 optimized binuclease fusion protein (see Yasuda et al., Int J Biochem Cell Biol 2010; 42:1216-25). In some embodiments, this mutation is introduced into an optimized binuclease fusion protein to generate a more stable derivative of human DNase1. In some embodiments, the DNase is human, wild type DNase1 or human, DNase1 A114F mutated to remove all potential N-linked glycosylation sites, i.e., asparagine residues at positions 18 and 106 of the DNase1 domain set forth in SEQ ID NO: 20 (i.e., human DNase1 N18S/N106S/A114F, SEQ ID NO: 24), which correspond to asparagine residues at positions 40 and 128, respectively, of full length pancreatic DNase1 with the native leader (SEQ ID NO: 23). In some embodiments, the DNase is a human DNase1 comprising one or more basic (i.e., positively charged) amino acid substitutions to increase DNase functionality and chromatin cleavage. In some embodiments, basic amino acids are introduced into human DNase1 at the DNA binding interface to enhance binding with negatively charged phosphates on DNA substrates (see U.S. Pat. Nos. 7,407,785; 6,391,607). This hyperactive DNase1 may be referred to as "chromatin cutter."

In some embodiments, 1, 2, 3, 4, 5 or 6 basic amino acid substitutions are introduced into DNase1. For example, one or more of the following residues is mutated to enhance DNA binding: Gln9, Glu13, Thr14, His44, Asn74, Asn110, Thr205. In some embodiments one or more of the foregoing amino acids are substituted with basic amino acids such as, arginine, lysine and/or histidine. For example, a mutant human DNase can include one or more of the following substitutions: Q9R, E13R, T14K, H44K, N74K, N110R, T205K. In some embodiments, the mutant human DNase1 also includes an A114F substitution, which reduces sensitivity to actin (see U.S. Pat. No. 6,348,343). In one embodiment, the mutant human DNase1 includes the following substitutions: E13R, N74K, A114F and T205K.

In some embodiments, the mutant human DNase1 further includes mutations to remove potential glycosylation sites, e.g., asparagine residues at positions 18 and 106 of the DNase1 domain set forth in SEQ ID NO: 20, which correspond to asparagines residues at positions 40 and 128, respectively of full length pancreatic DNase1 with the native leader. In one embodiment, the mutant human DNase1 includes the following substitutions: E13R/N74K/A114F/T205K/N18SN106S.

In some embodiments, the DNase is DNase 1-like (DNaseL) enzyme, 1-3 (UniProtKB entry Q13609; SEQ ID NO: 46). In some embodiments, the DNase is three prime repair exonuclease 1 (TREX1; UniProtKB entry Q9NSU2; SEQ ID NO: 47). In some embodiments, the DNase is DNase2. In some embodiments, the DNase2 is DNAse2 alpha (i.e., DNase2; UnitProtKB entry O00115SEQ ID NO: 48) or DNase2 beta (i.e., DNase2-like acid DNase; UnitProtKB entry Q8WZ79; SEQ ID NO: 49). In some embodiments, the N-linked glycosylation sites of DNase 1L3, TREX1, DNase2 alpha, or DNase2 beta are mutated such as to remove potential N-linked glycosylation sites. In some embodiments, a DNase-linker-Fc domain containing a 20 or 25 aa linker domain is made.

In some embodiments, the optimized binuclease fusion protein includes a RNase1, preferably human pancreatic RNase1 (UniProtKB entry P07998; SEQ ID NO: 27) of the RNase A family. In some embodiments, the human RNase1 is mutated to remove all potential N-linked glycosylation sites, i.e., asparagine residues at positions 34, 76, and 88 of the RNase1 domain set forth in SEQ ID NO: 27 (human RNase1 N34S/N76SN88S, SEQ ID NO: 28), which correspond to asparagine residues at positions 62, 104, and 116, respectively, of full length pancreatic RNase1 with the native leader (SEQ ID NO: 29). In some embodiments, a RNase1-linker-Fc containing a 20 or 25 aa linker domain is made.

In some embodiments, optimized binuclease fusion proteins include DNase-linker-RNase-Fc, wherein the RNase1 domain is located at the COOH side of the Fc. In other embodiments, optimized binuclease fusion proteins include DNase-linker-RNase-Fc, wherein the RNase1 domain is located at the NH2 side of the Fc. In some embodiments, optimized binuclease fusion proteins include: DNase-Fc and RNase-Fc; DNase1-Fc-linker-RNase and Fc domain; DNase1-Fc and Fc-linker-RNase; Fc-linker-DNase1 and Fc-linker-RNase; RNase-Fc-linker-DNase and Fc domain; Fc-linker-DNase and Rnase-Fc; and RNase-Fc-linker-DNase.

In some embodiments, fusion junctions between enzyme domains and the other domains of the optimized binuclease fusion protein is optimized.

In some embodiments, the targets of the RNase enzyme activity of optimized binuclease fusion proteins are primarily extracellular, consisting of, e.g., RNA contained in immune complexes with anti-RNP autoantibody and RNA expressed on the surface of cells undergoing apoptosis. In some embodiments, the optimized binuclease fusion protein is active in the acidic environment of the endocytic vesicles. In some embodiments, an optimized binuclease fusion protein including a Fc domain, or a variant or fragment thereof, is adapted to be active both extracellularly and in the endocytic environment. In some aspects, this allows an optimized binuclease fusion protein including a wild-type Fc domain, or a variant or fragment thereof, to stop TLR7 signaling through previously engulfed immune complexes or by RNAs that activate TLR7 after viral infection. In some embodiments, the wild type RNase of an optimized binuclease fusion protein is not resistant to inhibition by an RNase cytoplasmic inhibitor. In some embodiments, the wild type RNase of an optimized binuclease fusion protein is not active in the cytoplasm of a cell.

In some embodiments, optimized binuclease fusion proteins include both DNase and RNase. In some embodiments, these optimized binuclease fusion proteins improve therapy of SLE because they digest or degrade immune complexes containing RNA, DNA, or a combination of both RNA and DNA, and are active extracellularly.

Fc Domain

In some embodiments, the polypeptide comprising one or more nuclease domains is operably coupled to a Fc domain, which serves as a scaffold as well as a means to increase the serum half-life of the polypeptide. In some embodiments, the one or more nuclease domains and/or the Fc domain is aglycosylated, deglycosylated, or underglycosylated.

Suitable Fc domains are well-known in the art and include, but are not limited to, Fc and Fc variants, such as those disclosed in WO2011/053982, WO 02/060955, WO 02/096948, WO05/047327, WO05/018572, and US 2007/0111281 (the contents of the foregoing are incorporated herein by reference). It is within the abilities of the skilled artisan to use routine methods to introduce Fc domains (e.g., cloning, conjugation) into the optimized binuclease fusion proteins disclosed herein (with or without altered glycosylation).

In some embodiments, the Fc domain is a wild type human IgG1 Fc, such as is shown in SEQ ID NO: 45.

In some embodiments, an Fc domain is altered or modified, e.g., by mutation which results in an amino acid addition, deletion, or substitution. As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region. The amino acid substitution(s) of an Fc variant may be located at a position within the Fc domain referred to as corresponding to the position number that that residue would be given in an Fc region in an antibody (numbering according to EU index).

In one embodiment, the Fc variant comprises one or more amino acid substitutions at an amino acid position(s) located in a hinge region or portion thereof. In another embodiment, the Fc variant comprises one or more amino acid substitutions at an amino acid position(s) located in a CH2 domain or portion thereof. In another embodiment, the Fc variant comprises one or more amino acid substitutions at an amino acid position(s) located in a CH3 domain or portion thereof. In another embodiment, the Fc variant comprises one or more amino acid substitutions at an amino acid position(s) located in a CH4 domain or portion thereof.

In some embodiments, the Fc region has a mutation at N83 (i.e., N297 by Kabat numbering), yielding an aglycosylated Fc region (e.g., Fc N83S; SEQ ID NO: 50). In some embodiments, the Fc domain includes mutations in one or more of the three hinge region cysteines (residues 220, 226, and 229, numbering according to the EU index). In some embodiments, one or more of the three hinge cysteines in the Fc domain can be mutated to SCC (SEQ ID NO: 51) or SSS (SEQ ID NO: 52), where in "S" represents an amino acid substitution of cysteine with serine. Accordingly "SCC" indicates an amino acid substitution to serine of only the first cysteine of the three hinge region cysteines (residues 220, 226, and 229, numbering according to the EU index), whereas "SSS" indicates that all three cysteines in the hinge region are substituted with serine (residues 220, 226, and 229, numbering according to the EU index).

In some aspects, the Fc domain is a mutant human IgG1 Fc domain. In some aspects, a mutant Fc domain comprises one or more mutations in the hinge, CH2, and/or CH3 domains.

CH2 Substitutions

In some aspects, a mutant Fc domain includes a P238S mutation. In some aspects, a mutant Fc domain includes a P331S mutation. In some aspects, a mutant Fc domain includes a P238S mutation and a P331S mutation. In some aspects, a mutant Fc domain comprises P238S and/or P331S, and may include mutations in one or more of the three hinge cysteines (residues 220, 226, and 229), numbering according to the EU index. In some aspects, a mutant Fc domain comprises P238S and/or P331S, and/or one or more mutations in the three hinge cysteines (residues 220, 226, and 229), numbering according to the EU index. In some aspects, a mutant Fc domain comprises P238S and/or P331S, and/or mutations in a hinge cysteine to SCC or in the three hinge cysteines to SSS. In some aspects, a mutant Fc domain comprises P238S and P331S and mutations in at least one of the three hinge cysteines. In some aspects, a mutant Fc domain comprises P238S and P331S and SCC. In some aspects, a mutant Fc domain comprises P238S and P331S and SSS. In some aspects, a mutant Fc domain includes P238S and SCC or SSS. In some aspects, a mutant Fc domain includes P331S and SCC or SSS. (All numbering according to the EU index).

In some aspects, a mutant Fc domain includes a mutation at a site of N-linked glycosylation, such as N297, e.g., a substitution of asparagine for another amino acid such as serine, e.g., N297S. In some aspects, a mutant Fc domain includes a mutation at a site of N-linked glycosylation, such as N297, e.g., a substitution of asparagine for another amino acid such as serine, e.g., N297S and a mutation in one or more of the three hinge cysteines. In some aspects, a mutant Fc domain includes a mutation at a site of N-linked glycosylation, such as N297, e.g., a substitution of asparagine for another amino acid such as serine, e.g., N297S and mutations in one of the three hinge cysteines to SCC or all three cysteines to SSS. In some aspects, a mutant Fc domain includes a mutation at a site of N-linked glycosylation, such as N297, e.g., a substitution of asparagine for another amino acid such as serine, e.g., N297 and one or more mutations in the CH2 domain which decrease FcγR binding and/or complement activation, such as mutations at P238 or P331 or both, e.g., P238S or P331S or both P238S and P331S. In some aspects, such mutant Fc domains can further include a mutation in the hinge region, e.g., SCC or SSS. (All numbering according to the EU index.) In some aspects, the mutant Fc domain is as shown in the Sequence Table or Sequence Listing herein.

CH3 Substitutions

Heterodimers can be preferentially formed by mutations in the CH3 domain of the Fc domain on the heterodimeric binuclease fusion proteins disclosed herein. Heavy chains were first engineered for heterodimerization using a "knobs-into-holes" strategy (Rigway B, et al., Protein Eng., 9 (1996) pp. 617-621). The term "knob-into-hole" refers to the technology directing the pairing of two polypeptides together in vitro or in vivo by introducing a pertuberance (knob) into one polypeptide and a cavity (hole) into the other polypeptide at an interface in which they interact. See e.g., WO 96/027011, WO 98/050431, U.S. Pat. No. 5,731,168, US2007/0178552, WO2009089004, US 20090182127. In particular, a combination of mutations in the CH3 domain can be used to preferentially form heterodimers, for example, S354C, T366W in the "knob" heavy chain, and Y349C, T366S, L368A, Y407V in the "hole" heavy chain. In some embodiments, the heterodimeric binuclease fusion protein disclosed herein includes a first CH3 domain having the knob mutation T366W and a second CH3 domain having the hole mutations T366S, L368A, and Y407V. (Numbering according to the EU index.)

In some embodiments, the CH3 mutations are those described by Zymeworks (US 2012/0149876 A1, incorporated herein by reference; and Von Kreudenstein, T. S. et al. mABs, 5 (2013); pp. 646-654) and include the following mutations: T350V, L351Y, F405A, and Y407V (first CH3 domain); and T350V, T366L, K392L, T394W (second CH3 domain). In some embodiments, the heterodimeric binuclease fusion protein disclosed herein includes a first CH3 domain having T350V, L351Y, F405A, and Y407V mutations and a second CH3 domain having T350V, T366L, K392L, T394W mutations. (Numbering according to the EU index.)

In some embodiments, the CH3 mutations are those described by Moore, G. L. et al. (mABs, 3 (2011), pp. 546-557) and include the following mutations: S364H and F405A (first CH3 domain); and Y349T and T394F (second CH3 domain). In some embodiments, the heterodimeric binuclease fusion protein disclosed herein includes a first CH3 domain having S364H and F405A mutations and a second CH3 domain having Y349T and T394F mutations. (Numbering according to the EU index.)

In some embodiments, the CH3 mutations are those described by Gunasekaran, K. et al. (J. Biol. Chem., 285 (2010), pp. 1963749646) and include the following mutations: K409D and K392D (first CH3 domain); and D399K and E365K (second CH3 domain). In some embodiments, the heterodimeric binuclease fusion protein disclosed herein includes a first CH3 domain having K409D and K392D mutations and a second CH3 domain having D399K and E365K mutations. (Numbering according to the EU index.)

The optimized binuclease fusion proteins of the disclosure may employ art-recognized Fc variants which are known to impart an alteration in effector function and/or FcR binding. For example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351 A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

Other amino acid mutations in the Fc domain are contemplated to reduce binding to the Fc gamma receptor and Fc gamma receptor subtypes. The assignment of amino acids residue numbers to an Fc domain is in accordance with the definitions of Kabat. See, e.g., *Sequences of Proteins of Immunological Interest* (Table of Contents, Introduction and Constant Region Sequences sections), 5th edition, Bethesda, Md.:NIH vol. 1:647-723 (1991); Kabat et al., "Introduction" *Sequences of Proteins of Immunological Interest*, US Dept of Health and Human Services, NIH, 5th edition, Bethesda, Md. vol. 1:xiii-xcvi (1991); Chothia & Lesk, *J. Mol. Biol.* 196:901-917 (1987); Chothia et al., *Nature* 342:878-883 (1989), each of which is herein incorporated by reference for all purposes."

For example, mutations at positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 322, 324, 327, 329, 330, 331, 333, 334, 335, 337, 338, 340, 356, 360, 373, 376, 378, 379, 382, 388, 389, 398, 414, 416, 419, 430, 434, 435, 437, 438 or 439 of the Fc region can alter binding as described in U.S. Pat. No. 6,737,056, issued May 18, 2004, incorporated herein by reference in its entirety. This patent reported that changing Pro331 in IgG3 to Ser resulted in six fold lower affinity as compared to unmutated IgG3, indicating the involvement of Pro331 in Fc gamma RI binding. In addition, amino acid modifications at positions 234, 235, 236, and 237, 297, 318, 320 and 322 are disclosed as potentially altering receptor binding affinity in U.S. Pat. No. 5,624,821, issued Apr. 29, 1997 and incorporated herein by reference in its entirety. (Numbering according to the EU index.)

Further mutations contemplated for use include, e.g., those described in U.S. Pat. App. Pub. No. 2006/0235208, published Oct. 19, 2006 and incorporated herein by reference in its entirety. This publications describe Fc variants that exhibit reduced binding to Fc gamma receptors, reduced antibody dependent cell-mediated cytotoxicity, or reduced complement dependent cytotoxicity, that comprise at least one amino acid modification in the Fc region, including 232G, 234G, 234H, 235D, 235G, 235H, 236I, 236N, 236P, 236R, 237K, 237L, 237N, 237P, 238K, 239R, 265G, 267R, 269R, 270H, 297S, 299A, 299I, 299V, 325A, 325L, 327R, 328R, 329K, 330I, 330L, 330N, 330P, 330R, and 331L (numbering is according to the EU index), as well as double mutants 236R/237K, 236R/325L, 236R/328R, 237K/325L, 237K/328R, 325L/328R, 235G/236R, 267R/269R, 234G/235G, 236R/237K/325L, 236R/325L/328R, 235G/236R/237K, and 237K/325L/328R. Other mutations contemplated for use as described in this publication include 227G, 234D, 234E, 234G, 234I, 234Y, 235D, 235I, 235S, 236S, 239D, 246H, 255Y, 258H, 260H, 264I, 267D, 267E, 268D, 268E, 272H, 272I, 272R, 281D, 282G, 283H, 284E, 293R, 295E, 304T, 324G, 324I, 327D, 327A, 328A, 328D, 328E, 328F, 328I, 328M, 328N, 328Q, 328T, 328V, 328Y, 330I, 330L, 330Y, 332D, 332E, 335D, an insertion of G between positions 235 and 236, an insertion of A between positions 235 and 236, an insertion of S between positions 235 and 236, an insertion of T between positions 235 and 236, an insertion of N between positions 235 and 236, an insertion of D between positions 235 and 236, an insertion of V between positions 235 and 236, an insertion of L between positions 235 and 236, an insertion of G between positions 235 and 236, an insertion of A between positions 235 and 236, an insertion of S between positions 235 and 236, an insertion of T between positions 235 and 236, an insertion of N between positions 235 and 236, an insertion of D between positions 235 and 236, an insertion of V between positions 235 and 236, an insertion of L between positions 235 and 236, an insertion of G between positions 297 and 298, an insertion of A between positions 297 and 298, an insertion of S between positions 297 and 298, an insertion of D between positions 297 and 298, an insertion of G between positions 326 and 327, an insertion of A between positions 326 and 327, an insertion of T between positions 326 and 327, an insertion of D between positions 326 and 327, and an insertion of E between positions 326 and 327 (numbering is according to the EU index). Additionally, mutations described in U.S. Pat. App. Pub. No. 2006/0235208 include 227G/332E, 234D/332E, 234E/332E, 234Y/332E, 234I/332E, 234G/332E, 235I/332E, 235S/332E, 235D/332E, 235E/332E, 236S/332E, 236A/332E, 236S/332D, 236A/332D, 239D/268E, 246H/332E, 255Y/332E, 258H/332E, 260H/332E, 264I/332E, 267E/332E, 267D/332E, 268D/332D, 268E/332D, 268E/332E, 268D/332E, 268E/330Y, 268D/330Y, 272R/332E, 272H/332E, 283H/332E, 284E/332E, 293R/332E, 295E/332E, 304T/332E, 324I/332E, 324G/332E, 324I/332D, 324G/332D, 327D/332E, 328A/332E, 328T/332E, 328V/332E, 328I/332E, 328F/332E, 328Y/332E, 328M/332E, 328D/332E, 328E/332E, 328N/332E, 328Q/332E, 328A/332D, 328T/332D, 328V/332D, 328I/332D, 328F/332D, 328Y/332D, 328M/332D, 328D/332D, 328E/332D, 328N/332D, 328Q/332D, 330L/332E, 330Y/332E, 330I/332E, 332D/330Y, 335D/332E, 239D/332E, 239D/332E/330Y, 239D/332E/330L, 239D/332E/330I, 239D/332E/268E, 239D/332E/268D, 239D/332E/327D, 239D/332E/284E, 239D/268E/330Y, 239D/332E/268E/330Y, 239D/332E/327A, 239D/332E/268E/327A, 239D/332E/330Y/327A, 332E/330Y/268 E/327A, 239D/332E/268E/330Y/327A, Insert G>297-298/332E, Insert A>297-298/332E, Insert S>297-298/332E, Insert D>297-298/332E, Insert G>326-327/332E, Insert A>326-327/332E, Insert T>326-327/332E, Insert D>326-327/332E, Insert E>326-327/332E, Insert G>235-236/332E, Insert A>235-236/332E, Insert S>235-236/332E, Insert T>235-236/332E, Insert N>235-236/332E, Insert D>235-236/332E, Insert V>235-236/332E, Insert L>235-236/332E, Insert G>235-236/332D, Insert A>235-236/332D, Insert S>235-236/332D, Insert T>235-236/332D, Insert N>235-236/332D, Insert D>235-236/332D, Insert V>235-236/332D, and Insert L>235-236/332D (numbering according to the EU index) are contemplated for use. The mutant L234A/L235A is described, e.g., in U.S. Pat. App. Pub. No. 2003/0108548, published Jun. 12, 2003 and incorporated herein by reference in its entirety. In embodiments, the described modifications are included either individually or in combination. (Numbering according to the EU index.)

Linker Domains

In some embodiments, an optimized binuclease fusion protein includes a linker domain. In some embodiments, an optimized binuclease fusion protein includes a plurality of linker domains. In some embodiments, the linker domain is a polypeptide linker. In certain aspects, it is desirable to employ a polypeptide linker to fuse Fc, or a variant or fragment thereof, with one or more nuclease domains to form an optimized binuclease fusion protein.

In one embodiment, the polypeptide linker is synthetic. As used herein, the term "synthetic" with respect to a polypeptide linker includes peptides (or polypeptides) which comprise an amino acid sequence (which may or may not be naturally occurring) that is linked in a linear sequence of amino acids to a sequence (which may or may not be naturally occurring) (e.g., a Fc sequence) to which it is not naturally linked in nature. For example, the polypeptide linker may comprise non-naturally occurring polypeptides which are modified forms of naturally occurring polypeptides (e.g., comprising a mutation such as an addition, substitution or deletion) or which comprise a first amino acid sequence (which may or may not be naturally occurring). The polypeptide linkers of the invention may be employed, for instance, to ensure that Fc, or a variant or fragment thereof, is juxtaposed to ensure proper folding and formation of a functional Fc, or a variant or fragment thereof. Preferably, a polypeptide linker compatible with the instant invention will be relatively non-immunogenic and not inhibit any non-covalent association among monomer subunits of a binding protein.

In certain embodiments, the optimized binuclease fusion protein employs an NLG linker as set forth in SEQ ID NO: 41.

In certain embodiments, the optimized binuclease fusion proteins of the disclosure employ a polypeptide linker to join any two or more domains in frame in a single polypeptide chain. In one embodiment, the two or more domains may be independently selected from any of the Fc domains, or variants or fragments thereof, or nuclease domains discussed herein. For example, in certain embodiments, a polypeptide linker can be used to fuse identical Fc fragments, thereby forming a homodimeric Fc region. In other embodiments, a polypeptide linker can be used to fuse different Fc fragments, thereby forming a heterodimeric Fc region. In other embodiments, a polypeptide linker of the invention can be used to genetically fuse the C-terminus of a first Fc fragment to the N-terminus of a second Fc fragment to form a complete Fc domain.

In one embodiment, a polypeptide linker comprises a portion of a Fc domain, or a variant or fragment thereof. For example, in one embodiment, a polypeptide linker can comprise a Fc fragment (e.g., C or N domain), or a different portion of a Fc domain or variant thereof.

In another embodiment, a polypeptide linker comprises or consists of a gly-ser linker. As used herein, the term "gly-ser linker" refers to a peptide that consists of glycine and serine residues. An exemplary gly/ser linker comprises an amino acid sequence of the formula (Gly$_4$Ser)n, wherein n is a positive integer (e.g., 1, 2, 3, 4, or 5). A preferred gly/ser linker is (Gly$_4$Ser)4. Another preferred gly/ser linker is (Gly$_4$Ser)3. Another preferred gly/ser linker is (Gly$_4$Ser)5. In certain embodiments, the gly-ser linker may be inserted between two other sequences of the polypeptide linker (e.g., any of the polypeptide linker sequences described herein). In other embodiments, a gly-ser linker is attached at one or both ends of another sequence of the polypeptide linker (e.g., any of the polypeptide linker sequences described herein). In yet other embodiments, two or more gly-ser linker are incorporated in series in a polypeptide linker.

In other embodiments, a polypeptide linker of the invention comprises a biologically relevant peptide sequence or a sequence portion thereof. For example, a biologically relevant peptide sequence may include, but is not limited to, sequences derived from an anti-rejection or anti-inflammatory peptide. Said anti-rejection or anti-inflammatory peptides may be selected from the group consisting of a cytokine inhibitory peptide, a cell adhesion inhibitory peptide, a thrombin inhibitory peptide, and a platelet inhibitory peptide. In a preferred embodiment, a polypeptide linker comprises a peptide sequence selected from the group consisting of an IL-1 inhibitory or antagonist peptide sequence, an erythropoietin (EPO)-mimetic peptide sequence, a thrombopoietin (TPO)-mimetic peptide sequence, G-CSF mimetic peptide sequence, a TNF-antagonist peptide sequence, an integrin-binding peptide sequence, a selectin antagonist peptide sequence, an anti-pathogenic peptide sequence, a vasoactive intestinal peptide (VIP) mimetic peptide sequence, a calmodulin antagonist peptide sequence, a mast cell antagonist, a SH3 antagonist peptide sequence, an urokinase receptor (UKR) antagonist peptide sequence, a somatostatin or cortistatin mimetic peptide sequence, and a macrophage and/or T-cell inhibiting peptide sequence. Exemplary peptide sequences, any one of which may be employed as a polypeptide linker, are disclosed in U.S. Pat. No. 6,660,843, which is incorporated by reference herein.

Other linkers that are suitable for use in optimized binuclease fusion proteins are known in the art, for example, the serine-rich linkers disclosed in U.S. Pat. No. 5,525,491, the helix forming peptide linkers (e.g., A(EAAAK)nA (n=2-5)) disclosed in Arai et al., *Protein Eng* 2001; 14:529-32, and the stable linkers disclosed in Chen et al., *Mol Pharm* 2011; 8:457-65, i.e., the dipeptide linker LE, a thrombin-sensitive disulfide cyclopeptide linker, and the alpha-helix forming linker LEA(EAAAK)$_4$ALEA(EAAAK)$_4$ALE (SEQ ID NO: 53).

Other exemplary linkers include GS linkers (i.e., (GS)n), GGSG (SEQ ID NO: 70) linkers (i.e., (GGSG)n), GSAT linkers (SEQ ID NO: 44), SEG linkers, and GGS linkers (i.e., (GGSGGS)n), wherein n is a positive integer (e.g., 1, 2, 3, 4, or 5). Other suitable linkers for use in the optimized binuclease fusion proteins can be found using publicly available databases, such as the Linker Database (ibi.vu.nl/programs/linkerdbwww). The Linker Database is a database of inter-domain linkers in multi-functional enzymes which serve as potential linkers in novel fusion proteins (see, e.g., George et al., *Protein Engineering* 2002; 15:871-9).

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. Mutations may be introduced by standard techniques, such as site-directed mutagenesis and PCR-mediated mutagenesis.

Polypeptide linkers of the disclosure are at least one amino acid in length and can be of varying lengths. In one embodiment, a polypeptide linker of the invention is from about 1 to about 50 amino acids in length. As used in this context, the term "about" indicates +/−two amino acid residues. Since linker length must be a positive integer, the length of from about 1 to about 50 amino acids in length, means a length of from 1 to 48-52 amino acids in length. In another embodiment, a polypeptide linker of the disclosure is from about 10-20 amino acids in length. In another embodiment, a polypeptide linker of the disclosure is from about 15 to about 50 amino acids in length.

In another embodiment, a polypeptide linker of the disclosure is from about 20 to about 45 amino acids in length. In another embodiment, a polypeptide linker of the disclosure is from about 15 to about 25 amino acids in length. In another embodiment, a polypeptide linker of the disclosure is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 or more amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

Exemplary Optimized Binuclease Fusion Proteins

The optimized binuclease fusion proteins of the invention are modular, and can be configured to incorporate various individual domains. For example, in one embodiment, the optimized binuclease fusion protein may include the mutant, human DNase1 A114F domain set forth in (SEQ ID NO: 21). In another embodiment, the optimized binuclease fusion protein may include the mutant, human DNase1 N18S/N106S/A114F domain set forth in SEQ ID NO: 24. In another embodiment, the optimized binuclease fusion protein may include the human, wild-type RNase1 domain set forth in SEQ ID NO: 27. In another embodiment, the optimized binuclease fusion protein may include the human, mutant RNase1 N34S/N76S/N88S domain set forth in SEQ ID NO: 28. In another embodiment, the optimized binuclease fusion protein may include the (Gly$_4$Ser)3 linker domain set forth in SEQ ID NO: 30. In another embodiment, the optimized binuclease fusion protein may include the NLG linker set forth in SEQ ID NO: 41. In another embodiment, the optimized binuclease fusion protein may include a VK3LP leader (SEQ ID NO: 54). It will be understood to the skilled artisan that these individual domains can be operably coupled to each other in any order to form an optimized binuclease fusion protein that is enzymatically active. For example, as detailed in the specific examples below, RNase1 can be operably coupled to an Fc domain. In another example, RNase1 can be operatively coupled to Fc domain via a (Gly$_4$Ser)3 linker domain. In yet another example, DNase1 A114F can be operatively coupled to Fc domain. In yet another example, DNase1 A114F can be operatively coupled to Fc domain via a (Gly$_4$Ser)3 linker domain. Various other configurations are possible, with non-limiting exemplary configurations disclosed herein, in FIG. 1 and in the Sequence Table.

In some embodiments, an optimized binuclease fusion protein comprises a wild-type, human RNase1 domain operably coupled to a mutant Fc domain comprising SCC hinge and CH2 mutations P238S and P331S, or fragment thereof, and a mutated human DNase1 domain operably coupled to the human RNase1, thereby forming a tandem homodimer. In some embodiments, the DNase1 is linked to the RNase1 via a peptide linker, such as an NLG linker disclosed herein. In some embodiments, the RNase1 is operably linked with or without a linker to the N-terminus of the Fc domain. In some embodiments, an optimized binuclease fusion protein comprises a polypeptide having the amino acid sequence set forth in SEQ ID NO: 1. In some embodiments, the RNase1 is operably linked with or without a linker to the C-terminus of the Fc domain. In some embodiments, an optimized binuclease fusion protein comprises a polypeptide having the amino acid sequence set forth in SEQ ID NO: 2. In some embodiments, the optimized binuclease fusion protein is homodimeric or heterodimeric.

In some embodiments, an optimized binuclease fusion protein is a heterodimer comprising mutant human DNase 1 domain operably coupled with or without a linker to a first mutant Fc domain, having SCC hinge, CH2 mutations P238S, P331S, and CH3 mutations T350V, L351Y, F405A and Y407V, or a variant or fragment thereof, and a wild-type human RNase 1 domain operably coupled with or without a linker to a second mutant Fc domain comprising SCC hinge, CH2 mutations P238S and P331S and CH3 mutations T350V, T366L, K392L and T394W, or a fragment thereof. In some embodiments, the DNase1 and RNase 1 are both linked to the N-terminus of their respective Fc domains. In some embodiments, an optimized binuclease fusion protein is a heterodimer comprising a polypeptide comprising the amino acid sequence set forth in SEQ ID NOs: 3 and a polypeptide comprising the amino acid sequence set for in SEQ ID NO: 4.

In some embodiments, an optimized binuclease fusion protein is a heterodimer comprising a mutant human DNase 1 domain and wild-type human RNase 1 domain, both operably coupled with or without a linker to a first mutant Fc domain, comprising SCC hinge, CH2 mutations P238S and P331S and CH3 mutations T350V, T366L, K392L and T394W, or a fragment thereof, and a second mutant Fc domain, having mutations T350V, T366L, K392L and T394W, or fragment thereof. In some embodiments, the DNase1 and RNase 1 are linked to the N-terminus and C-terminus, respectively, of the first and second Fc domains. In some embodiments, an optimized binuclease fusion protein is a heterodimer comprising a polypeptide comprising the sequence set forth in SEQ ID NO: 5 and a polypeptide comprising the amino acid sequence set forth in SEQ ID NO: 6.

In some embodiments, an optimized binuclease fusion protein is a heterodimer comprising a mutant human DNase 1 domain, operably coupled with or without a linker to a mutant Fc domain comprising SCC hinge, CH2 mutations P238S, P331S and CH3 mutations T350V, L351Y, F405A and Y407V, or fragment thereof, and wild-type human RNase 1 domain, operably coupled with or without a linker to a mutant Fc domain comprising SCC hinge, CH2 mutations P238S, P331S and CH3 mutations T350V, T366L, K392L and T394W, or fragment thereof. In some embodiments, the DNase1 is linked to the N-terminus of the Fc domain and the RNase1 is linked to the C-terminus of the Fc domain. In some embodiments, an optimized binuclease fusion protein is a heterodimer comprising a polypeptide comprising the sequence set forth in SEQ ID NO: 7 and a polypeptide comprising the amino acid sequence set forth in SEQ ID NO: 8.

In some embodiments, an optimized binuclease fusion protein is a heterodimer comprising a mutant human DNase 1 domain operably coupled with or without a linker to a mutant Fc domain comprising SCC hinge, CH2 mutations P238S, P331S and CH3 mutations T350V, L351Y, F405A and Y407V, or fragment thereof, and a wild-type human RNase 1 domain operably coupled with or without a linker to a mutant Fc domain comprising SCC hinge, CH2 mutations P238S, P331S and CH3 mutations T350V, T366L, K392L and T394W, or fragment thereof. In some embodiments, the DNase1 and RNase 1 are both linked to the C-terminus of their respective Fc domains. In some embodiments, an optimized binuclease fusion protein is a heterodimer comprising a polypeptide comprising the sequence set forth in SEQ ID NO: 9 and a polypeptide comprising the amino acid sequence set forth in SEQ ID NO: 10. In some embodiments, an optimized binuclease fusion protein is a heterodimer comprising a polypeptide comprising the sequence set forth in SEQ ID NO: 11 and a polypeptide comprising the amino acid sequence set forth in SEQ ID NO: 12.

In some embodiments, an optimized binuclease fusion protein is a heterodimer comprising a mutant human DNase 1 domain and wild-type human RNase 1 domain, both operably coupled with or without a linker to a mutant Fc domain comprising SCC hinge, CH2 mutations P238S, P331S and CH3 mutations T350V, L351Y, F405A and Y407V, or fragment thereof, and a mutant Fc domain comprising SCC hinge, CH2 mutations P238S, P331S and CH3 mutations T350V, T366L, K392L and T394W, or fragment thereof. In some embodiments, the DNase1 and RNase 1 are linked to the C-terminus and N-terminus, respectively, of the Fc domain. In some embodiments, an optimized binuclease fusion protein is a heterodimer comprising a polypeptide comprising the sequence set forth in SEQ ID NO:13 and a polypeptide comprising the amino acid sequence set forth in SEQ ID NO: 14.

In some embodiments, an optimized binuclease fusion protein is a heterodimer comprising a mutant human DNase 1 domain, operably coupled with or without a linker to a mutant Fc domain comprising SCC hinge, CH2 mutations P238S, P331S and CH3 mutations T350V, L351Y, F405A and Y407V, or fragment thereof, and wild-type human RNase 1 domain, operably coupled with or without a linker to a mutant Fc domain comprising SCC hinge, CH2 mutations P238S, P331S and CH3 mutations T350V, T366L, K392L and T394W, or fragment thereof. In some embodiments, the DNase1 is linked to the C-terminus of the Fc domain and the RNase1 is linked to the N-terminus of the Fc domain. In some embodiments, an optimized binuclease fusion protein is a heterodimer comprising a polypeptide comprising the sequence set forth in SEQ ID NO: 15 and a polypeptide comprising the amino acid sequence set forth in SEQ ID NO: 16.

In some embodiments, an optimized binuclease fusion protein comprising a polypeptide having an amino acid sequence at least 80% identical, such as 85%, 90%, 91%, 92%, 93%, 94%, 95%, 96%, 97%, 98%, 99%, or at least 99.5% identical to an amino acid sequence of any one of SEQ ID NOs: 1-17. In some embodiments, the polypeptide comprises an amino acid sequence set for in any one of SEQ ID NOs: 1-17.

In some embodiments, the foregoing optimized binuclease fusion proteins have a leader sequence.

It will be understood by one of ordinary skill that the leader and linker sequences are optional and are not limited to those described in the embodiments above. For example, the RNase and/or DNase domains can be directly fused to the N- and/or C-terminus of Fc, or variant or fragment thereof; the leader domain can be any of those known in the art to be useful for its intended purpose, e.g., to increase protein expression and/or secretion (e.g., a *Gaussia* luciferase signal peptide (MGVKVLFALICIAVAEA; SEQ ID NO: 31)); the linker can be any linker known in the art, e.g., (Gly$_4$Ser)n, NLG (VDGASSPVNVSSPSVQDI; SEQ ID NO: 41), LE, thrombin-sensitive disulphide cyclopeptide linker, LEA(EAAAK)4ALEA(EAAAK)4 (SEQ ID NO: 32), or an in vivo cleavable disulphide linker, as described herein. It will also be understood that it is within the abilities of a skilled artisan to make the corresponding changes to the amino acid sequences of the optimized binuclease fusion protein using routine cloning and recombination methods. It will also be understood that the asparagine residues in the nuclease domains (i.e., N34, N76, and N88 in RNase1, and N18 and N106 in DNase1) can be substituted with an amino acid other than serine (e.g., glutamine), as long as the amino acid does not serve as an acceptor for N-linked glycosylation.

Methods of Making Optimized Binuclease Fusion Proteins

The optimized binuclease fusion proteins of this disclosure largely may be made in transformed or transfected host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used. The invention also includes a vector capable of expressing the peptides in an appropriate host. The vector comprises the DNA molecule that codes for the peptides operably coupled to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform or transfect an appropriate host. This transformation or transfection may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation or transfection, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli*), yeast (such as *Saccharomyces*) and other fungi, insects, plants, mammalian (including human) cells in culture, or other hosts known in the art. In a preferred embodiment, the optimized binuclease fusion proteins are produced in CHO cells.

Next, the transformed or transfected host is cultured and purified. Host cells may be cultured under conventional fermentation or culture conditions so that the desired compounds are expressed. Such fermentation and culture conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al., *Biochem Intl* 1985; 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

Optimized Binuclease Fusion Proteins with Altered Glycosylation

Glycosylation (e.g., 0-lined or N-linked glycosylation) can impact the serum half-life of the optimized binuclease fusion proteins of the disclosure by, e.g., minimizing their removal from circulation by mannose and asialoglycoprotein receptors and other lectin-like receptors. Accordingly, in some embodiments, the optimized binuclease fusion proteins of the disclosure are prepared in aglycosylated, deglycosylated, or underglycosylated form. Preferably, N-linked glycosylation is altered and the optimized binuclease fusion protein is aglycosylated.

In some embodiments, all asparagine residues in an optimized binuclease fusion protein that conform to the Asn-X-Ser/Thr (X can be any other naturally occurring amino acid except Pro) consensus are mutated to residues that do not serve as acceptors of N-linked glycosylation (e.g., serine, glutamine), thereby eliminating glycosylation of the optimized binuclease fusion protein when synthesized in a cell that glycosylates proteins.

In some embodiments, optimized binuclease fusion proteins lacking N-linked glycosylation sites are produced in mammalian cells. In one embodiment, the mammalian cell is a CHO cell. Accordingly, in a specific embodiment, an aglycosylated optimized binuclease fusion protein is produced in a CHO cell.

In other embodiments, a reduction or lack of N-glycosylation is achieved by, e.g., producing optimized binuclease fusion proteins in a host (e.g., bacteria such as *E. coli*), mammalian cells engineered to lack one or more enzymes important for glycosylation, or mammalian cells treated with agents that prevent glycosylation, such as tunicamycin (an inhibitor of Dol-PP-GlcNAc formation).

In some embodiments, the optimized binuclease fusion proteins are produced in lower eukaryotes engineered to produce glycoproteins with complex N-glycans, rather than high mannose type sugars (see, e.g., US2007/0105127).

In some embodiments, glycosylated optimized binuclease fusion proteins (e.g., those produced in mammalian cells such as CHO cells) are treated chemically or enzymatically to remove one or more carbohydrate residues (e.g., one or more mannose, fucose, and/or N-acetylglucosamine residues) or to modify or mask one or more carbohydrate residues. Such modifications or masking may reduce binding of the optimized binuclease fusion proteins to mannose receptors, and/or asialoglycoprotein receptors, and/or other lectin-like receptors. Chemical deglycosylation can be achieved by treating an optimized binuclease fusion protein with trifluoromethane sulfonic acid (TFMS), as disclosed in, e.g., Sojar et al., *JBC* 1989; 264:2552-9 and Sojar et al., *Methods Enzymol* 1987; 138:341-50, or by treating with hydrogen fluoride, as disclosed in Sojar et al. (1987, supra). Enzymatic removal of N-linked carbohydrates from optimized binuclease fusion proteins can be achieved by treating an optimized binuclease fusion protein with protein N-glycosidase (PNGase) A or F, as disclosed in Thotakura et al. (*Methods Enzymol* 1987; 138:350-9). Other art-recognized commercially available deglycosylating enzymes that are suitable for use include endo-alpha-N-acetyl-galactosaminidase, endoglycosidase F1, endoglycosidase F2, endoglycosidase F3, and endoglycosidase H. In some embodiments, one or more of these enzymes can be used to deglycosylate the optimized binuclease fusion proteins of the disclosure. Alternative methods for deglycosylation are disclosed in, e.g., U.S. Pat. No. 8,198,063.

In some embodiments, the optimized binuclease fusion proteins are partially deglycosylated. Partial deglycosylation can be achieved by treating the optimized binuclease fusion proteins with an endoglycosidase (e.g., endoglycosidase H), which cleaves N-linked high mannose carbohydrate but not complex type carbohydrates, leaving a single GlcNAc residue linked to the asparagine. Optimized binuclease fusion proteins treated with endoglycosidase H will lack high mannose carbohydrates, resulting in a reduced interaction with the hepatic mannose receptor. Although this receptor recognizes terminal GlcNAc, the probability of a productive interaction with the single GlcNAc on the protein surface is not as great as with an intact high mannose structure.

In other embodiments, glycosylation of an optimized binuclease fusion protein is modified, e.g., by oxidation, reduction, dehydration, substitution, esterification, alkylation, sialylation, carbon-carbon bond cleavage, or the like, to reduce clearance of the optimized binuclease fusion proteins from blood. In some embodiments, the optimized binuclease fusion proteins are treated with periodate and sodium borohydride to modify the carbohydrate structure. Periodate treatment oxidizes vicinal diols, cleaving the carbon-carbon bond and replacing the hydroxyl groups with aldehyde groups; borohydride reduces the aldehydes to hydroxyls. Many sugar residues include vicinal diols and, therefore, are cleaved by this treatment. Prolonged serum half-life with periodate and sodium borohydride is exemplified by the sequential treatment of the lysosomal enzyme β-glucuronidase with these agents (see, e.g., Houba et al. (1996) *Bioconjug Chem* 1996:7:606-11; Stahl et al. *PNAS* 1976; 73:4045-9; Achord et al. *Pediat. Res* 1977; 11:816-22; Achord et al. *Cell* 1978; 15:269-78). A method for treatment with periodate and sodium borohydride is disclosed in Hickman et al., *BBRC* 1974; 57:55-61. A method for treatment with periodate and cyanoborohydride, which increases the serum half-life and tissue distribution of ricin, is disclosed in Thorpe et al. *Eur J Biochem* 1985; 147:197-206.

In one embodiment, the carbohydrate structures of an optimized binuclease fusion protein can be masked by addition of one or more additional moieties (e.g., carbohydrate groups, phosphate groups, alkyl groups, etc.) that interfere with recognition of the structure by a mannose or asialoglycoprotein receptor or other lectin-like receptors.

In some embodiments, one or more potential glycosylation sites are removed by mutation of the nucleic acid encoding the optimized binuclease fusion protein, thereby reducing glycosylation (underglycosylation) of the optimized binuclease fusion protein when synthesized in a cell that glycosylates proteins, e.g., a mammalian cell such as a CHO cell. In some embodiments, it may be desirable to selectively underglycosylate the nuclease domain of the optimized binuclease fusion proteins by mutating the potential N-linked glycosylation sites therein if, e.g., the underglycosylated optimized binuclease fusion protein exhibits increased activity or contributes to increased serum half-life. In other embodiments, it may be desirable to underglycosylate portions of the optimized binuclease fusion protein such that regions other than the nuclease domain lack N-glycosylation if, for example, such a modification improves the serum half-life of the optimized binuclease fusion protein. Alternatively, other amino acids in the vicinity of glycosylation acceptors can be modified, disrupting a recognition motif for glycosylation enzymes without necessarily changing the amino acid that would normally be glycosylated.

In some embodiments, glycosylation of an optimized binuclease fusion protein can be altered by introducing glycosylation sites. For example, the amino acid sequence of the optimized binuclease fusion protein can be modified to introduce the consensus sequence for N-linked glycosylation of Asp-X-Ser/Thr (X is any amino acid other than proline). Additional N-linked glycosylation sites can be added anywhere throughout the amino acid sequence of the optimized binuclease fusion protein. Preferably, the glycosylation sites are introduced in position in the amino acid sequence that does not substantially reduce the nuclease (e.g., RNase and/or DNase) activity of the optimized binuclease fusion protein.

The addition of O-linked glycosylation sites has been reported to alter serum half-life of proteins, such as growth hormone, follicle-stimulating hormone, IGFBP-6, Factor IX, and many others (e.g., as disclosed in Okada et al., *Endocr Rev* 2011; 32:2-342; Weenen et al., *J Clin Endocrinol Metab* 2004; 89:5204-12; Marinaro et al., *European Journal of Endocrinology* 2000; 142:512-6; US 2011/0154516). Accordingly, in some embodiments, O-linked glycosylation (on serine/threonine residues) of the optimized binuclease fusion proteins is altered. Methods for altering O-linked glycosylation are routine in the art and can be achieved, e.g., by beta-elimination (see, e.g., Huang et al., Rapid Communications in Mass Spectrometry 2002; 16:1199-204; Conrad, *Curr Protoc Mol Biol* 2001; Chapter 17:Unit 17.15A; Fukuda, *Curr Protoc Mol Biol* 2001; Chapter 17; Unit 17.15B; Zachara et al., *Curr Protoc Mol Biol* 2011; Unit 17.6;); by using commercially available kits (e.g., GlycoProfile™ Beta-Elimination Kit, Sigma); or by subjecting optimized binuclease fusion protein to treatment with a series of exoglycosidases such as, but not limited to, β1-4 galactosidase and β-N-acetylglucosaminidase, until only Gal β1-3GalNAc and/or GlcNAc β1-3GalNAc remains, followed by treatment with, e.g., endo-α-N-acetylgalactosaminidase (i.e., O-glycosidase). Such enzymes are commercially available from, e.g., New England Biolabs. In yet other embodiments, the optimized binuclease fusion proteins are altered to introduce O-linked glycosylation in the optimized binuclease fusion protein as disclosed in, e.g., Okada et al. (supra), Weenen et al. (supra), US2008/0274958; and US2011/0171218. In some embodiments, one or more O-linked glycosylation consensus sites are introduced into the optimized binuclease fusion protein, such as CXXGGT/S-C (SEQ ID NO: 33) (van den Steen et al., In Critical Reviews in Biochemistry and Molecular Biology, Michael Cox, ed., 1998; 33:151-208), NST-E/D-A (SEQ ID NO: 34), NITQS (SEQ ID NO: 35), QSTQS (SEQ ID NO: 36), D/E-FT-R/K-V (SEQ ID NO: 37), C-E/D-SN (SEQ ID NO: 38), and GGSC-K/R (SEQ ID NO: 39). Additional O-linked glycosylation sites can be added anywhere throughout the amino acid sequence of the optimized binuclease fusion protein. Preferably, the glycosylation sites are introduced in position in the amino acid sequence that does not substantially reduce the nuclease (e.g., RNase and/or DNase) activity of the optimized binuclease fusion protein. Alternatively, O-linked sugar moieties are introduced by chemically modifying an amino acid in the optimized binuclease fusion protein as described in, e.g., WO 87/05330 and Aplin et al., *CRC Crit Rev Biochem* 1981; 259-306).

In some embodiments, both N-linked and O-linked glycosylation sites are introduced into the optimized binuclease fusion proteins, preferably in positions in the amino acid sequence that do not substantially reduce the nuclease (e.g., RNase and/or DNase) activity of the optimized binuclease fusion protein.

It is well within the abilities of the skilled artisan to introduce, reduce, or eliminate glycosylation (e.g., N-linked or O-linked glycosylation) in an optimized binuclease fusion protein and determine using routine methods in the art whether such modifications in glycosylation status increases or decreases the nuclease activity or serum half-life of the optimized binuclease fusion protein.

In some embodiments, the optimized binuclease fusion protein may comprise an altered glycoform (e.g., an under-fucosylated or fucose-free glycan).

In some embodiments, an optimized binuclease fusion protein with altered glycosylation has a serum half-life that is increased at least about 1.5-fold, such as at least 3-fold, at least 5-fold, at least 10-fold, at least about 20-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1000-fold, or 1000-fold or greater relative to the corresponding glycosylated optimized binuclease fusion proteins (e.g., an optimized binuclease fusion protein in which potential N-linked glycosylation sites are not mutated). Routine art-recognized methods can be used to determine the serum half-life of optimized binuclease fusion proteins with altered glycosylation status.

In some embodiments, an optimized binuclease fusion protein with altered glycosylation (e.g., a aglycosylated, deglycosylated, or underglycosylated optimized binuclease fusion proteins) retains at least 50%, such as at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or 100% of the activity of the corresponding glycosylated optimized binuclease fusion protein (e.g., an optimized binuclease fusion protein in which potential N-linked glycosylation sites are not mutated).

In some embodiments, altering the glycosylation status of the optimized binuclease fusion proteins may increase nuclease activity, either by directly increasing enzymatic activity, or by increasing bioavailability (e.g., serum half-life). Accordingly, in some embodiments, the nuclease activity of an optimized binuclease fusion protein with altered glycosylation is increased by at least 1.3-fold, such as at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5 fold, or 10-fold or greater, relative to the corresponding glycosylated optimized binuclease fusion protein (e.g., an optimized binuclease fusion protein in which potential N-linked glycosylation sites are not mutated).

The skilled artisan can readily determine the glycosylation status of optimized binuclease fusion proteins using art-recognized methods. In a preferred embodiment, the glycosylation status is determined using mass spectrometry. In other embodiments, interactions with Concanavalin A (Con A) can be assessed to determine whether an optimized binuclease fusion protein is underglycosylated. An underglycosylated optimized binuclease fusion protein is expected to exhibit reduced binding to Con A-Sepharose when compared to the corresponding glycosylated optimized binuclease fusion protein. SDS-PAGE analysis can also be used to compare the mobility of an underglycosylated protein and corresponding glycosylated protein. The underglycosylated protein is expected to have a greater mobility in SDS-PAGE compared to the glycosylated protein. Other suitable art-recognized methods for analyzing protein glycosylation status are disclosed in, e.g., Roth et al., International Journal of Carbohydrate Chemistry 2012; 1-10.

Pharmacokinetics, such as serum half-life, of optimized binuclease fusion proteins with different glycosylation status can be assayed using routine methods, e.g., by introducing the optimized binuclease fusion proteins in mice, e.g., intravenously, taking blood samples at pre-determined time points, and assaying and comparing levels and/or enzymatic activity of the optimized binuclease fusion proteins in the samples.

Pharmaceutical Compositions

In certain embodiments, an optimized binuclease fusion protein is administered alone. In certain embodiments, an optimized binuclease fusion protein is administered prior to the administration of at least one other therapeutic agent. In certain embodiments, an optimized binuclease fusion protein is administered concurrent with the administration of at least one other therapeutic agent. In certain embodiments, an optimized binuclease fusion protein is administered subsequent to the administration of at least one other therapeutic agent. In other embodiments, an optimized binuclease fusion protein is administered prior to the administration of at least one other therapeutic agent. As will be appreciated by one of skill in the art, in some embodiments, the optimized binuclease fusion protein is combined with the other agent/compound. In some embodiments, the optimized binuclease fusion protein and other agent are administered concurrently. In some embodiments, the optimized binuclease fusion protein and other agent are not administered simultaneously, with the optimized binuclease fusion protein being administered before or after the agent is administered. In some embodiments, the subject receives both the optimized binuclease fusion protein and the other agent during a same period of prevention, occurrence of a disorder, and/or period of treatment.

Pharmaceutical compositions of the invention can be administered in combination therapy, i.e., combined with other agents. In certain embodiments, the combination therapy comprises the optimized binuclease fusion protein, in combination with at least one other agent. Agents include, but are not limited to, in vitro synthetically prepared chemical compositions, antibodies, antigen binding regions, and combinations and conjugates thereof. In certain embodiments, an agent can act as an agonist, antagonist, allosteric modulator, or toxin.

In certain embodiments, the invention provides for pharmaceutical compositions comprising a optimized binuclease fusion protein together with a pharmaceutically acceptable diluent, carrier, solubilizer, emulsifier, preservative and/or adjuvant.

In certain embodiments, the invention provides for pharmaceutical compositions comprising a optimized binuclease fusion protein and a therapeutically effective amount of at least one additional therapeutic agent, together with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In some embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as gelatin); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

In certain embodiments, a optimized binuclease fusion protein and/or a therapeutic molecule is linked to a half-life extending vehicle known in the art. Such vehicles include, but are not limited to, polyethylene glycol, glycogen (e.g., glycosylation of the optimized binuclease fusion protein), and dextran. Such vehicles are described, e.g., in U.S. application Ser. No. 09/428,082, now U.S. Pat. No. 6,660,843 and published PCT Application No. WO 99/25044.

In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the antibodies of the invention.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In some embodiments, the saline comprises isotonic phosphate-buffered saline. In certain embodiments, pharmaceutical compositions comprise Tris buffer of about pH 7.0-8.5, or acetate buffer of about H 4.0-5.5, which can further include sorbitol or a suitable substitute therefore. In certain embodiments, a composition comprising an optimized binuclease fusion protein, with or without at least one additional therapeutic agents, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising an optimized binuclease fusion protein, with or without at least one additional therapeutic agent, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired optimized binuclease fusion protein, with or without additional therapeutic agents, in a pharmaceutically acceptable vehicle. In certain embodiments, a vehicle for parenteral injection is sterile distilled water in which an optimized binuclease fusion protein, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, an optimized binuclease fusion protein, with or without at least one additional therapeutic agent, can be formulated as a dry powder for inhalation. In certain embodiments, an inhalation solution comprising an optimized binuclease fusion protein, with or without at least one additional therapeutic agent, can be formulated with a propellant for aerosol delivery. In certain embodiments, solutions can be nebulized. Pulmonary administration is further described in PCT application no. PCT/US94/001875, which describes pulmonary delivery of chemically modified proteins.

In certain embodiments, it is contemplated that formulations can be administered orally. In certain embodiments, an optimized binuclease fusion protein, with or without at least one additional therapeutic agents, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of an optimized binuclease fusion protein and/or any additional therapeutic agents. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of an optimized binuclease fusion protein, with or without at least one additional therapeutic agents, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving an optimized binuclease fusion protein, with or without at least one additional therapeutic agent(s), in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al, *Biopolymers,* 22:547-556 (1983)), poly (2-hydroxyethyl-methacrylate) (Langer et al., *J Biomed Mater Res,* 15: 167-277 (1981) and Langer, *Chem Tech,* 12:98-105 (1982)), ethylene vinyl acetate (Langer et al, supra) or poly-D(−)-3-hydroxybutyric acid (EP 133,988). In certain embodiments, sustained release compositions can also include liposomes, which can be prepared by any of several methods known in the art. See, e.g., Eppstein et al, *PNAS,* 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising an optimized binuclease fusion protein, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which an optimized binuclease fusion protein, with or without at least one additional therapeutic agent, is being used, the route of administration, and the size (body weight, body surface or organ size) and/or condition (the age and general health) of the patient. In certain embodiments, the clinician can titer the dosage and modify the route of administration to obtain the optimal therapeutic effect. In certain embodiments, a typical dosage can range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of an optimized binuclease fusion protein and/or any additional therapeutic agents in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

In certain embodiments, it can be desirable to use a pharmaceutical composition comprising an optimized binuclease fusion protein, with or without at least one additional therapeutic agent, in an ex vivo manner. In such instances, cells, tissues and/or organs that have been removed from the patient are exposed to a pharmaceutical composition comprising an optimized binuclease fusion protein, with or without at least one additional therapeutic agent, after which the cells, tissues and/or organs are subsequently implanted back into the patient.

In certain embodiments, an optimized binuclease fusion protein and/or any additional therapeutic agents can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

In Vitro Assays

Various in vitro assays known in the art can be used to assess the efficacy of the optimized binuclease fusion proteins of the invention.

For example, cultured human PBMCs from normal or lupus patient PBMCs are isolated, cultured, and treated with various stimuli (e.g., TLR ligands, costimulatory antibodies, immune complexes, and normal or autoimmune sera), in the presence or absence of the optimized binuclease fusion proteins. Cytokine production by the stimulated cells can be measured using commercially available reagents, such as the antibody pair kits from Biolegend (San Diego, CA) for various cytokines (e.g., IL-6, IL-8, IL-10, IL-4, IFN-gamma, and TNF-alpha). Culture supernatants are harvested at various time points as appropriate for the assay (e.g., 24, 48 hours, or later time points) to determine the effects that the optimized binuclease fusion proteins have on cytokine production. IFN-alpha production is measured using, e.g., anti-human IFN-alpha antibodies and standard curve reagents available from PBL interferon source (Piscataway, NJ). Similar assays are performed using human lymphocyte subpopulations (isolated monocytes, B cells, pDCs, T cells, etc.); purified using, e.g., commercially available magnetic bead based isolation kits available from Miltenyi Biotech (Auburn, CA).

Multi-color flow cytometry can be used to assess the effects of the optimized binuclease fusion proteins on immune cell activation by measuring the expression of lymphocyte activation receptors such as CD5, CD23, CD69, CD80, CD86, and CD25 in PBMCs or isolated cell subpopulations at various time points after stimulation using routine art-recognized methods.

The efficacy of optimized binuclease fusion proteins can also be tested by incubating SLE patient serum with normal human pDCs to activate IFN output, as described in, e.g., Ahlin et al., *Lupus* 2012:21:586-95; Mathsson et al., *Clin Expt Immunol* 2007; 147:513-20; and Chiang et al., *J Immunol* 2011; 186:1279-1288. Without being bound by theory, circulating nucleic acid-containing immune complexes in SLE patient sera facilitate nucleic acid antigen entry into pDC endosomes via Fc receptor-mediated endocytosis, followed by binding of nucleic acids to and activation of endosomal TLRs 7, 8, and 9. To assess the impact of the optimized binuclease fusion proteinss, SLE patient sera or plasma is pretreated with the optimized binuclease fusion proteins, followed by addition to cultures of pDC cells isolated from healthy volunteers. Levels of IFN-α produced are then determined at multiple time points. By degrading nucleic-acid containing immune complexes, effective optimized binuclease fusion proteins are expected to reduce the quantity of IFN-α produced.

The effectiveness of optimized binuclease fusion proteins is demonstrated by comparing the results of an assay from cells treated with an optimized binuclease fusion protein disclosed herein to the results of the assay from cells treated with control formulations. After treatment, the levels of the various markers (e.g., cytokines, cell-surface receptors, proliferation) described above are generally improved in an effective optimized binuclease fusion protein treated group relative to the marker levels existing prior to the treatment, or relative to the levels measured in a control group.

Methods of Treatment

The optimized binuclease fusion proteins of the disclosure are particularly effective in the treatment of autoimmune disorders or abnormal immune responses. In this regard, it will be appreciated that the optimized binuclease fusion proteins of the present disclosure may be used to control, suppress, modulate, treat, or eliminate unwanted immune responses to both external and autoantigens.

In another aspect, an optimized binuclease fusion protein is adapted for preventing (prophylactic) or treating (therapeutic) a disease or disorder, such as an autoimmune disease, in a mammal by administering an optimized binuclease fusion protein in a therapeutically effective amount or a sufficient amount to the mammal in need thereof, wherein the disease is prevented or treated. Any route of administration suitable for achieving the desired effect is contemplated by the invention (e.g., intravenous, intramuscular, subcutaneous). Treatment of the disease condition may result in a decrease in the symptoms associated with the condition, which may be long-term or short-term, or even a transient beneficial effect.

Numerous disease conditions are suitable for treatment with optimized binuclease fusion proteins of the disclosure. For example, in some aspects, the disease or disorder is an autoimmune disease or cancer. In some such aspects, the autoimmune disease is insulin-dependent diabetes mellitus, multiple sclerosis, experimental autoimmune encephalomyelitis, rheumatoid arthritis, experimental autoimmune arthritis, myasthenia gravis, thyroiditis, an experimental form of uveoretinitis, Hashimoto's thyroiditis, primary myxoedema, thyrotoxicosis, pernicious anaemia, autoimmune atrophic gastritis, Addison's disease, premature menopause, male infertility, juvenile diabetes, Goodpasture's syndrome, pemphigus vulgaris, pemphigoid, sympathetic ophthalmia, phacogenic uveitis, autoimmune haemolytic anaemia, idiopathic leucopenia, primary biliary cirrhosis, active chronic hepatitis Hbs-ve, cryptogenic cirrhosis, ulcerative colitis, Sjogren's syndrome, scleroderma, Wegener's granulomatosis, polymyositis, dermatomyositis, discoid LE, SLE, or connective tissue disease.

In a specific embodiment, an optimized binuclease fusion protein is used to prevent or treat SLE or Sjogren's syndrome. The effectiveness of an optimized binuclease fusion protein is demonstrated by comparing the IFN-alpha levels, IFN-alpha response gene levels, autoantibody titers, kidney function and pathology, and/or circulating immune complex levels in mammals treated with an optimized binuclease fusion protein disclosed herein to mammals treated with control formulations.

For example, a human subject in need of treatment is selected or identified (e.g., a patient who fulfills the American College of Rheumatology criteria for SLE, or a patient who fulfills the American-European Consensus Sjogren's Classification Criteria). The subject can be in need of, e.g., reducing a cause or symptom of SLE or Sjogren's syndrome. The identification of the subject can occur in a clinical setting, or elsewhere, e.g., in the subject's home through the subject's own use of a self-testing kit.

At time zero, a suitable first dose of an optimized binuclease fusion protein is administered to the subject. The optimized binuclease fusion protein is formulated as described herein. After a period of time following the first dose, e.g., 7 days, 14 days, and 21 days, the subject's condition is evaluated, e.g., by measuring IFN-alpha levels, IFN-alpha response gene levels, autoantibody titers, kidney function and pathology, and/or circulating immune complex levels. Other relevant criteria can also be measured. The number and strength of doses are adjusted according to the subject's needs. After treatment, the subject's IFN-alpha levels, IFN-alpha response gene levels, autoantibody titers, kidney function and pathology, and/or circulating immune complex levels are lowered and/or improved relative to the levels existing prior to the treatment, or relative to the levels measured in a similarly afflicted but untreated/control subject.

In another example, a rodent subject in need of treatment is selected or identified (see, e.g., Example 7). The identification of the subject can occur in a laboratory setting or elsewhere. At time zero, a suitable first dose of an optimized binuclease fusion protein is administered to the subject. The optimized binuclease fusion protein is formulated as described herein. After a period of time following the first dose, e.g., 7 days, 14 days, and 21 days, the subject's condition is evaluated, e.g., by measuring IFN-alpha levels, IFN-alpha response gene levels, autoantibody titers, kidney function and pathology, and/or circulating immune complex levels. Other relevant criteria can also be measured. The number and strength of doses are adjusted according to the subject's needs.

After treatment, the subject's IFN-alpha levels, IFN-alpha response gene levels, autoantibody titers, kidney function and pathology, and/or circulating immune complex levels are lowered and/or improved relative to the levels existing prior to the treatment, or relative to the levels measured in a similarly afflicted but untreated/control subject.

Another aspect of the present invention is to use gene therapy methods for treating or preventing disorders, diseases, and conditions with one or more optimized binuclease fusion proteins. The gene therapy methods relate to the introduction of optimized binuclease fusion protein nucleic acid (DNA, RNA and antisense DNA or RNA) sequences into an animal in need thereof to achieve expression of the polypeptide or polypeptides of the present disclosure. This method can include introduction of one or more polynucleotides encoding an optimized binuclease fusion protein of the present disclosure operably coupled to a promoter and any other genetic elements necessary for the expression of the polypeptide by the target tissue.

In gene therapy applications, optimized binuclease fusion protein genes are introduced into cells in order to achieve in vivo synthesis of a therapeutically effective genetic product. "Gene therapy" includes both conventional gene therapies where a lasting effect is achieved by a single treatment, and the administration of gene therapeutic agents, which involves the one time or repeated administration of a therapeutically effective DNA or mRNA. The oligonucleotides can be modified to enhance their uptake, e.g., by substituting their negatively charged phosphodiester groups by uncharged groups.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al, Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

Example 1

Generating Optimized Binuclease Fusion Protein Encoding Expression Vectors

Various embodiments of the optimized binuclease fusion proteins of the disclosure are shown in FIG. 1, with amino acid sequences of each presented in the Sequence Table. As exemplary optimized binuclease fusion proteins, binuclease fusion proteins with the configurations shown in FIG. 1 were constructed. Specifically, starting from the amino acid sequence of the optimized binuclease fusion proteins, polynucleotides encoding the optimized binuclease fusion proteins were directly synthesized using codon optimization by Genescript (Genescript, Piscatawy, N.J.) to allow for optimal expression in mammalian cells. The process of optimization involved, e.g., avoiding regions of very high (>80%) or very low (<30%) GC content when possible, and avoiding cis-acting sequence motifs, such as internal TATA-boxes, chi-sites and ribosomal entry sites, AT-rich or GC-rich sequence stretches, RNA instability motifs, repeat sequences and RNA secondary structures, and cryptic splice donor and acceptor sites in higher eukaryotes. DNAs encoding the optimized binuclease fusion proteins are cloned into the pcDNA3.1+ mammalian expression vector. Optimized binuclease fusion proteins with the following configurations were generated.

Tandem homodimer RSLV-145 (SEQ ID NO: 1) has the configuration DNase-linker-RNase-Fc, wherein a wild-type, human RNase1 domain (SEQ ID NO: 27) is operably coupled without a linker to the N-terminus to a mutant Fc region comprising SCC hinge and CH2 mutations P238S, P331S (SEQ ID NO: 55) and a mutant human DNase1 domain (SEQ ID NO: 25) is operably coupled to the N-terminus of the RNase1 domain via a NLG linker (SEQ ID NO: 41).

To preferentially form heterodimers, each of the Fc domains in the following constructs included complementary CH3 mutations: T350V, L351Y, F405A, and Y407V; and T350V, T366L, K392L, and T394W (numbering according to the EU index.)

Tandem heterodimer RSLV-147 has the configuration DNase-Fc (SEQ ID NO: 3) and RNase-Fc (SEQ ID NO: 4), wherein a mutant human DNase1 domain (SEQ ID NO: 25) is operably coupled to the N-terminus of a first mutant Fc region comprising SCC hinge, CH2 mutations P238S, P331S and CH3 mutations, and wherein a wild-type, human RNase1 domain (SEQ ID NO: 27) is operably coupled to the N-terminus of a second mutant Fc region comprising SCC hinge, CH2 mutations P238S, P331S and CH3 mutations.

Heterodimer RSLV-148 has the configuration DNase-first Fc domain-linker-RNase (SEQ ID NO: 5) and a mutant second Fc domain (N-terminal truncation including first cysteine in CCC hinge) comprising CH2 mutations P238S, P331S and CH3 mutations (SEQ ID NO: 6), wherein a mutant human DNase1 domain (SEQ ID NO: 25) is operably coupled to the N-terminus of a first mutant Fc region comprising SCC hinge, CH2 mutations P238S, P331S and CH3 mutations, and wherein a wild-type, human RNase1 domain (SEQ ID NO: 27) is operably coupled via an NLG linker to the C-terminus of the first Fc region.

Heterodimer RSLV-149 has the configuration DNase-Fc (SEQ ID NO: 7) and Fc-linker-RNase (SEQ ID NO: 8), wherein a mutant human DNase1 domain (SEQ ID NO: 25) is operably coupled to the N-terminus of a first mutant Fc region comprising SCC hinge, CH2 mutations P238S, P331S and CH3 mutations, and wherein a wild-type, human RNase1 domain (SEQ ID NO: 27) is operably coupled via an NLG linker to the C-terminus of a second mutant Fc region comprising CH2 mutations P238S, P331S and CH3 mutations (SEQ ID NO:6).

Heterodimer RSLV-152 has the configuration RNase-first mutant Fc-linker-DNase (SEQ ID NO: 13) and a second mutant Fc domain comprising CH2 mutations P238S, P331S, and CH3 mutations (SEQ ID NO: 14), wherein a wild-type, human RNase1 domain (SEQ ID NO: 27) is operably coupled to the N-terminus of a first mutant Fc region comprising SCC hinge and CH2 mutations P238S, P331S and CH3 mutations, and wherein a mutant human DNase1 domain (SEQ ID NO: 25) is operably coupled via an NLG liner to the C-terminus of the first mutant Fc region.

Heterodimer RSLV-153 has the configuration Fc-linker-DNase (SEQ ID NO: 15) and RNase-Fc (SEQ ID NO: 16), wherein a mutant human DNase1 domain (SEQ ID NO: 25) is operably coupled via an NLG linker to the C-terminus of a first mutant Fc region comprising CH2 mutations P238S, P331S and CH3 mutations, and wherein a wild-type, human RNase1 domain (SEQ ID NO: 27) is operably coupled to the N-terminus of a second mutant Fc region comprising SCC hinge, CH2 mutations P238S, P331S and CH3 mutations.

Constructs RLSV-327 (a binuclease containing RNase 1 and DNase 1 linked to human serum albumin; RNase-linker-HSA-linker-DNase E13R/N74K/A114F/T205K) and RSLV-132 (RNase-Fc), containing DNase and RNase moieties, were used as controls.

Example 2

Transient Expression of and Stable Mammalian Cell Lines Expressing Optimized Binuclease Fusion Proteins For transient expression, expression vectors from Example 1 containing the optimized binuclease fusion protein inserts are transiently transfected using FreeStyle™ MAX Reagent into Chinese Hamster Ovary (CHO) cells, e.g., CHO-S cells (e.g., FreeStyle™ CHO-S cells, Invitrogen), using the manufacturer recommended transfection protocol. CHO-S cells are maintained in FreeStyle™ CHO Expression Medium containing 2 mM L-Glutamine and penicillin-streptomycin.

Stable CHO-S cell lines expressing the optimized binuclease fusion proteins are generated using routine methods known in the art. For example, CHO-S cells can be infected with a virus (e.g., retrovirus, lentivirus) comprising the nucleic acid sequences of an optimized binuclease fusion protein, as well as the nucleic acid sequences encoding a marker (e.g., GFP, surface markers selectable by magnetic beads) that is selected for using, e.g., flow cytometry or magnetic bead separation (e.g., MACSelect™ system). Alternatively, CHO-S cells are transfected using any transfection method known in the art, such as electroporation (Lonza) or the FreeStyle™ MAX Reagent as mentioned above, with a vector comprising the nucleic acid sequences of the optimized binuclease fusion proteins and a selectable marker, followed by selection using, e.g., flow cytometry. The selectable marker can be incorporated into the same vector as that encoding the optimized binuclease fusion proteins or a separate vector.

Optimized binuclease fusion proteins are purified from culture supernatant by capturing the molecules using a column packed with Protein-A sepharose beads, followed by washes in column wash buffer (e.g., 90 mM Tris, 150 mM NaCl, 0.05% sodium azide) and releasing the molecules from the column using a suitable elution buffer (e.g., 0.1 M citrate buffer, pH 3.0). The eluted material is further concentrated by buffer exchange through serial spins in PBS using Centricon concentrators, followed by filtration through 0.2 μm filter devices. The concentration of the optimized binuclease fusion proteins is determined using standard spectrophotometric methods (e.g., Bradford, BCA, Lowry, Biuret assays).

Example 3

Nuclease Activity of Purified Optimized Binuclease Fusion Proteins

Figure 2:
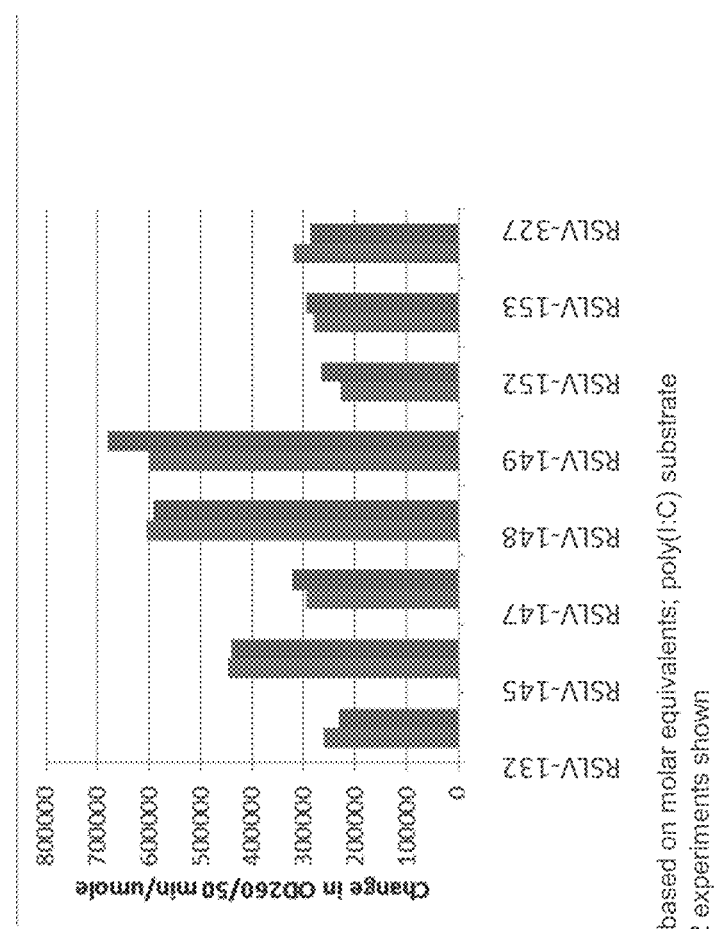
FIG. 2 is a graph showing RNase activity as measured by $OD_{260}$.

RNase activity of optimized binuclease fusion proteins present in mouse sera was analyzed. The proteins were added at doses of 12.5 to 100 ng to 2.5 mg/ml of poly-IC (Sigma) in 50 mM Hepes and 100 mM NaCl at pH 7.3 and incubated for 37° C. for 50 minutes. TCA was added to final concentration of 5% and left on ice. Samples were filtered to remove precipitated and the filtrate was collected for 013260 readings. The results are shown in FIG. 2. RSLV-132 and RSLV-145, both containing 2 RNase moieties per molar equivalent of construct, were both active, with RSLV-145 being more active than RSLV-132. The other constructs (RSLV-147, RSLV-152, RSLV-153 and RSLV-327), containing only one RNase moiety on a molar basis, were comparable and in line with RSLV-132. Surprisingly, RSLV-148 and RLSV-149 possessed activity greater than RSLV-132 and other single RNase constructs. These constructs each contain the RNase moiety attached at the C-terminus of the Fc domain.

Figure 3:
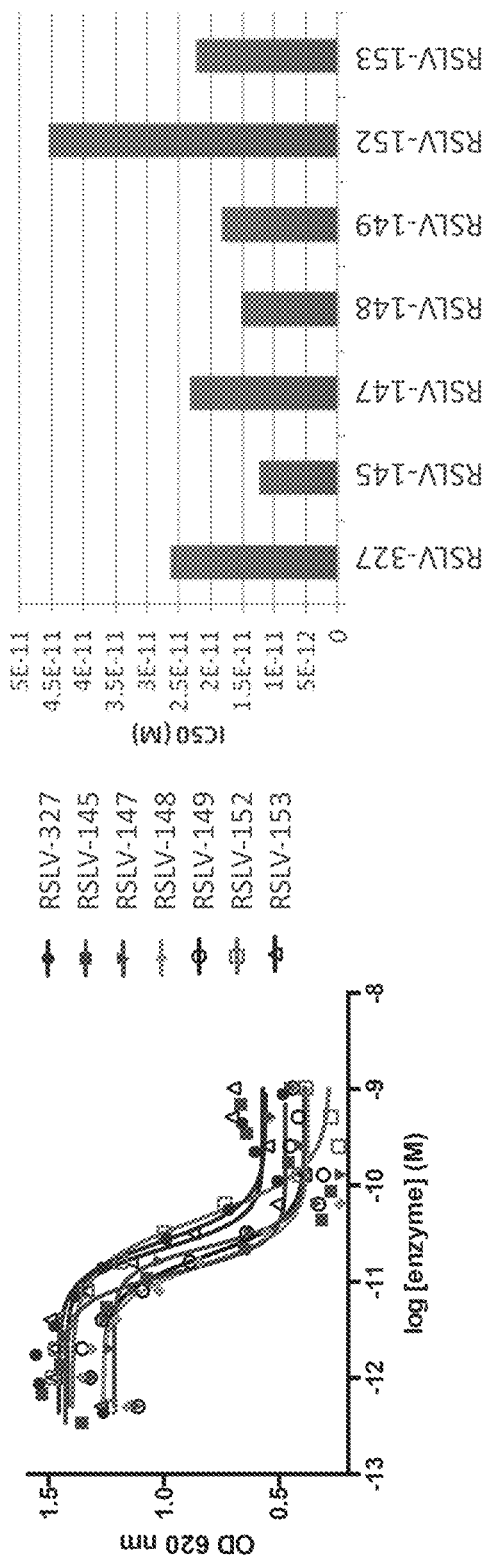
FIG. 3 shows DNase activity as measured by $OD_{620}$ (left) and $IC_{50}$ (right).

DNase1 activity of the optimized binuclease fusion proteins containing DNase1 domains was measured using ODN-2006-G5 (InvivoGen, tlrl-2006g5), a DNA oligonucleotide agonist of TLR9. The proteins, in dosages ranging from 0.24 ng/ml to 500 ng/ml) were incubated for 1 hour at 37° C. with ODN-2006-G5 in DMEM containing 25 mM Hepes and 10% FBS. The reaction mixtures were applied to hTLR9 HEKBlue cells, engineered to secrete alkaline phosphatase (SEAP) in response to TLR9 agonists, overnight at 37° C. The culture media was harvested and assayed for SEAP using a colormetric substrate and then read at $OD_{620}$. IC50 values were calculated using GraphPad Prism® version 6.0e software. Results are shown in FIG. 3. All 6 constructs (RSLV-145, RSLV-147, RSLV-148, RSLV-149, RSLV-152 and RSLV-153) possessed robust DNase activity and were at least 5000-fold more active than recombinant huDNase1. RSLV-145 appeared to be approximately 2× more active than other heterodimer constructs and RSLV-327, likely due to the 2 DNase domains in RSLV-145 compared to 1 DNase domain in the other constructs. RSLV-152 was consistently the least active of the constructs.

Example 4

Efficacy of Optimized Binuclease Fusion Proteins In Vitro

Effects of Optimized Binuclease Fusion Proteins on Cytokine Expression

Human PBMCs are isolated from normal patients and lupus patients and cultured. The cells are treated with various stimulatory TLR ligands, costimulatory antibodies, immune complexes, and normal or autoimmune sera, with or without the optimized binuclease fusion proteins of Example 2. Culture supernatant is collected at various time points (e.g., 6 hrs, 12 hrs, 24 hrs, 48 hrs, etc) and levels of a panel of cytokines, including human IL-6, IL-8, IL-10, IL-4, IFN-gamma, IFN-alpha and TNF-alpha are measured using commercially available ELISA kits from, e.g., Thermo Fisher Scientific, Inc. Effective optimized binuclease fusion proteins are expected to reduce the levels of cytokines produced by stimulated PBMCs relative to controls.

Effects of Optimized Binuclease Fusion Proteins on Lymphocyte Activation Receptor Expression Human PBMCs are isolated from normal patients and lupus patients and cultured. The cells are treated with various stimulatory TLR ligands, costimulatory antibodies, immune complexes, and normal or autoimmune sera, with or without the optimized binuclease fusion proteins of Example 2. Cells are then subjected to multi-color flow cytometry to measure the expression of lymphocyte activation receptors CD5, CD23, CD69, CD80, CD86, and CD25 at various time points (e.g., 6 hrs, 12 hrs, 24 hrs, 48 hrs, etc.) after stimulation using routine art-recognized methods. Suitable antibodies for these receptors are commercially available from, e.g., BD/PharMingen. Effective optimized binuclease fusion proteins are expected to reduce the expression of the lymphocyte activation receptors in stimulated PBMCs relative to controls.

Effects of Optimized Binuclease Fusion Proteins on Plasmacytoid Dendritic Cell (pDC) Interferon Output pDCs from healthy volunteers are isolated using art-recognized methods or commercially available kits, such as the EasySep™ Human EpCAM Positive Selection Kit (StemCell Technologies, Inc.). Isolated pDCs are cultured in, e.g., 96-well flat-bottom plates, at a densities ranging from $5 \times 10^4$ to $2.5 \times 10^5$/well in 0.1 ml in an appropriate medium (e.g., complete RPMI medium containing 10% FBS, 2 mM glutamine, 55 μM β-mercaptoethanol, 1 mM sodium pyruvate, 100 U/ml penicillin, and 100 μg/ml streptomycin). Cultured pDCs are activated by adding sera or plasma from individual SLE patients diluted with culture medium at a 1:5 ratio, and 0.1 ml of these samples are added to the cell-containing wells (final patient serum concentration is 10%). Cultures are incubated at 37° C. for 40 hr, after which the conditioned media is harvested and assessed for IFNα content using a commercially available ELISA kit. Serum samples obtained from healthy volunteers are used as controls. To assess the impact of the optimized binuclease fusion proteins, SLE patient sera or plasma is pretreated with the optimized binuclease fusion proteins (1-10 μg/ml) for 30 min and added to the pDC cultures. Effective optimized binuclease fusion proteins are expected to reduce the quantity of IFNα produced as a result of degrading the nucleic acid-containing ICs.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Sequence Table

| SEQ ID NO | Descriptioin | Sequence |
|---|---|---|
| 1 | RSLV-145 (DNase-NLG linker-RNase-Fc) amino acid sequence<br><br>Mature human DNase1 E13R/N74K/A114F/T205K (underlined)<br>NLG Linker (bold)<br>Mature human Rnase1 (bold underline)<br>Fc domain | LKIAAFNIQTFGRTKMSNATLVSYIVQILSRYDIALVQEV<br>RDSHLTAVGKLLDNLNQDAPDTYHYVVSEPLGRKSYKERY<br>LFVYRPDQVSAVDSYYYDDGCEPCGNDTFNREPFIVRFFS<br>RFTEVREFAIVPLHAAPGDAVAEIDALYDVYLDVQEKWGL<br>EDVMLMGDFNAGCSYVRPSQWSSIRLWTSPTFQWLIPDSA<br>DTTAKPTHCAYDRIVVAGMLLRGAVVPDSALPFNFQAAYG<br>LSDQLAQAISDHYPVEVMLKVDGASSPVNVSSPSVQDIKE<br>SRAKKFQRQHMDSDSSPSSSSTYCNQMMRRRNMTQGRCKP<br>VNTFVHEPLVDVQNVCFQEKVTCKNGQGNCYKSNSSMHIT<br>DCRLTNGSRYPNCAYRTSPKERHIIVACEGSPYVPVHFDA<br>SVEDSTEPKSSDKTHTCPPCPAPELLGGSSVFLFPPKPKD<br>TLMISRTPEVTCVVVDVSHEDPEVKFNWYVDGVEVHNAKT<br>KPREEQYNSTYRVVSVLTVLHQDWLNGKEYKCKVSNKALP |

| SEQ ID NO | Description | Sequence |
|---|---|---|
| | | ASIEKTISKAKGQPREPQVYTLPPSRDELTKNQVSLTCLV KGFYPSDIAVEWESNGQPENNYKTTPPVLDSDGSFFLYSK LTVDKSRWQQGNVFSCSVMHEALHNHYTQKSLSLSPGK |
| 2 | RSLV-146 (Fc-linker-RNase-NLG linker-DNase) amino acid sequence | DKTHTCPPCPAPELLGGSSVFLFPPKPKDTLMISRTPEVT CVVVDVSHEDPEVKFNWYVDGVEVHNAKTKPREEQYNSTY RVVSVLTVLHQDWLNGKEYKCKVSNKALPASIEKTISKAK GQPREPQVYTLPPSRDELTKNQVSLTCLVKGFYPSDIAVE WESNGQPENNYKTTPPVLDSDGSFFLYSKLTVDKSRWQQG NVFSCSVMHEALHNHYTQKSLSLSPGKGGGGSKESRAKKF QRQHMDSDSSPSSSSTYCNQMMRRRNMTQGRCKPVNTFVH EPLVDVQNVCFQEKVTCKNGQGNCYKSNSSMHITDCRLTN GSRYPNCAYRTSPKERHIIVACEGSPYVPVHFDASVEDST VDGASSPVNVSSPSVQDILKIAAFNIQTFGRTKMSNATLV SYIVQILSRYDIALVQEVRDSHLTAVGKLLDNLNQDAPDT YHYVVSEPLGRKSYKERYLFVYRPDQVSAVDSYYDDGCE PCGNDTFNREPFIVRFFSRFTEVREFAIVPLHAAPGDAVA EIDALYDVYLDVQEKWGLEDVMLMGDFNAGCSYVRPSQWS SIRLWTSPTFQWLIPDSADTTAKPTHCAYDRIVVAGMLLR GAVVPDSALPFNFQAAYGLSDQLAQAISDHYPVEVMLK |
| 3 | RSLV-147 DNase chain (Dnase-FcA) amino acid sequence | LKIAAFNIQTFGRTKMSNATLVSYIVQILSRYDIALVQEV RDSHLTAVGKLLDNLNQDAPDTYHYVVSEPLGRKSYKERY LFVYRPDQVSAVDSYYYDDGCEPCGNDTFNREPFIVRFFS RFTEVREFAIVPLHAAPGDAVAEIDALYDVYLDVQEKWGL EDVMLMGDFNAGCSYVRPSQWSSIRLWTSPTFQWLIPDSA DTTAKPTHCAYDRIVVAGMLLRGAVVPDSALPFNFQAAYG LSDQLAQAISDHYPVEVMLKEPKSSDKTHTCPPCPAPELL GGSSVFLFPPKPKDTLMISRTPEVTCVVVDVSHEDPEVKF NWYVDGVEVHNAKTKPREEQYNSTYRVVSVLTVLHQDWLN GKEYKCKVSNKALPASIEKTISKAKGQPREPQVYVYPPSR DELTKNQVSLTCLVKGFYPSDIAVEWESNGQPENNYKTTP PVLDSDGSFALVSKLTVDKSRWQQGNVFSCSVMHEALHNH YTQKSLSLSPGK |
| 4 | RSLV-147 RNase chain (RNase-FcB) amino acid sequence | KESRAKKFQRQHMDSDSSPSSSSTYCNQMMRRRNMTQGRC KPVNTFVHEPLVDVQNVCFQEKVTCKNGQGNCYKSNSSMH ITDCRLTNGSRYPNCAYRTSPKERHIIVACEGSPYVPVHF DASVEDSTEPKSSDKTHTCPPCPAPELLGGSSVFLFPPKP KDTLMISRTPEVTCVVVDVSHEDPEVKFNWYVDGVEVHNA KTKPREEQYNSTYRVVSVLTVLHQDWLNGKEYKCKVSNKA LPASIEKTISKAKGQPREPQVYVLPPSRDELTKNQVSLLC LVKGFYPSDIAVEWESNGQPENNYLTWPPVLDSDGSFFLY SKLTVDKSRWQQGNVFSCSVMHEALHNHYTQKSLSLSPGK |
| 5 | RSLV-148 (DNase-FcA-NLG linker-RNase) amino acid sequence | LKIAAFNIQTFGRTKMSNATLVSYIVQILSRYDIALVQEV RDSHLTAVGKLLDNLNQDAPDTYHYVVSEPLGRKSYKERY LFVYRPDQVSAVDSYYYDDGCEPCGNDTFNREPFIVRFFS RFTEVREFAIVPLHAAPGDAVAEIDALYDVYLDVQEKWGL EDVMLMGDFNAGCSYVRPSQWSSIRLWTSPTFQWLIPDSA DTTAKPTHCAYDRIVVAGMLLRGAVVPDSALPFNFQAAYG LSDQLAQAISDHYPVEVMLKEPKSSDKTHTCPPCPAPELL GGSSVFLFPPKPKDTLMISRTPEVTCVVVDVSHEDPEVKF NWYVDGVEVHNAKTKPREEQYNSTYRVVSVLTVLHQDWLN GKEYKCKVSNKALPASIEKTISKAKGQPREPQVYVYPPSR DELTKNQVSLTCLVKGFYPSDIAVEWESNGQPENNYKTTP PVLDSDGSFALVSKLTVDKSRWQQGNVFSCSVMHEALHNH YTQKSLSLSPGKVDGASSPVNVSSPSVQDIKESRAKKFQR QHMDSDSSPSSSSTYCNQMMRRRNMTQGRCKPVNTFVHEP LVDVQNVCFQEKVTCKNGQGNCYKSNSSMHITDCRLTNGS RYPNCAYRTSPKERHIIVACEGSPYVPVHFDASVEDST |
| 6 | RSLV-148 FcB chain amino acid sequence | DKTHTCPPCPAPELLGGSSVFLFPPKPKDTLMISRTPEVT CVVVDVSHEDPEVKFNWYVDGVEVHNAKTKPREEQYNSTY RVVSVLTVLHQDWLNGKEYKCKVSNKALPASIEKTISKAK GQPREPQVYVLPPSRDELTKNQVSLLCLVKGFYPSDIAVE WESNGQPENNYLTWPPVLDSDGSFFLYSKLTVDKSRWQQG NVFSCSVMHEALHNHYTQKSLSLSPGK |
| 7 | RSLV-149 DNase chain (DNase-Fc) amino acid sequence | LKIAAFNIQTFGRTKMSNATLVSYIVQILSRYDIALVQEV RDSHLTAVGKLLDNLNQDAPDTYHYVVSEPLGRKSYKERY LFVYRPDQVSAVDSYYYDDGCEPCGNDTFNREPFIVRFFS RFTEVREFAIVPLHAAPGDAVAEIDALYDVYLDVQEKWGL EDVMLMGDFNAGCSYVRPSQWSSIRLWTSPTFQWLIPDSA DTTAKPTHCAYDRIVVAGMLLRGAVVPDSALPFNFQAAYG |

-continued

Sequence Table

| SEQ ID NO | Descriptioin | Sequence |
|---|---|---|
| | | LSDQLAQAISDHYPVEVMLKEPKSSDKTHTCPPCPAPELL GGSSVFLFPPKPKDTLMISRTPEVTCVVVDVSHEDPEVKF NWYVDGVEVHNAKTKPREEQYNSTYRVVSVLTVLHQDWLN GKEYKCKVSNKALPASIEKTISKAKGQPREPQVYVYPPSR DELTKNQVSLTCLVKGFYPSDIAVEWESNGQPENNYKTTP PVLDSDGSFALVSKLTVDKSRWQQGNVFSCSVMHEALHNH YTQKSLSLSPGK |
| 8 | RSLV- 149 RNase chain (Fc-NLG-linker-RNase) amino acid sequence | DKTHTCPPCPAPELLGGSSVFLFPPKPKDTLMISRTPEVT CVVVDVSHEDPEVKFNWYVDGVEVHNAKTKPREEQYNSTY RVVSVLTVLHQDWLNGKEYKCKVSNKALPASIEKTISKAK GQPREPQVYVLPPSRDELTKNQVSLLCLVKGFYPSDIAVE WESNGQPENNYLTWPPVLDSDGSFFLYSKLTVDKSRWQQG NVFSCSVMHEALHNHYTQKSLSLSPGKVDGASSPVNVSSP SVQDIKESRAKKFQRQHMDSDSSPSSSSTYCNQMMRRRNM TQGRCKPVNTFVHEPLVDVQNVCFQEKVTCKNGQGNCYKS NSSMHITDCRLTNGSRYPNCAYRTSPKERHIIVACEGSPY VPVHFDASVEDST |
| 9 | RSLV- 150 DNase chain (FcA-NLG linker-DNase) amino acid sequence | EPKSCDKTHTCPPCPAPELLGGSSVFLFPPKPKDTLMISR TPEVTCVVVDVSHEDPEVKFNWYVDGVEVHNAKTKPREEQ YNSTYRVVSVLTVLHQDWLNGKEYKCKVSNKALPASIEKT ISKAKGQPREPQVYVYPPSRDELTKNQVSLTCLVKGFYPS DIAVEWESNGQPENNYKTTPPVLDSDGSFALVSKLTVDKS RWQQGNVFSCSVMHEALHNHYTQKSLSLSPGKVDGASSPV NVSSPSVQDILKIAAFNIQTFGRTKMSNATLVSYIVQILS RYDIALVQEVRDSHLTAVGKLLDNLNQDAPDTYHYVVSEP LGRKSYKERYLFVYRPDQVSAVDSYYYDDGCEPCGNDTFN REPFIVRFFSRFTEVREFAIVPLHAAPGDAVAEIDALYDV YLDVQEKWGLEDVMLMGDFNAGCSYVRPSQWSSIRLWTSP TFQWLIPDSADTTAKPTHCAYDRIVVAGMLLRGAVVPDSA LPFNFQAAYGLSDQLAQAISDHYPVEVMLK |
| 10 | RSLV-150 RNase chain (FcB-NLG linker-RNase) amino acid sequence | EPKSCDKTHTCPPCPAPELLGGSSVFLFPPKPKDTLMISR TPEVTCVVVDVSHEDPEVKFNWYVDGVEVHNAKTKPREEQ YNSTYRVVSVLTVLHQDWLNGKEYKCKVSNKALPASIEKT ISKAKGQPREPQVYVLPPSRDELTKNQVSLLCLVKGFYPS DIAVEWESNGQPENNYLTWPPVLDSDGSFFLYSKLTVDKS RWQQGNVFSCSVMHEALHNHYTQKSLSLSPGKVDGASSPV NVSSPSVQDIKESRAKKFQRQHMDSDSSPSSSSTYCNQMM RRRNMTQGRCKPVNTFVHEPLVDVQNVCFQEKVTCKNGQG NCYKSNSSMHITDCRLTNGSRYPNCAYRTSPKERHIIVAC EGSPYVPVHFDASVEDST |
| 11 | RSLV-151 DNase chain (Fc-NLG linker-DNase) amino acid sequence | DKTHTCPPCPAPELLGGSSVFLFPPKPKDTLMISRTPEVT CVVVDVSHEDPEVKFNWYVDGVEVHNAKTKPREEQYNSTY RVVSVLTVLHQDWLNGKEYKCKVSNKALPASIEKTISKAK GQPREPQVYVYPPSRDELTKNQVSLTCLVKGFYPSDIAVE WESNGQPENNYKTTPPVLDSDGSFALVSKLTVDKSRWQQG NVFSCSVMHEALHNHYTQKSLSLSPGKVDGASSPVNVSSP SVQDILKIAAFNIQTFGRTKMSNATLVSYIVQILSRYDIA LVQEVRDSHLTAVGKLLDNLNQDAPDTYHYVVSEPLGRKS YKERYLFVYRPDQVSAVDSYYYDDGCEPCGNDTFNREPFI VRFFSRFTEVREFAIVPLHAAPGDAVAEIDALYDVYLDVQ EKWGLEDVMLMGDFNAGCSYVRPSQWSSIRLWTSPTFQWL IPDSADTTAKPTHCAYDRIVVAGMLLRGAVVPDSALPFNF QAAYGLSDQLAQAISDHYPVEVMLK |
| 12 | RSLV-151 RNase chain (Fc-NLG linker-RNase) amino acid sequence | DKTHTCPPCPAPELLGGSSVFLFPPKPKDTLMISRTPEVT CVVVDVSHEDPEVKFNWYVDGVEVHNAKTKPREEQYNSTY RVVSVLTVLHQDWLNGKEYKCKVSNKALPASIEKTISKAK GQPREPQVYVLPPSRDELTKNQVSLLCLVKGFYPSDIAVE WESNGQPENNYLTWPPVLDSDGSFFLYSKLTVDKSRWQQG NVFSCSVMHEALHNHYTQKSLSLSPGKVDGASSPVNVSSP SVQDIKESRAKKFQRQHMDSDSSPSSSSTYCNQMMRRRNM TQGRCKPVNTFVHEPLVDVQNVCFQEKVTCKNGQGNCYKS NSSMHITDCRLTNGSRYPNCAYRTSPKERHIIVACEGSPY VPVHFDASVEDST |
| 13 | RSLV-152 (RNase-Fc-NLG) linker-DNase) amino acid sequence | KESRAKKFQRQHMDSDSSPSSSSTYCNQMMRRRNMTQGRC KPVNTFVHEPLVDVQNVCFQEKVTCKNGQGNCYKSNSSMH ITDCRLTNGSRYPNCAYRTSPKERHIIVACEGSPYVPVHF DASVEDSTEPKSSDKTHTCPPCPAPELLGGSSVFLFPPKP KDTLMISRTPEVTCVVVDVSHEDPEVKFNWYVDGVEVHNA KTKPREEQYNSTYRVVSVLTVLHQDWLNGKEYKCKVSNKA |

Sequence Table

| SEQ ID NO | Descriptioin | Sequence |
|---|---|---|
| | | LPASIEKTISKAKGQPREPQVYVYPPSRDELTKNQVSLTC LVKGFYPSDIAVEWESNGQPENNYKTTPPVLDSDGSFALV SKLTVDKSRWQQGNVFSCSVMHEALHNHYTQKSLSLSPGK VDGASSPVNVSSPSVQDILKIAAFNIQTFGRTKMSNATLV SYIVQILSRYDIALVQEVRDSHLTAVGKLLDNLNQDAPDT YHYVVSEPLGRKSYKERYLFVYRPDQVSAVDSYYYDDGCE PCGNDTFNREPFIVRFFSRFTEVREFAIVPLHAAPGDAVA EIDALYDVYLDVQEKWGLEDVMLMGDFNAGCSYVRPSQWS SIRLWTSPTFQWLIPDSADTTAKPTHCAYDRIVVAGMLLR GAVVPDSALPFNFQAAYGLSDQLAQAISDHYPVEVMLK |
| 14 | RSLV-152 Fc domain chain amino acid sequence | DKTHTCPPCPAPELLGGSSVFLFPPKPKDTLMISRTPEVT CVVVDVSHEDPEVKFNWYVDGVEVHNAKTKPREEQYNSTY RVVSVLTVLHQDWLNGKEYKCKVSNKALPASIEKTISKAK GQPREPQVYVLPPSRDELTKNQVSLLCLVKGFYPSDIAVE WESNGQPENNYLTWPPVLDSDGSFFLYSKLTVDKSRWQQG NVFSCSVMHEALHNHYTQKSLSLSPGK |
| 15 | RSLV-153 DNase chain (Fc-NLG linker-DNase) amino acid sequence | DKTHTCPPCPAPELLGGSSVFLFPPKPKDTLMISRTPEVT CVVVDVSHEDPEVKFNWYVDGVEVHNAKTKPREEQYNSTY RVVSVLTVLHQDWLNGKEYKCKVSNKALPASIEKTISKAK GQPREPQVYVYPPSRDELTKNQVSLTCLVKGFYPSDIAVE WESNGQPENNYKTTPPVLDSDGSFALVSKLTVDKSRWQQG NVFSCSVMHEALHNHYTQKSLSLSPGKVDGASSPVNVSSP SVQDILKIAAFNIQTFGRTKMSNATLVSYIVQILSRYDIA LVQEVRDSHLTAVGKLLDNLNQDAPDTYHYVVSEPLGRKS YKERYLFVYRPDQVSAVDSYYYDDGCEPCGNDTFNREPFI VRFFSRFTEVREFAIVPLHAAPGDAVAEIDALYDVYLDVQ EKWGLEDVMLMGDFNAGCSYVRPSQWSSIRLWTSPTFQWL IPDSADTTAKPTHCAYDRIVVAGMLLRGAVVPDSALPFNF QAAYGLSDQLAQAISDHYPVEVMLK |
| 16 | RSLV-153 RNase chain (RNase-Fc) amino acid sequence | KESRAKKFQRQHMDSDSSPSSSSTYCNQMMRRRNMTQGRC KPVNTFVHEPLVDVQNVCFQEKVTCKNGQGNCYKSNSSMH ITDCRLTNGSRYPNCAYRTSPKERHIIVACEGSPYVPVHF DASVEDSTEPKSSDKTHTCPPCPAPELLGGSSVFLFPPKP KDTLMISRTPEVTCVVVDVSHEDPEVKFNWYVDGVEVHNA KTKPREEQYNSTYRVVSVLTVLHQDWLNGKEYKCKVSNKA LPASIEKTISKAKGQPREPQVYVLPPSRDELTKNQVSLLC LVKGFYPSDIAVEWESNGQPENNYLTWPPVLDSDGSFFLY SKLTVDKSRWQQGNVFSCSVMHEALHNHYTQKSLSLSPGK |
| 17 | RSLV-154 (RNase-Fc-NLG linker-DNase) amino acid sequence | KESRAKKFQRQHMDSDSSPSSSSTYCNQMMRRRNMTQGRC KPVNTFVHEPLVDVQNVCFQEKVTCKNGQGNCYKSNSSMH ITDCRLTNGSRYPNCAYRTSPKERHIIVACEGSPYVPVHF DASVEDSTELLGGSSVFLFPPKPKDTLMISRTPEVTCVVV DVSHEDPEVKFNWYVDGVEVHNAKTKPREEQYNSTYRVVS VLTVLHQDWLNGKEYKCKVSNKALPASIEKTISKAKGQPR EPQVYTLPPSRDELTKNQVNLTCLVKGFYPSDIAVEWESN GQPENNYKTTPPVLDSDGSFFLNSTLTVDKSRWQQGNVFS CSVMHEALHNHYTQKSLSLSPGK**VDGASSPVNVSSPSVQD ILKIAAFNIQTFGRTKMSNATLVSYIVQILSRYDIALVQE VRDSHLTAVGKLLDNLNQDAPDTYHYVVSEPLGRKSYKER YLFVYRPDQVSAVDSYYYDDGCEPCGNDTFNREPFIVRFF SRFTEVREFAIVPLHAAPGDAVAEIDALYDVYLDVQEKWG LEDVMLMGDFNAGCSYVRPSQWSSIRLWTSPTFQWLIPDS ADTTAKPTHCAYDRIVVAGMLLRGAVVPDSALPFNFQAAY GLSDQLAQAISDHYPVEVMLK |
| 18 | Fc-NLG-linker-DNAse (control construct) | DKTHTCPPCPAPELLGGSSVFLFPPKPKDTLMISRTPEVT CVVVDVSHEDPEVKFNWYVDGVEVHNAKTKPREEQYNSTY RVVSVLTVLHQDWLNGKEYKCKVSNKALPASIEKTISKAK GQPREPQVYTLPPSRDELTKNQVSLTCLVKGFYPSDIAVE WESNGQPENNYKTTPPVLDSDGSFFLYSKLTVDKSRWQQG NVFSCSVMHEALHNHYTQKSLSLSPGKVDGASSPVNVSSP SVQDILKIAAFNIQTFGETKMSNATLVSYIVQILSRYDIA LVQEVRDSHLTAVGKLLDNLNQDAPDTYHYVVSEPLGRNS YKERYLFVYRPDQVSAVDSYYYDDGCEPCRNDTFNREPFI VRFFSRFTEVREFAIVPLHAAPGDAVAEIDALYDVYLDVQ EKWGLEDVMLMGDFNAGCSYVRPSQWSSIRLWTSPTFQWL IPDSADTTATPTHCAYDRIVVAGMLLRGAVVPDSALPFNF QAAYGLSDQLAQAISDHYPVEVMLK |

Sequence Table

| SEQ ID NO | Description | Sequence |
|---|---|---|
| 19 | DNASe-Fc (control construct) | LKIAAFNIQTFGRTKMSNATLVSYIVQILSRYDIALVQEV RDSHLTAVGKLLDNLNQDAPDTYHYVVSEPLGRKSYKERY LFVYRPDQVSAVDSYYYDDGCEPCGNDTFNREPFIVRFFS RFTEVREFAIVPLHAAPGDAVAEIDALYDVYLDVQEKWGL EDVMLMGDFNAGCSYVRPSQWSSIRLWTSPTFQWLIPDSA DTTAKPTHCAYDRIVVAGMLLRGAVVPDSALPFNFQAAYG LSDQLAQAISDHYPVEVMLKEPKSSDKTHTCPPCPAPELL GGSSVFLFPPKPKDTLMISRTPEVTCVVVDVSHEDPEVKF NWYVDGVEVHNAKTKPREEQYNSTYRVVSVLTVLHQDWLN GKEYKCKVSNKALPASIEKTISKAKGQPREPQVYTLPPSR DELTKNQVSLTCLVKGFYPSDIAVEWESNGQPENNYKTTP PVLDSDGSFFLYSKLTVDKSRWQQGNVFSCSVMHEALHNH YTQKSLSLSPGK |
| 20 | Mature wild type Human DNase1 | LKIAAFNIQTFGETKMSNATLVSYIVQILSRYDIALVQEV RDSHLTAVGKLLDNLNQDAPDTYHYVVSEPLGRNSYKERY LFVYRPDQVSAVDSYYYDDGCEPCGNDTFNREPAIVRFFS RFTEVREFAIVPLHAAPGDAVAEIDALYDVYLDVQEKWGL EDVMLMGDFNAGCSYVRPSQWSSIRLWTSPTFQWLIPDSA DTTATPTHCAYDRIVVAGMLLRGAVVPDSALPFNFQAAYG LSDQLAQAISDHYPVEVMLK |
| 21 | Mature human DNase1 A114F | LKIAAFNIQTFGETKMSNATLVSYIVQILSRYDIALVQEV RDSHLTAVGKLLDNLNQDAPDTYHYVVSEPLGRNSYKERY LFVYRPDQVSAVDSYYYDDGCEPCGNDTFNREPFIVRFFS RFTEVREFAIVPLHAAPGDAVAEIDALYDVYLDVQEKWGL EDVMLMGDFNAGCSYVRPSQWSSIRLWTSPTFQWLIPDSA DTTATPTHCAYDRIVVAGMLLRGAVVPDSALPFNFQAAYG LSDQLAQAISDHYPVEVMLK |
| 22 | Mature human DNase1 G105R | LKIAAFNIQTFGETKMSNATLVSYIVQILSRYDIALVQEV RDSHLTAVGKLLDNLNQDAPDTYHYVVSEPLGRNSYKERY LFVYRPDQVSAVDSYYYDDGCEPCRNDTFNREPAIVRFFS RFTEVREFAIVPLHAAPGDAVAEIDALYDVYLDVQEKWGL EDVMLMGDFNAGCSYVRPSQWSSIRLWTSPTFQWLIPDSA DTTATPTHCAYDRIVVAGMLLRGAVVPDSALPFNFQAAYG LSDQLAQAISDHYPVEVMLK |
| 23 | Precursor human DNase1 | MRGMKLLGALLALAALLQGAVSLKIAAFNIQTFGETKMSN ATLVSYIVQILSRYDIALVQEVRDSHLTAVGKLLDNLNQD APDTYHYVVSEPLGRNSYKERYLFVYRPDQVSAVDSYYYD DGCEPCGNDTFNREPAIVRFFSRFTEVREFAIVPLHAAPG DAVAEIDALYDVYLDVQEKWGLEDVMLMGDFNAGCSYVRP SQWSSIRLWTSPTFQWLIPDSADTTATPTHCAYDRIVVAG MLLRGAVVPDSALPFNFQAAYGLSDQLAQAISDHYPVEV MLK |
| 24 | Mature human DNase1 N18S/N106S/A114F | LKIAAFNIQTFGETKMSSATLVSYIVQILSRYDIALVQEV RDSHLTAVGKLLDNLNQDAPDTYHYVVSEPLGRNSYKERY LFVYRPDQVSAVDSYYYDDGCEPCGSDTFNREPFIVRFFS RFTEVREFAIVPLHAAPGDAVAEIDALYDVYLDVQEKWGL EDVMLMGDFNAGCSYVRPSQWSSIRLWTSPTFQWLIPDSA DTTATPTHCAYDRIVVAGMLLRGAVVPDSALPFNFQAAYG LSDQLAQAISDHYPVEVMLK |
| 25 | Mature human DNase1 E13R/N74K/A114F/ T205K | LKIAAFNIQTFGRTKMSNATLVSYIVQILSRYDIALVQEV RDSHLTAVGKLLDNLNQDAPDTYHYVVSEPLGRKSYKERY LFVYRPDQVSAVDSYYYDDGCEPCGNDTFNREPFIVRFFS RFTEVREFAIVPLHAAPGDAVAEIDALYDVYLDVQEKWGL EDVMLMGDFNAGCSYVRPSQWSSIRLWTSPTFQWLIPDSA DTTAKPTHCAYDRIVVAGMLLRGAVVPDSALPFNFQAAYG LSDQLAQAISDHYPVEVMLK |
| 26 | Mature human DNase1 E13R/N74K/A114F/ T205K/N18S/N106S | LKIAAFNIQTFGRTKMSSATLVSYIVQILSRYDIALVQEV RDSHLTAVGKLLDNLNQDAPDTYHYVVSEPLGRKSYKERY LFVYRPDQVSAVDSYYYDDGCEPCGSDTFNREPFIVRFFS RFTEVREFAIVPLHAAPGDAVAEIDALYDVYLDVQEKWGL EDVMLMGDFNAGCSYVRPSQWSSIRLWTSPTFQWLIPDSA DTTAKPTHCAYDRIVVAGMLLRGAVVPDSALPFNFQAAYG LSDQLAQAISDHYPVEVMLK |

-continued

Sequence Table

| SEQ ID NO | Description | Sequence |
|---|---|---|
| 27 | Mature human RNase1 | KESRAKKFQRQHMDSDSPSSSSTYCNQMMRRRNMTQGRC KPVNTFVHEPLVDVQNVCFQEKVTCKNGQGNCYKSNSSMH ITDCRLTNGSRYPNCAYRTSPKERHIIVACEGSPYVPVHF DASVEDST |
| 28 | Mature human RNase1 N34S/N76S/N88S | KESRAKKFQRQHMDSDSPSSSSTYCNQMMRRRSMTQGRC KPVNTFVHEPLVDVQNVCFQEKVTCKNGQGNCYKSSSSMH ITDCRLTSGSRYPNCAYRTSPKERHIIVACEGSPYVPVHF DASVEDST |
| 29 | Precursor human RNase1 | MALEKSLVRLLLLVLILLVLGWVQPSLGKESRAKKFQRQH MDSDSSPSSSSTYCNQMMRRRNMTQGRCKPVNTFVHEPLV DVQNVCFQEKVTCKNGQGNCYKSNSSMHITDCRLTNGSRY PNCAYRTSPKERHIIVACEGSPYVPVHFDASVEDST |
| 30 | (Gly$_4$Ser)3 linker | GGGGSGGGGSGGGGS |
| 31 | Gaussia luciferase signal peptide | MGVKVLFALICIAVAEA |
| 32 | Linker | LEA(EAAAK)$_4$ALEA(EAAAK)$_4$ |
| 33 | Q-linked glycosylation consensus | CXXGG-T/S-C |
| 34 | Q-linked glycosylation consensus | NST-E/D-A |
| 35 | Q-linked glycosylation consensus | NITQS |
| 36 | Q-linked glycosylation consensus | QSTQS |
| 37 | Q-linked glycosylation consensus | D/EFT-R/K-V |
| 38 | Q-linked glycosylation consensus | C-E/D-SN |
| 39 | Q-linked glycosylation consensus | GGSC-K/R |
| 40 | VK3 light chain signal peptide | METPAQLLFLLLLWLPDTTG |
| 41 | NLG linker | VDGASSPVNVSSPSVQDI |
| 42 | linker | LEA(EAAAK)$_4$ALEA(EAAAK)$_4$ALE |
| 43 | Linker | GGSG |
| 44 | Linker | GSAT |
| 45 | Human wild-type IgG1 Fc domain | EPKSCDKTHTCPPCPAPELLGGPSVFLFPPKPKDTLMISR TPEVTCVVVDVSHEDPEVKFNWYVDGVEVHNAKTKPREEQ YNSTYRVVSVLTVLHQDWLNGKEYKCKVSNKALPAPIEKT ISKAKGQPREPQVYTLPPSRDELTKNQVSLTCLVKGFYPS DIAVEWESNGQPENNYKTTPPVLDSDGSFFLYSKLTVDKS RWQQGNVFSCSVMHEALHNHYTQKSLSLSPGK |
| 46 | Mature human DNase1L3 | MRICSFNVRSFGESKQEDKNAMDVIVKVIKRCDIILVMEI KDSNNRICPILMEKLNRSRRGITYNYVISSRLGRNTYKE QYAFLYKEKLVSVKRSYHYHDYQDGDADVFSREPFVVWFQ SPHTAVKDFVIIPLHTTPETSVKEIDELVEVYTDVKHRWK AENFIFMGDFNAGCSYVPKKAWKNIRLRTDPRFVWLIGDQ |

-continued

Sequence Table

| SEQ ID NO | Description | Sequence |
|---|---|---|
| | | EDTTVKKSTNCAYDRIVLRGQEIVSSVVPKSNSVFDFQKA YKLTEEEALDVSDHFPVEFKLQSSRAFTNSKKSVTLRKKT KSKRS |
| 47 | Human Trex1 | MGPGARRQGRIVQGRPEMCFCPPPTPLPPLRILTLGTHTP TPCSSPGSAAGTYPTMGSQALPPGPMQTLIFFDMEATGLP FSQPKVTELCLLAVHRCALESPPTSQGPPPTVPPPPRVVD KLSLCVAPGKACSPAASEITGLSTAVLAAHGRQCFDDNLA NLLLAFLRRQPQPWCLVAHNGDRYDFPLLQAELAMLGLTS ALDGAFCVDSITALKALERASSPSEHGPRKSYSLGSIYTR LYGQSPPDSHTAEGDVLALLSICQWRPQALLRWVDAHARP FGTIRPMYGVTASARTKPRPSAVTTTAHLATTRNTSPSLG ESRGTKDLPPVKDPGALSREGLLAPLGLLAILTLAVATLY GLSLATPGE |
| 48 | Human DNase2 alpha (NP_001366.1) | MIPLLLAALLCVPAGALTCYGDSGQPVDWFVVYKLPALRG SGEAAQRGLQYKYLDESSGGWRDGRALINSPEGAVGRSLQ PLYRSNTSQLAFLLYNDQPPQPSKAQDSSMRGHTKGVLLL DHDGGFWLVHSVPNFPPPASSAAYSWPHSACTYGQTLLCV SFPFAQFSKMGKQLTYTYPWVYNYQLEGIFAQEFPDLENV VKGHHVSQEPWNSSITLTSQAGAVFQSFAKFSKFGDDLYS GWLAAALGTNLQVQFWHKTVGILPSNCSDIWQVLNVNQIA FPGPAGPSFNSTEDHSKWCVSPKGPWTCVGDMNRNQGEEQ RGGGTLCAQLPALWKAFQPLVKNYQPCNGMARKPSRAYKI |
| 49 | human DNase2 beta | MKQKMMARLLRTSFALLFLGLFGVLGAATISCRNEEGKAV DWFTFYKLPKRQNKESGETGLEYLYLDSTTRSWRKSEQLM NDTKSVLGRTLQQLYEAYASKSNNTAYLIYNDGVPKPVNY SRKYGHTKGLLLWNRVQGFWLIHSIPQFPPIPEEGYDYPP TGRRNGQSGICITFKYNQYEAIDSQLLVCNPNVYSCSIPA TFHQELIHMPQLCTRASSSEIPGRLLTTLQSAQGQKFLHF AKSDSFLDDIFAAWMAQRLKTHLLTETWQRKRQELPSNCS LPYHVYNIKAIKLSRHSYFSSYQDHAKWCISQKGTKNRWT CIGDLNRSPHQAFRSGGFICTQNWQIYQAFQGLVLYYESC K |
| 50 | Fc region N83S | EPKSCDKTHTCPPCPAPELLGGPSVFLFPPKPKDTLMISR TPEVTCVVVDVSHEDPEVKFNWYVDGVEVHNAKTKPREEQ YSSTYRVVSVLTVLHQDWLNGKEYKCKVSNKALPAPIEKT ISKAKGQPREPQVYTLPPSRDELTKNQVSLTCLVKGFYPS DIAVEWESNGQPENNYKTTPPVLDSDGSFFLYSKLTVDKS RWQQGNVFSCSVMHEALHNHYTQKSLSLSPGK |
| 51 | Fc region with SCC | EPKSSDKTHTCPPCPAPELLGGPSVFLFPPKPKDTLMISR TPEVTCVVVDVSHEDPEVKFNWYVDGVEVHNAKTKPREEQ YNSTYRVVSVLTVLHQDWLNGKEYKCKVSNKALPAPIEKT ISKAKGQPREPQVYTLPPSRDELTKNQVSLTCLVKGFYPS DIAVEWESNGQPENNYKTTPPVLDSDGSFFLYSKLTVDKS RWQQGNVFSCSVMHEALHNHYTQKSLSLSPGK |
| 52 | Fc region with SSS | EPKSSDKTHTSPPSPAPELLGGPSVFLFPPKPKDTLMISR TPEVTCVVVDVSHEDPEVKFNWYVDGVEVHNAKTKPREEQ YNSTYRVVSVLTVLHQDWLNGKEYKCKVSNKALPAPIEKT ISKAKGQPREPQVYTLPPSRDELTKNQVSLTCLVKGFYPS DIAVEWESNGQPENNYKTTPPVLDSDGSFFLYSKLTVDKS RWQQGNVFSCSVMHEALHNHYTQKSLSLSPGK |
| 53 | Linker | LEA(EAAAK)$_4$ALEA(EAAAK)$_4$ALE |
| 54 | VK3LP leader | METPAQLLFLLLLWLPDTTG |
| 55 | Fc region with SCC, P238S, P331S mutations | EPKSSDKTHTSPPSPAPELLGGSSVFLFPPKPKDTLMISR TPEVTCVVVDVSHEDPEVKFNWYVDGVEVHNAKTKPREEQ YNSTYRVVSVLTVLHQDWLNGKEYKCKVSNKALPASIEKT ISKAKGQPREPQVYTLPPSRDELTKNQVSLTCLVKGFYPS DIAVEWESNGQPENNYKTTPPVLDSDGSFFLYSKLTVDKS RWQQGNVFSCSVMHEALHNHYTQKSLSLSPGK |
| 56 | Fc region with P238S, P331S mutations | EPKCSDKTHTSPPSPAPELLGGSSVFLFPPKPKDTLMISR TPEVTCVVVDVSHEDPEVKFNWYVDGVEVHNAKTKPREEQ YNSTYRVVSVLTVLHQDWLNGKEYKCKVSNKALPASIEKT ISKAKGQPREPQVYTLPPSRDELTKNQVSLTCLVKGFYPS DIAVEWESNGQPENNYKTTPPVLDSDGSFFLYSKLTVDKS RWQQGNVFSCSVMHEALHNHYTQKSLSLSPGK |

Sequence Table

| SEQ ID NO | Description | Sequence |
|---|---|---|
| 57 | RSLV-327 (RNase-linker-HSA-linker-DNase E13R/N74K/A114F/T205K) | METPAQLLFLLLLWLPDTTGKESRAKKFQRQHMDSDSPS SSSTYCNQMMRRRNMTQGRCKPVNTFVHEPLVDVQNVCFQ EKVTCKNGQGNCYKSNSSMHITDCRLTNGSRYPNCAYRTS PKERHIIVACEGSPYVPVHFDASVEDSTGGGGSGGGGSGG GGSDAHKSEVAHRFKDLGEENFKALVLIAFAQYLQQCPFE DHVKLVNEVTEFAKTCVADESAENCDKSLHTLFGDKLCTV ATLRETYGEMADCCAKQEPERNECFLQHKDDNPNLPRLVR PEVDVMCTAFHDNEETFLKKYLYEIARRHPYFYAPELLFF AKRYKAAFTECCQAADKAACLLPKLDELRDEGKASSAKQR LKCASLQKFGERAFKAWAVARLSQRFPKAEFAEVSKLVTD LTKVHTECCHGDLLECADDRADLAKYICENQDSISSKLKE CCEKPLLEKSHCIAEVENDEMPADLPSLAADFVESKDVCK NYAEAKDVFLGMFLYEYARRHPDYSVVLLLRLAKTYETTL EKCCAAADPHECYAKVFDEFKPLVEEPQNLIKQNCELFEQ LGEYKFQNALLVRYTKKVPQVSTPTLVEVSRNLGKVGSKC CKHPEAKRMPCAEDYLSVVLNQLCVLHEKTPVSDRVTKCC TESLVNRRPCFSALEVDETYVPKEFNAETFTFHADICTLS EKERQIKKQTALVELVKHKPKATKEQLKAVMDDFAAFVEK CCKADDKETCFAEEGKKLVAASQAALGLGGGGSGGGGSGG GGSLKIAAFNIQTFGRTKMSNATLVSYIVQILSRYDIALV QEVRDSHLTAVGKLLDNLNQDAPDTYHYVVSEPLGRKSYK ERYLFVYRPDQVSAVDSYYYDDGCEPCGNDTFNREPFIVR FFSRFTEVREFAIVPLHAAPGDAVAEIDALYDVYLDVQEK WGLEDVMLMGDFNAGCSYVRPSQWSSIRLWTSPTFQWLIP DSADTTAKPTHCAYDRIVVAGMLLRGAVVPDSALPFNFQA AYGLSDQLAQAISDHYPVEVMLK |

We claim:

1. A polypeptide comprising a first nuclease domain, a second nuclease domain, and an Fc domain, wherein the first nuclease domain is human DNase1 and the second nuclease domain is human RNase1, wherein the human DNase1 is operably linked with or without a linker in tandem from N- to C-terminus to the human RNase1, and wherein the human RNase1 is operably linked with or without a linker to the Fc domain, wherein the polypeptide comprises an amino acid sequence at least 90% identical to the amino acid sequence of SEQ ID NO:1.

2. The polypeptide of claim 1, comprising an amino acid sequence at least 95% identical to the amino acid sequence of SEQ ID NO: 1.

3. The polypeptide of claim 1, comprising an amino acid sequence at least 96% identical to the amino acid sequence of SEQ ID NO: 1.

4. The polypeptide of claim 1, comprising an amino acid sequence at least 97% identical to the amino acid sequence of SEQ ID NO: 1.

5. The polypeptide of claim 1, comprising an amino acid sequence at least 98% identical to the amino acid sequence of SEQ ID NO: 1.

6. The polypeptide of claim 1, comprising an amino acid sequence at least 99% identical to the amino acid sequence of SEQ ID NO: 1.

7. A polypeptide comprising the amino acid sequence of SEQ ID NO: 1.

8. A homodimer comprising the polypeptide sequence of claim 1.

9. A homodimer comprising the polypeptide sequence of claim 2.

10. A homodimer comprising the polypeptide sequence of claim 3.

11. A homodimer comprising the polypeptide sequence of claim 4.

12. A homodimer comprising the polypeptide sequence of claim 5.

13. A homodimer comprising the polypeptide sequence of claim 6.

14. A homodimer comprising the polypeptide sequence of claim 7.

15. A composition comprising the polypeptide of claim 1, and a pharmaceutically acceptable carrier.

16. A composition comprising the polypeptide of claim 2, and a pharmaceutically acceptable carrier.

17. A composition comprising the polypeptide of claim 3, and a pharmaceutically acceptable carrier.

18. A composition comprising the polypeptide of claim 4, and a pharmaceutically acceptable carrier.

19. A composition comprising the polypeptide of claim 5, and a pharmaceutically acceptable carrier.

20. A composition comprising the polypeptide of claim 6, and a pharmaceutically acceptable carrier.

21. A composition comprising the polypeptide of claim 7, and a pharmaceutically acceptable carrier.

22. A composition comprising the homodimer of claim 8, and a pharmaceutically acceptable carrier.

23. A composition comprising the homodimer of claim 9, and a pharmaceutically acceptable carrier.

24. A composition comprising the homodimer of claim 10, and a pharmaceutically acceptable carrier.

25. A composition comprising the homodimer of claim 11, and a pharmaceutically acceptable carrier.

26. A composition comprising the homodimer of claim 12, and a pharmaceutically acceptable carrier.

27. A composition comprising the homodimer of claim 13, and a pharmaceutically acceptable carrier.

28. A composition comprising the homodimer of claim 14, and a pharmaceutically acceptable carrier.

* * * * *

UNITED STATES PATENT AND TRADEMARK OFFICE
CERTIFICATE OF CORRECTION

PATENT NO. : 12,077,790 B2
APPLICATION NO. : 17/560522
DATED : September 3, 2024
INVENTOR(S) : James Arthur Posada et al.

Page 1 of 1

It is certified that error appears in the above-identified patent and that said Letters Patent is hereby corrected as shown below:

On the Title Page

Item (71) In the Applicant section, please delete:
"Resolve Therapeutics, LLC, St. Petersburg, FL (US)"
And replace with:
--Resolve Therapeutics, LLC, Miami, FL (US)--

Item (72) In the Inventor section, please delete:
"James Arthur Posada, St. Petersburg, FL (US)"
And replace with:
--James Arthur Posada, Miami, FL (US)--

Signed and Sealed this
Eighth Day of October, 2024

Katherine Kelly Vidal
*Director of the United States Patent and Trademark Office*

SEQUENCE LISTING

<160> NUMBER OF SEQ ID NOS: 70

<210> SEQ ID NO 1
<211> LENGTH: 638
<212> TYPE: PRT
<213> ORGANISM: Artificial Sequence
<220> FEATURE:
<223> OTHER INFORMATION: Synthetic: RSLV-145 (DNase-NLG linker-RNase-Fc) amino acid sequence

<400> SEQUENCE: 1

```
Leu Lys Ile Ala Ala Phe Asn Ile Gln Thr Phe Gly Arg Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Lys Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160
```

-continued

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
                180                 185                 190

Gln Trp Leu Ile Pro Asp Ser Ala Asp Thr Thr Ala Lys Pro Thr His
                195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys Val Asp Gly Ala Ser Ser Pro Val Asn Val Ser Ser
                260                 265                 270

Pro Ser Val Gln Asp Ile Lys Glu Ser Arg Ala Lys Lys Phe Gln Arg
                275                 280                 285

Gln His Met Asp Ser Asp Ser Ser Pro Ser Ser Ser Thr Tyr Cys
                290                 295                 300

Asn Gln Met Met Arg Arg Arg Asn Met Thr Gln Gly Arg Cys Lys Pro
305                 310                 315                 320

Val Asn Thr Phe Val His Glu Pro Leu Val Asp Val Gln Asn Val Cys
                325                 330                 335

Phe Gln Glu Lys Val Thr Cys Lys Asn Gly Gln Gly Asn Cys Tyr Lys
                340                 345                 350

Ser Asn Ser Ser Met His Ile Thr Asp Cys Arg Leu Thr Asn Gly Ser
                355                 360                 365

Arg Tyr Pro Asn Cys Ala Tyr Arg Thr Ser Pro Lys Glu Arg His Ile
    370                 375                 380

Ile Val Ala Cys Glu Gly Ser Pro Tyr Val Pro Val His Phe Asp Ala
385                 390                 395                 400

Ser Val Glu Asp Ser Thr Glu Pro Lys Ser Ser Asp Lys Thr His Thr
                405                 410                 415

Cys Pro Pro Cys Pro Ala Pro Glu Leu Leu Gly Gly Ser Ser Val Phe
                420                 425                 430

Leu Phe Pro Pro Lys Pro Lys Asp Thr Leu Met Ile Ser Arg Thr Pro
                435                 440                 445

Glu Val Thr Cys Val Val Val Asp Val Ser His Glu Asp Pro Glu Val
                450                 455                 460

Lys Phe Asn Trp Tyr Val Asp Gly Val Glu Val His Asn Ala Lys Thr
465                 470                 475                 480

Lys Pro Arg Glu Glu Gln Tyr Asn Ser Thr Tyr Arg Val Val Ser Val
                485                 490                 495

Leu Thr Val Leu His Gln Asp Trp Leu Asn Gly Lys Glu Tyr Lys Cys
                500                 505                 510

Lys Val Ser Asn Lys Ala Leu Pro Ala Ser Ile Glu Lys Thr Ile Ser
                515                 520                 525

Lys Ala Lys Gly Gln Pro Arg Glu Pro Gln Val Tyr Thr Leu Pro Pro
                530                 535                 540

Ser Arg Asp Glu Leu Thr Lys Asn Gln Val Ser Leu Thr Cys Leu Val
545                 550                 555                 560

Lys Gly Phe Tyr Pro Ser Asp Ile Ala Val Glu Trp Glu Ser Asn Gly
                565                 570                 575

Gln Pro Glu Asn Asn Tyr Lys Thr Thr Pro Pro Val Leu Asp Ser Asp

```
                    580                 585                 590
Gly Ser Phe Phe Leu Tyr Ser Lys Leu Thr Val Asp Lys Ser Arg Trp
            595                 600                 605

Gln Gln Gly Asn Val Phe Ser Cys Ser Val Met His Glu Ala Leu His
        610                 615                 620

Asn His Tyr Thr Gln Lys Ser Leu Ser Leu Ser Pro Gly Lys
625                 630                 635
```

<210> SEQ ID NO 2
<211> LENGTH: 638
<212> TYPE: PRT
<213> ORGANISM: Artificial Sequence
<220> FEATURE:
<223> OTHER INFORMATION: Synthetic: RSLV-146 (Fc-linker-RNase-NLG linker-DNase) amino acid sequence

<400> SEQUENCE: 2

```
Asp Lys Thr His Thr Cys Pro Pro Cys Pro Ala Pro Glu Leu Leu Gly
1               5                   10                  15

Gly Ser Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Ser Lys Glu Ser Arg Ala Lys Lys Phe
225                 230                 235                 240

Gln Arg Gln His Met Asp Ser Asp Ser Ser Pro Ser Ser Ser Ser Thr
                245                 250                 255

Tyr Cys Asn Gln Met Met Arg Arg Arg Asn Met Thr Gln Gly Arg Cys
            260                 265                 270

Lys Pro Val Asn Thr Phe Val His Glu Pro Leu Val Asp Val Gln Asn
        275                 280                 285

Val Cys Phe Gln Glu Lys Val Thr Cys Lys Asn Gly Gln Gly Asn Cys
    290                 295                 300
```

Tyr Lys Ser Asn Ser Ser Met His Ile Thr Asp Cys Arg Leu Thr Asn
305                 310                 315                 320

Gly Ser Arg Tyr Pro Asn Cys Ala Tyr Arg Thr Ser Pro Lys Glu Arg
            325                 330                 335

His Ile Ile Val Ala Cys Glu Gly Ser Pro Tyr Val Pro Val His Phe
        340                 345                 350

Asp Ala Ser Val Glu Asp Ser Thr Val Asp Gly Ala Ser Ser Pro Val
    355                 360                 365

Asn Val Ser Ser Pro Ser Val Gln Asp Ile Leu Lys Ile Ala Ala Phe
370                 375                 380

Asn Ile Gln Thr Phe Gly Arg Thr Lys Met Ser Asn Ala Thr Leu Val
385                 390                 395                 400

Ser Tyr Ile Val Gln Ile Leu Ser Arg Tyr Asp Ile Ala Leu Val Gln
                405                 410                 415

Glu Val Arg Asp Ser His Leu Thr Ala Val Gly Lys Leu Leu Asp Asn
            420                 425                 430

Leu Asn Gln Asp Ala Pro Asp Thr Tyr His Tyr Val Val Ser Glu Pro
        435                 440                 445

Leu Gly Arg Lys Ser Tyr Lys Glu Arg Tyr Leu Phe Val Tyr Arg Pro
    450                 455                 460

Asp Gln Val Ser Ala Val Asp Ser Tyr Tyr Asp Asp Gly Cys Glu
465                 470                 475                 480

Pro Cys Gly Asn Asp Thr Phe Asn Arg Glu Pro Phe Ile Val Arg Phe
                485                 490                 495

Phe Ser Arg Phe Thr Glu Val Arg Glu Phe Ala Ile Val Pro Leu His
            500                 505                 510

Ala Ala Pro Gly Asp Ala Val Ala Glu Ile Asp Ala Leu Tyr Asp Val
        515                 520                 525

Tyr Leu Asp Val Gln Glu Lys Trp Gly Leu Glu Asp Val Met Leu Met
    530                 535                 540

Gly Asp Phe Asn Ala Gly Cys Ser Tyr Val Arg Pro Ser Gln Trp Ser
545                 550                 555                 560

Ser Ile Arg Leu Trp Thr Ser Pro Thr Phe Gln Trp Leu Ile Pro Asp
                565                 570                 575

Ser Ala Asp Thr Thr Ala Lys Pro Thr His Cys Ala Tyr Asp Arg Ile
            580                 585                 590

Val Val Ala Gly Met Leu Leu Arg Gly Ala Val Val Pro Asp Ser Ala
        595                 600                 605

Leu Pro Phe Asn Phe Gln Ala Ala Tyr Gly Leu Ser Asp Gln Leu Ala
    610                 615                 620

Gln Ala Ile Ser Asp His Tyr Pro Val Glu Val Met Leu Lys
625                 630                 635

<210> SEQ ID NO 3
<211> LENGTH: 492
<212> TYPE: PRT
<213> ORGANISM: Artificial Sequence
<220> FEATURE:
<223> OTHER INFORMATION: Synthetic: RSLV-147 DNase chain (Dnase-FcA)
      amino acid sequence

<400> SEQUENCE: 3

Leu Lys Ile Ala Ala Phe Asn Ile Gln Thr Phe Gly Arg Thr Lys Met
1               5                   10                  15

Ser Asn Ala Thr Leu Val Ser Tyr Ile Val Gln Ile Leu Ser Arg Tyr
                20                  25                  30

```
Asp Ile Ala Leu Val Gln Glu Val Arg Asp Ser His Leu Thr Ala Val
         35                  40                  45

Gly Lys Leu Leu Asp Asn Leu Asn Gln Asp Ala Pro Asp Thr Tyr His
 50                  55                  60

Tyr Val Val Ser Glu Pro Leu Gly Arg Lys Ser Tyr Lys Glu Arg Tyr
 65                  70                  75                  80

Leu Phe Val Tyr Arg Pro Asp Gln Val Ser Ala Val Asp Ser Tyr Tyr
                 85                  90                  95

Tyr Asp Asp Gly Cys Glu Pro Cys Gly Asn Asp Thr Phe Asn Arg Glu
                100                 105                 110

Pro Phe Ile Val Arg Phe Ser Arg Phe Thr Glu Val Arg Glu Phe
        115                 120                 125

Ala Ile Val Pro Leu His Ala Ala Pro Gly Asp Ala Val Ala Glu Ile
        130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
                180                 185                 190

Gln Trp Leu Ile Pro Asp Ser Ala Asp Thr Thr Ala Lys Pro Thr His
                195                 200                 205

Cys Ala Tyr Asp Arg Ile Val Val Ala Gly Met Leu Leu Arg Gly Ala
        210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys Glu Pro Lys Ser Ser Asp Lys Thr His Thr Cys Pro
                260                 265                 270

Pro Cys Pro Ala Pro Glu Leu Leu Gly Gly Ser Ser Val Phe Leu Phe
        275                 280                 285

Pro Pro Lys Pro Lys Asp Thr Leu Met Ile Ser Arg Thr Pro Glu Val
        290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
                340                 345                 350

Val Leu His Gln Asp Trp Leu Asn Gly Lys Glu Tyr Lys Cys Lys Val
        355                 360                 365

Ser Asn Lys Ala Leu Pro Ala Ser Ile Glu Lys Thr Ile Ser Lys Ala
        370                 375                 380

Lys Gly Gln Pro Arg Glu Pro Gln Val Tyr Val Tyr Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
                420                 425                 430

Glu Asn Asn Tyr Lys Thr Thr Pro Pro Val Leu Asp Ser Asp Gly Ser
        435                 440                 445
```

```
Phe Ala Leu Val Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 4
<211> LENGTH: 360
<212> TYPE: PRT
<213> ORGANISM: Artificial Sequence
<220> FEATURE:
<223> OTHER INFORMATION: Synthetic: RSLV-147 RNase chain (RNase-FcB)
      amino acid sequence

<400> SEQUENCE: 4

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
                20                  25                  30

Arg Asn Met Thr Gln Gly Arg Cys Lys Pro Val Asn Thr Phe Val His
            35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125

Glu Pro Lys Ser Ser Asp Lys Thr His Thr Cys Pro Pro Cys Pro Ala
    130                 135                 140

Pro Glu Leu Leu Gly Gly Ser Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Ser Ile Glu Lys Thr Ile Ser Lys Ala Lys Gly Gln Pro
                245                 250                 255

Arg Glu Pro Gln Val Tyr Val Leu Pro Pro Ser Arg Asp Glu Leu Thr
            260                 265                 270

Lys Asn Gln Val Ser Leu Leu Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Leu Thr Trp Pro Pro Val Leu Asp Ser Asp Gly Ser Phe Phe Leu Tyr
305                 310                 315                 320
```

```
Ser Lys Leu Thr Val Asp Lys Ser Arg Trp Gln Gln Gly Asn Val Phe
            325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 5
<211> LENGTH: 638
<212> TYPE: PRT
<213> ORGANISM: Artificial Sequence
<220> FEATURE:
<223> OTHER INFORMATION: Synthetic: RSLV-148 (DNase-FcA-NLG linker-
      RNase) amino acid sequence

<400> SEQUENCE: 5

Leu Lys Ile Ala Ala Phe Asn Ile Gln Thr Phe Gly Arg Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Lys Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Lys Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys Glu Pro Lys Ser Ser Asp Lys Thr His Thr Cys Pro
            260                 265                 270

Pro Cys Pro Ala Pro Glu Leu Leu Gly Gly Ser Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
```

```
            305                 310                 315                 320
Asn Trp Tyr Val Asp Gly Val Glu Val His Asn Ala Lys Thr Lys Pro
                    325                 330                 335
Arg Glu Glu Gln Tyr Asn Ser Thr Tyr Arg Val Val Ser Val Leu Thr
                    340                 345                 350
Val Leu His Gln Asp Trp Leu Asn Gly Lys Glu Tyr Lys Cys Lys Val
                    355                 360                 365
Ser Asn Lys Ala Leu Pro Ala Ser Ile Glu Lys Thr Ile Ser Lys Ala
            370                 375                 380
Lys Gly Gln Pro Arg Glu Pro Gln Val Tyr Val Tyr Pro Pro Ser Arg
385                 390                 395                 400
Asp Glu Leu Thr Lys Asn Gln Val Ser Leu Thr Cys Leu Val Lys Gly
                    405                 410                 415
Phe Tyr Pro Ser Asp Ile Ala Val Glu Trp Glu Ser Asn Gly Gln Pro
                    420                 425                 430
Glu Asn Asn Tyr Lys Thr Thr Pro Pro Val Leu Asp Ser Asp Gly Ser
                    435                 440                 445
Phe Ala Leu Val Ser Lys Leu Thr Val Asp Lys Ser Arg Trp Gln Gln
            450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Val Asp Gly Ala
                    485                 490                 495
Ser Ser Pro Val Asn Val Ser Ser Pro Ser Val Gln Asp Ile Lys Glu
                    500                 505                 510
Ser Arg Ala Lys Lys Phe Gln Arg Gln His Met Asp Ser Asp Ser Ser
            515                 520                 525
Pro Ser Ser Ser Ser Thr Tyr Cys Asn Gln Met Met Arg Arg Arg Asn
            530                 535                 540
Met Thr Gln Gly Arg Cys Lys Pro Val Asn Thr Phe Val His Glu Pro
545                 550                 555                 560
Leu Val Asp Val Gln Asn Val Cys Phe Gln Glu Lys Val Thr Cys Lys
                    565                 570                 575
Asn Gly Gln Gly Asn Cys Tyr Lys Ser Asn Ser Ser Met His Ile Thr
                    580                 585                 590
Asp Cys Arg Leu Thr Asn Gly Ser Arg Tyr Pro Asn Cys Ala Tyr Arg
            595                 600                 605
Thr Ser Pro Lys Glu Arg His Ile Ile Val Ala Cys Glu Gly Ser Pro
            610                 615                 620
Tyr Val Pro Val His Phe Asp Ala Ser Val Glu Asp Ser Thr
625                 630                 635

<210> SEQ ID NO 6
<211> LENGTH: 227
<212> TYPE: PRT
<213> ORGANISM: Artificial Sequence
<220> FEATURE:
<223> OTHER INFORMATION: Synthetic: RSLV-148 FcB chain amino acid
      sequence

<400> SEQUENCE: 6

Asp Lys Thr His Thr Cys Pro Pro Cys Pro Ala Pro Glu Leu Leu Gly
1               5                   10                  15
Gly Ser Ser Val Phe Leu Phe Pro Pro Lys Pro Lys Asp Thr Leu Met
                    20                  25                  30
```

```
Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Val Leu Pro Pro Ser Arg Asp Glu Leu Thr Lys Asn Gln Val Ser
130                 135                 140

Leu Leu Cys Leu Val Lys Gly Phe Tyr Pro Ser Asp Ile Ala Val Glu
145                 150                 155                 160

Trp Glu Ser Asn Gly Gln Pro Glu Asn Asn Tyr Leu Thr Trp Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 7
<211> LENGTH: 492
<212> TYPE: PRT
<213> ORGANISM: Artificial Sequence
<220> FEATURE:
<223> OTHER INFORMATION: Synthetic: RSLV-149 DNase chain (DNase-Fc)
      amino acid sequence

<400> SEQUENCE: 7

Leu Lys Ile Ala Ala Phe Asn Ile Gln Thr Phe Gly Arg Thr Lys Met
 1               5                  10                  15

Ser Asn Ala Thr Leu Val Ser Tyr Ile Val Gln Ile Leu Ser Arg Tyr
                20                  25                  30

Asp Ile Ala Leu Val Gln Glu Val Arg Asp Ser His Leu Thr Ala Val
            35                  40                  45

Gly Lys Leu Leu Asp Asn Leu Asn Gln Asp Ala Pro Asp Thr Tyr His
        50                  55                  60

Tyr Val Val Ser Glu Pro Leu Gly Arg Lys Ser Tyr Lys Glu Arg Tyr
 65                  70                  75                  80

Leu Phe Val Tyr Arg Pro Asp Gln Val Ser Ala Val Asp Ser Tyr Tyr
                 85                  90                  95

Tyr Asp Asp Gly Cys Glu Pro Cys Gly Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
130                 135                 140

Asp Ala Leu Tyr Asp Val Tyr Leu Asp Val Gln Glu Lys Trp Gly Leu
145                 150                 155                 160
```

Glu Asp Val Met Leu Met Gly Asp Phe Asn Ala Gly Cys Ser Tyr Val
            165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Lys Pro Thr His
            195                 200                 205

Cys Ala Tyr Asp Arg Ile Val Val Ala Gly Met Leu Leu Arg Gly Ala
            210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
            245                 250                 255

Val Met Leu Lys Glu Pro Lys Ser Ser Asp Lys Thr His Thr Cys Pro
            260                 265                 270

Pro Cys Pro Ala Pro Glu Leu Leu Gly Gly Ser Ser Val Phe Leu Phe
            275                 280                 285

Pro Pro Lys Pro Lys Asp Thr Leu Met Ile Ser Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
            325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
            355                 360                 365

Ser Asn Lys Ala Leu Pro Ala Ser Ile Glu Lys Thr Ile Ser Lys Ala
            370                 375                 380

Lys Gly Gln Pro Arg Glu Pro Gln Val Tyr Val Tyr Pro Pro Ser Arg
385                 390                 395                 400

Asp Glu Leu Thr Lys Asn Gln Val Ser Leu Thr Cys Leu Val Lys Gly
            405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
            435                 440                 445

Phe Ala Leu Val Ser Lys Leu Thr Val Asp Lys Ser Arg Trp Gln Gln
            450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
            485                 490

<210> SEQ ID NO 8
<211> LENGTH: 373
<212> TYPE: PRT
<213> ORGANISM: Artificial Sequence
<220> FEATURE:
<223> OTHER INFORMATION: Synthetic: RSLV-149 RNase chain (Fc-NLG-linker-
      RNase) amino acid sequence

<400> SEQUENCE: 8

Asp Lys Thr His Thr Cys Pro Pro Cys Pro Ala Pro Glu Leu Leu Gly
1               5                   10                  15

Gly Ser Ser Val Phe Leu Phe Pro Pro Lys Pro Lys Asp Thr Leu Met

```
                    20                  25                  30
Ile Ser Arg Thr Pro Glu Val Thr Cys Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
            115                 120                 125

Tyr Val Leu Pro Pro Ser Arg Asp Glu Leu Thr Lys Asn Gln Val Ser
            130                 135                 140

Leu Leu Cys Leu Val Lys Gly Phe Tyr Pro Ser Asp Ile Ala Val Glu
145                 150                 155                 160

Trp Glu Ser Asn Gly Gln Pro Glu Asn Asn Tyr Leu Thr Trp Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys Val Asp Gly Ala Ser Ser Pro Val Asn Val Ser Ser Pro
225                 230                 235                 240

Ser Val Gln Asp Ile Lys Glu Ser Arg Ala Lys Lys Phe Gln Arg Gln
                245                 250                 255

His Met Asp Ser Asp Ser Ser Pro Ser Ser Ser Ser Thr Tyr Cys Asn
            260                 265                 270

Gln Met Met Arg Arg Arg Asn Met Thr Gln Gly Arg Cys Lys Pro Val
            275                 280                 285

Asn Thr Phe Val His Glu Pro Leu Val Asp Val Gln Asn Val Cys Phe
290                 295                 300

Gln Glu Lys Val Thr Cys Lys Asn Gly Gln Gly Asn Cys Tyr Lys Ser
305                 310                 315                 320

Asn Ser Ser Met His Ile Thr Asp Cys Arg Leu Thr Asn Gly Ser Arg
                325                 330                 335

Tyr Pro Asn Cys Ala Tyr Arg Thr Ser Pro Lys Glu Arg His Ile Ile
            340                 345                 350

Val Ala Cys Glu Gly Ser Pro Tyr Val Pro Val His Phe Asp Ala Ser
            355                 360                 365

Val Glu Asp Ser Thr
    370

<210> SEQ ID NO 9
<211> LENGTH: 510
<212> TYPE: PRT
<213> ORGANISM: Artificial Sequence
<220> FEATURE:
<223> OTHER INFORMATION: Synthetic: RSLV-150 DNase chain (FcA-NLG
      linker-DNase) amino acid sequence

<400> SEQUENCE: 9
```

-continued

```
Glu Pro Lys Ser Cys Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
            115                 120                 125

Arg Glu Pro Gln Val Tyr Val Tyr Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Ala Leu Val
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys Val Asp Gly Ala Ser Ser Pro Val
225                 230                 235                 240

Asn Val Ser Ser Pro Ser Val Gln Asp Ile Leu Lys Ile Ala Ala Phe
                245                 250                 255

Asn Ile Gln Thr Phe Gly Arg Thr Lys Met Ser Asn Ala Thr Leu Val
            260                 265                 270

Ser Tyr Ile Val Gln Ile Leu Ser Arg Tyr Asp Ile Ala Leu Val Gln
            275                 280                 285

Glu Val Arg Asp Ser His Leu Thr Ala Val Gly Lys Leu Leu Asp Asn
            290                 295                 300

Leu Asn Gln Asp Ala Pro Asp Thr Tyr His Tyr Val Val Ser Glu Pro
305                 310                 315                 320

Leu Gly Arg Lys Ser Tyr Lys Glu Arg Tyr Leu Phe Val Tyr Arg Pro
                325                 330                 335

Asp Gln Val Ser Ala Val Asp Ser Tyr Tyr Tyr Asp Asp Gly Cys Glu
            340                 345                 350

Pro Cys Gly Asn Asp Thr Phe Asn Arg Glu Pro Phe Ile Val Arg Phe
            355                 360                 365

Phe Ser Arg Phe Thr Glu Val Arg Glu Phe Ala Ile Val Pro Leu His
            370                 375                 380

Ala Ala Pro Gly Asp Ala Val Ala Glu Ile Ala Leu Tyr Asp Val
385                 390                 395                 400

Tyr Leu Asp Val Gln Glu Lys Trp Gly Leu Glu Asp Val Met Leu Met
                405                 410                 415

Gly Asp Phe Asn Ala Gly Cys Ser Tyr Val Arg Pro Ser Gln Trp Ser
```

```
            420                 425                 430
Ser Ile Arg Leu Trp Thr Ser Pro Thr Phe Gln Trp Leu Ile Pro Asp
            435                 440                 445

Ser Ala Asp Thr Thr Ala Lys Pro Thr His Cys Ala Tyr Asp Arg Ile
        450                 455                 460

Val Val Ala Gly Met Leu Leu Arg Gly Ala Val Val Pro Asp Ser Ala
465                 470                 475                 480

Leu Pro Phe Asn Phe Gln Ala Ala Tyr Gly Leu Ser Asp Gln Leu Ala
                485                 490                 495

Gln Ala Ile Ser Asp His Tyr Pro Val Glu Val Met Leu Lys
                500                 505                 510

<210> SEQ ID NO 10
<211> LENGTH: 378
<212> TYPE: PRT
<213> ORGANISM: Artificial Sequence
<220> FEATURE:
<223> OTHER INFORMATION: Synthetic: RSLV-150 RNase chain (FcB-NLG
      linker-RNase) amino acid sequence

<400> SEQUENCE: 10

Glu Pro Lys Ser Cys Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Val Leu Pro Pro Ser Arg Asp Glu Leu Thr
130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys Val Asp Gly Ala Ser Ser Pro Val
225                 230                 235                 240

Asn Val Ser Ser Pro Ser Val Gln Asp Ile Lys Glu Ser Arg Ala Lys
                245                 250                 255

Lys Phe Gln Arg Gln His Met Asp Ser Asp Ser Ser Pro Ser Ser Ser
            260                 265                 270
```

```
Ser Thr Tyr Cys Asn Gln Met Met Arg Arg Asn Met Thr Gln Gly
            275                 280                 285

Arg Cys Lys Pro Val Asn Thr Phe Val His Glu Pro Leu Val Asp Val
    290                 295                 300

Gln Asn Val Cys Phe Gln Glu Lys Val Thr Cys Lys Asn Gly Gln Gly
305                 310                 315                 320

Asn Cys Tyr Lys Ser Asn Ser Ser Met His Ile Thr Asp Cys Arg Leu
                325                 330                 335

Thr Asn Gly Ser Arg Tyr Pro Asn Cys Ala Tyr Arg Thr Ser Pro Lys
            340                 345                 350

Glu Arg His Ile Ile Val Ala Cys Glu Gly Ser Pro Tyr Val Pro Val
            355                 360                 365

His Phe Asp Ala Ser Val Glu Asp Ser Thr
            370                 375

<210> SEQ ID NO 11
<211> LENGTH: 505
<212> TYPE: PRT
<213> ORGANISM: Artificial Sequence
<220> FEATURE:
<223> OTHER INFORMATION: Synthetic: RSLV-151 DNase chain (Fc-NLG
      linker-DNase) amino acid sequence

<400> SEQUENCE: 11

Asp Lys Thr His Thr Cys Pro Pro Cys Pro Ala Pro Glu Leu Leu Gly
1               5                   10                  15

Gly Ser Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Val Tyr Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Ala Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Val Asp Gly Ala Ser Ser Pro Val Asn Val Ser Ser Pro
225                 230                 235                 240

Ser Val Gln Asp Ile Leu Lys Ile Ala Ala Phe Asn Ile Gln Thr Phe
                245                 250                 255
```

```
Gly Arg Thr Lys Met Ser Asn Ala Thr Leu Val Ser Tyr Ile Val Gln
            260                 265                 270

Ile Leu Ser Arg Tyr Asp Ile Ala Leu Val Gln Glu Val Arg Asp Ser
            275                 280                 285

His Leu Thr Ala Val Gly Lys Leu Leu Asp Asn Leu Asn Gln Asp Ala
            290                 295                 300

Pro Asp Thr Tyr His Tyr Val Val Ser Glu Pro Leu Gly Arg Lys Ser
305                 310                 315                 320

Tyr Lys Glu Arg Tyr Leu Phe Val Tyr Arg Pro Asp Gln Val Ser Ala
                325                 330                 335

Val Asp Ser Tyr Tyr Tyr Asp Asp Gly Cys Glu Pro Cys Gly Asn Asp
            340                 345                 350

Thr Phe Asn Arg Glu Pro Phe Ile Val Arg Phe Phe Ser Arg Phe Thr
            355                 360                 365

Glu Val Arg Glu Phe Ala Ile Val Pro Leu His Ala Ala Pro Gly Asp
            370                 375                 380

Ala Val Ala Glu Ile Asp Ala Leu Tyr Asp Val Tyr Leu Asp Val Gln
385                 390                 395                 400

Glu Lys Trp Gly Leu Glu Asp Val Met Leu Met Gly Asp Phe Asn Ala
                405                 410                 415

Gly Cys Ser Tyr Val Arg Pro Ser Gln Trp Ser Ser Ile Arg Leu Trp
            420                 425                 430

Thr Ser Pro Thr Phe Gln Trp Leu Ile Pro Asp Ser Ala Asp Thr Thr
            435                 440                 445

Ala Lys Pro Thr His Cys Ala Tyr Asp Arg Ile Val Val Ala Gly Met
450                 455                 460

Leu Leu Arg Gly Ala Val Val Pro Asp Ser Ala Leu Pro Phe Asn Phe
465                 470                 475                 480

Gln Ala Ala Tyr Gly Leu Ser Asp Gln Leu Ala Gln Ala Ile Ser Asp
                485                 490                 495

His Tyr Pro Val Glu Val Met Leu Lys
                500                 505

<210> SEQ ID NO 12
<211> LENGTH: 373
<212> TYPE: PRT
<213> ORGANISM: Artificial Sequence
<220> FEATURE:
<223> OTHER INFORMATION: Synthetic: RSLV-151 RNase chain (Fc-NLG linker-
      RNase) amino acid sequence

<400> SEQUENCE: 12

Asp Lys Thr His Thr Cys Pro Pro Cys Pro Ala Pro Glu Leu Leu Gly
1               5                   10                  15

Gly Ser Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
```

```
                100             105             110
Glu Lys Thr Ile Ser Lys Ala Lys Gly Gln Pro Arg Glu Pro Gln Val
            115                 120             125

Tyr Val Leu Pro Pro Ser Arg Asp Glu Leu Thr Lys Asn Gln Val Ser
130             135                 140

Leu Leu Cys Leu Val Lys Gly Phe Tyr Pro Ser Asp Ile Ala Val Glu
145                 150                 155                 160

Trp Glu Ser Asn Gly Gln Pro Glu Asn Asn Tyr Leu Thr Trp Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
            210                 215                 220

Pro Gly Lys Val Asp Gly Ala Ser Ser Pro Val Asn Val Ser Ser Pro
225                 230                 235                 240

Ser Val Gln Asp Ile Lys Glu Ser Arg Ala Lys Lys Phe Gln Arg Gln
                245                 250                 255

His Met Asp Ser Asp Ser Ser Pro Ser Ser Ser Ser Thr Tyr Cys Asn
                260                 265                 270

Gln Met Met Arg Arg Arg Asn Met Thr Gln Gly Arg Cys Lys Pro Val
            275                 280                 285

Asn Thr Phe Val His Glu Pro Leu Val Asp Val Gln Asn Val Cys Phe
            290                 295                 300

Gln Glu Lys Val Thr Cys Lys Asn Gly Gln Gly Asn Cys Tyr Lys Ser
305                 310                 315                 320

Asn Ser Ser Met His Ile Thr Asp Cys Arg Leu Thr Asn Gly Ser Arg
                325                 330                 335

Tyr Pro Asn Cys Ala Tyr Arg Thr Ser Pro Lys Glu Arg His Ile Ile
                340                 345                 350

Val Ala Cys Glu Gly Ser Pro Tyr Val Pro Val His Phe Asp Ala Ser
                355                 360                 365

Val Glu Asp Ser Thr
                370

<210> SEQ ID NO 13
<211> LENGTH: 638
<212> TYPE: PRT
<213> ORGANISM: Artificial Sequence
<220> FEATURE:
<223> OTHER INFORMATION: Synthetic: RSLV-152 (RNase-Fc-NLG linker-DNase)
      amino acid sequence

<400> SEQUENCE: 13

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
                20                  25                  30

Arg Asn Met Thr Gln Gly Arg Cys Lys Pro Val Asn Thr Phe Val His
            35                  40                  45

Glu Pro Leu Val Asp Val Gln Asn Val Cys Phe Gln Glu Lys Val Thr
        50                  55                  60

Cys Lys Asn Gly Gln Gly Asn Cys Tyr Lys Ser Asn Ser Ser Met His
65                  70                  75                  80
```

```
Ile Thr Asp Cys Arg Leu Thr Asn Gly Ser Arg Tyr Pro Asn Cys Ala
             85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
            115                 120                 125

Glu Pro Lys Ser Ser Asp Lys Thr His Thr Cys Pro Pro Cys Pro Ala
130                 135                 140

Pro Glu Leu Leu Gly Gly Ser Ser Val Phe Leu Phe Pro Pro Lys Pro
145                 150                 155                 160

Lys Asp Thr Leu Met Ile Ser Arg Thr Pro Glu Val Thr Cys Val Val
            165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
            195                 200                 205

Tyr Asn Ser Thr Tyr Arg Val Val Ser Val Leu Thr Val Leu His Gln
            210                 215                 220

Asp Trp Leu Asn Gly Lys Glu Tyr Lys Cys Lys Val Ser Asn Lys Ala
225                 230                 235                 240

Leu Pro Ala Ser Ile Glu Lys Thr Ile Ser Lys Ala Lys Gly Gln Pro
            245                 250                 255

Arg Glu Pro Gln Val Tyr Val Tyr Pro Pro Ser Arg Asp Glu Leu Thr
            260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Ala Leu Val
305                 310                 315                 320

Ser Lys Leu Thr Val Asp Lys Ser Arg Trp Gln Gln Gly Asn Val Phe
            325                 330                 335

Ser Cys Ser Val Met His Glu Ala Leu His Asn His Tyr Thr Gln Lys
            340                 345                 350

Ser Leu Ser Leu Ser Pro Gly Lys Val Asp Gly Ala Ser Ser Pro Val
            355                 360                 365

Asn Val Ser Ser Pro Ser Val Gln Asp Ile Leu Lys Ile Ala Ala Phe
            370                 375                 380

Asn Ile Gln Thr Phe Gly Arg Thr Lys Met Ser Asn Ala Thr Leu Val
385                 390                 395                 400

Ser Tyr Ile Val Gln Ile Leu Ser Arg Tyr Asp Ile Ala Leu Val Gln
            405                 410                 415

Glu Val Arg Asp Ser His Leu Thr Ala Val Gly Lys Leu Leu Asp Asn
            420                 425                 430

Leu Asn Gln Asp Ala Pro Asp Thr Tyr His Tyr Val Val Ser Glu Pro
            435                 440                 445

Leu Gly Arg Lys Ser Tyr Lys Glu Arg Tyr Leu Phe Val Tyr Arg Pro
            450                 455                 460

Asp Gln Val Ser Ala Val Asp Ser Tyr Tyr Tyr Asp Asp Gly Cys Glu
465                 470                 475                 480

Pro Cys Gly Asn Asp Thr Phe Asn Arg Glu Pro Phe Ile Val Arg Phe
            485                 490                 495

Phe Ser Arg Phe Thr Glu Val Arg Glu Phe Ala Ile Val Pro Leu His
```

```
                500                 505                 510
Ala Ala Pro Gly Asp Ala Val Ala Glu Ile Asp Ala Leu Tyr Asp Val
            515                 520                 525

Tyr Leu Asp Val Gln Glu Lys Trp Gly Leu Glu Asp Val Met Leu Met
        530                 535                 540

Gly Asp Phe Asn Ala Gly Cys Ser Tyr Val Arg Pro Ser Gln Trp Ser
545                 550                 555                 560

Ser Ile Arg Leu Trp Thr Ser Pro Thr Phe Gln Trp Leu Ile Pro Asp
                565                 570                 575

Ser Ala Asp Thr Thr Ala Lys Pro Thr His Cys Ala Tyr Asp Arg Ile
            580                 585                 590

Val Val Ala Gly Met Leu Leu Arg Gly Ala Val Val Pro Asp Ser Ala
        595                 600                 605

Leu Pro Phe Asn Phe Gln Ala Ala Tyr Gly Leu Ser Asp Gln Leu Ala
                615                 620

Gln Ala Ile Ser Asp His Tyr Pro Val Glu Val Met Leu Lys
625                 630                 635

<210> SEQ ID NO 14
<211> LENGTH: 227
<212> TYPE: PRT
<213> ORGANISM: Artificial Sequence
<220> FEATURE:
<223> OTHER INFORMATION: Synthetic: RSLV-152 Fc domain chain amino acid
      sequence

<400> SEQUENCE: 14

Asp Lys Thr His Thr Cys Pro Pro Cys Pro Ala Pro Glu Leu Leu Gly
1               5                   10                  15

Gly Ser Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Val Leu Pro Pro Ser Arg Asp Glu Leu Thr Lys Asn Gln Val Ser
    130                 135                 140

Leu Leu Cys Leu Val Lys Gly Phe Tyr Pro Ser Asp Ile Ala Val Glu
145                 150                 155                 160

Trp Glu Ser Asn Gly Gln Pro Glu Asn Asn Tyr Leu Thr Trp Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

Pro Gly Lys
225

<210> SEQ ID NO 15
<211> LENGTH: 505
<212> TYPE: PRT
<213> ORGANISM: Artificial Sequence
<220> FEATURE:
<223> OTHER INFORMATION: Synthetic: RSLV-153 DNase chain (Fc-NLG linker-
      DNase) amino acid sequence

<400> SEQUENCE: 15

```
Asp Lys Thr His Thr Cys Pro Pro Cys Pro Ala Pro Glu Leu Leu Gly
1               5                   10                  15

Gly Ser Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Val Tyr Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Ala Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Val Asp Gly Ala Ser Ser Pro Val Asn Val Ser Ser Pro
225                 230                 235                 240

Ser Val Gln Asp Ile Leu Lys Ile Ala Ala Phe Asn Ile Gln Thr Phe
                245                 250                 255

Gly Arg Thr Lys Met Ser Asn Ala Thr Leu Val Ser Tyr Ile Val Gln
            260                 265                 270

Ile Leu Ser Arg Tyr Asp Ile Ala Leu Val Gln Glu Val Arg Asp Ser
        275                 280                 285

His Leu Thr Ala Val Gly Lys Leu Leu Asp Asn Leu Asn Gln Asp Ala
    290                 295                 300

Pro Asp Thr Tyr His Tyr Val Val Ser Glu Pro Leu Gly Arg Lys Ser
305                 310                 315                 320

Tyr Lys Glu Arg Tyr Leu Phe Val Tyr Arg Pro Asp Gln Val Ser Ala
                325                 330                 335

Val Asp Ser Tyr Tyr Tyr Asp Asp Gly Cys Glu Pro Cys Gly Asn Asp
            340                 345                 350
```

```
Thr Phe Asn Arg Glu Pro Phe Ile Val Arg Phe Phe Ser Arg Phe Thr
            355                 360                 365

Glu Val Arg Glu Phe Ala Ile Val Pro Leu His Ala Ala Pro Gly Asp
370                 375                 380

Ala Val Ala Glu Ile Asp Ala Leu Tyr Asp Val Tyr Leu Asp Val Gln
385                 390                 395                 400

Glu Lys Trp Gly Leu Glu Asp Val Met Leu Met Gly Asp Phe Asn Ala
            405                 410                 415

Gly Cys Ser Tyr Val Arg Pro Ser Gln Trp Ser Ser Ile Arg Leu Trp
            420                 425                 430

Thr Ser Pro Thr Phe Gln Trp Leu Ile Pro Asp Ser Ala Asp Thr Thr
            435                 440                 445

Ala Lys Pro Thr His Cys Ala Tyr Asp Arg Ile Val Val Ala Gly Met
            450                 455                 460

Leu Leu Arg Gly Ala Val Val Pro Asp Ser Ala Leu Pro Phe Asn Phe
465                 470                 475                 480

Gln Ala Ala Tyr Gly Leu Ser Asp Gln Leu Ala Gln Ala Ile Ser Asp
            485                 490                 495

His Tyr Pro Val Glu Val Met Leu Lys
            500                 505

<210> SEQ ID NO 16
<211> LENGTH: 360
<212> TYPE: PRT
<213> ORGANISM: Artificial Sequence
<220> FEATURE:
<223> OTHER INFORMATION: Synthetic: RSLV-153 RNase chain (RNase-Fc)
      amino acid sequence

<400> SEQUENCE: 16

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
            35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125

Glu Pro Lys Ser Ser Asp Lys Thr His Thr Cys Pro Pro Cys Pro Ala
    130                 135                 140

Pro Glu Leu Leu Gly Gly Ser Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
```

```
                195                 200                 205
Tyr Asn Ser Thr Tyr Arg Val Val Ser Val Leu Thr Val Leu His Gln
            210                 215                 220
Asp Trp Leu Asn Gly Lys Glu Tyr Lys Cys Lys Val Ser Asn Lys Ala
225                 230                 235                 240
Leu Pro Ala Ser Ile Glu Lys Thr Ile Ser Lys Ala Lys Gly Gln Pro
                245                 250                 255
Arg Glu Pro Gln Val Tyr Val Leu Pro Pro Ser Arg Asp Glu Leu Thr
            260                 265                 270
Lys Asn Gln Val Ser Leu Leu Cys Leu Val Lys Gly Phe Tyr Pro Ser
275                 280                 285
Asp Ile Ala Val Glu Trp Glu Ser Asn Gly Gln Pro Glu Asn Asn Tyr
                290                 295                 300
Leu Thr Trp Pro Pro Val Leu Asp Ser Asp Gly Ser Phe Phe Leu Tyr
305                 310                 315                 320
Ser Lys Leu Thr Val Asp Lys Ser Arg Trp Gln Gln Gly Asn Val Phe
                325                 330                 335
Ser Cys Ser Val Met His Glu Ala Leu His Asn His Tyr Thr Gln Lys
            340                 345                 350
Ser Leu Ser Leu Ser Pro Gly Lys
            355                 360

<210> SEQ ID NO 17
<211> LENGTH: 621
<212> TYPE: PRT
<213> ORGANISM: Artificial Sequence
<220> FEATURE:
<223> OTHER INFORMATION: Synthetic: RSLV-154 (RNase-Fc-NLG linker-DNase)
      amino acid sequence

<400> SEQUENCE: 17

Lys Glu Ser Arg Ala Lys Lys Phe Gln Arg Gln His Met Asp Ser Asp
1               5                   10                  15
Ser Ser Pro Ser Ser Ser Ser Thr Tyr Cys Asn Gln Met Met Arg Arg
                20                  25                  30
Arg Asn Met Thr Gln Gly Arg Cys Lys Pro Val Asn Thr Phe Val His
            35                  40                  45
Glu Pro Leu Val Asp Val Gln Asn Val Cys Phe Gln Glu Lys Val Thr
50                  55                  60
Cys Lys Asn Gly Gln Gly Asn Cys Tyr Lys Ser Asn Ser Ser Met His
65                  70                  75                  80
Ile Thr Asp Cys Arg Leu Thr Asn Gly Ser Arg Tyr Pro Asn Cys Ala
                85                  90                  95
Tyr Arg Thr Ser Pro Lys Glu Arg His Ile Ile Val Ala Cys Glu Gly
            100                 105                 110
Ser Pro Tyr Val Pro Val His Phe Asp Ala Ser Val Glu Asp Ser Thr
        115                 120                 125
Glu Leu Leu Gly Gly Ser Ser Val Phe Leu Phe Pro Pro Lys Pro Lys
    130                 135                 140
Asp Thr Leu Met Ile Ser Arg Thr Pro Glu Val Thr Cys Val Val Val
145                 150                 155                 160
Asp Val Ser His Glu Asp Pro Glu Val Lys Phe Asn Trp Tyr Val Asp
                165                 170                 175
Gly Val Glu Val His Asn Ala Lys Thr Lys Pro Arg Glu Glu Gln Tyr
            180                 185                 190
```

```
Asn Ser Thr Tyr Arg Val Ser Val Leu Thr Val His Gln Asp
        195                 200                 205

Trp Leu Asn Gly Lys Glu Tyr Lys Cys Lys Val Ser Asn Lys Ala Leu
210                 215                 220

Pro Ala Ser Ile Glu Lys Thr Ile Ser Lys Ala Lys Gly Gln Pro Arg
225                 230                 235                 240

Glu Pro Gln Val Tyr Thr Leu Pro Pro Ser Arg Asp Glu Leu Thr Lys
                245                 250                 255

Asn Gln Val Asn Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Asn Ser
    290                 295                 300

Thr Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys Val Asp Gly Ala Ser Ser Pro Val Asn
            340                 345                 350

Val Ser Ser Pro Ser Val Gln Asp Ile Leu Lys Ile Ala Ala Phe Asn
        355                 360                 365

Ile Gln Thr Phe Gly Arg Thr Lys Met Ser Asn Ala Thr Leu Val Ser
    370                 375                 380

Tyr Ile Val Gln Ile Leu Ser Arg Tyr Asp Ile Ala Leu Val Gln Glu
385                 390                 395                 400

Val Arg Asp Ser His Leu Thr Ala Val Gly Lys Leu Leu Asp Asn Leu
                405                 410                 415

Asn Gln Asp Ala Pro Asp Thr Tyr His Tyr Val Val Ser Glu Pro Leu
            420                 425                 430

Gly Arg Lys Ser Tyr Lys Glu Arg Tyr Leu Phe Val Tyr Arg Pro Asp
        435                 440                 445

Gln Val Ser Ala Val Asp Ser Tyr Tyr Tyr Asp Asp Gly Cys Glu Pro
    450                 455                 460

Cys Gly Asn Asp Thr Phe Asn Arg Glu Pro Phe Ile Val Arg Phe Phe
465                 470                 475                 480

Ser Arg Phe Thr Glu Val Arg Glu Phe Ala Ile Val Pro Leu His Ala
                485                 490                 495

Ala Pro Gly Asp Ala Val Ala Glu Ile Asp Ala Leu Tyr Asp Val Tyr
            500                 505                 510

Leu Asp Val Gln Glu Lys Trp Gly Leu Glu Asp Val Met Leu Met Gly
        515                 520                 525

Asp Phe Asn Ala Gly Cys Ser Tyr Val Arg Pro Ser Gln Trp Ser Ser
    530                 535                 540

Ile Arg Leu Trp Thr Ser Pro Thr Phe Gln Trp Leu Ile Pro Asp Ser
545                 550                 555                 560

Ala Asp Thr Thr Ala Lys Pro Thr His Cys Ala Tyr Asp Arg Ile Val
                565                 570                 575

Val Ala Gly Met Leu Leu Arg Gly Ala Val Val Pro Asp Ser Ala Leu
            580                 585                 590

Pro Phe Asn Phe Gln Ala Ala Tyr Gly Leu Ser Asp Gln Leu Ala Gln
        595                 600                 605

Ala Ile Ser Asp His Tyr Pro Val Glu Val Met Leu Lys
```

<210> SEQ ID NO 18
<211> LENGTH: 505
<212> TYPE: PRT
<213> ORGANISM: Artificial Sequence
<220> FEATURE:
<223> OTHER INFORMATION: Synthetic: Fc-NLG-linker-DNAse (control construct)

<400> SEQUENCE: 18

Asp Lys Thr His Thr Cys Pro Pro Cys Pro Ala Pro Glu Leu Leu Gly
1               5                   10                  15

Gly Ser Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Val Asp Gly Ala Ser Ser Pro Val Asn Val Ser Ser Pro
225                 230                 235                 240

Ser Val Gln Asp Ile Leu Lys Ile Ala Ala Phe Asn Ile Gln Thr Phe
                245                 250                 255

Gly Glu Thr Lys Met Ser Asn Ala Thr Leu Val Ser Tyr Ile Val Gln
            260                 265                 270

Ile Leu Ser Arg Tyr Asp Ile Ala Leu Val Gln Glu Val Arg Asp Ser
        275                 280                 285

His Leu Thr Ala Val Gly Lys Leu Leu Asp Asn Leu Asn Gln Asp Ala
    290                 295                 300

Pro Asp Thr Tyr His Tyr Val Val Ser Glu Pro Leu Gly Arg Asn Ser
305                 310                 315                 320

Tyr Lys Glu Arg Tyr Leu Phe Val Tyr Arg Pro Asp Gln Val Ser Ala
                325                 330                 335

Val Asp Ser Tyr Tyr Tyr Asp Asp Gly Cys Glu Pro Cys Arg Asn Asp
            340                 345                 350

```
Thr Phe Asn Arg Glu Pro Phe Ile Val Arg Phe Ser Arg Phe Thr
            355                 360                 365
Glu Val Arg Glu Phe Ala Ile Val Pro Leu His Ala Ala Pro Gly Asp
        370                 375                 380
Ala Val Ala Glu Ile Asp Ala Leu Tyr Asp Val Tyr Leu Asp Val Gln
385                 390                 395                 400
Glu Lys Trp Gly Leu Glu Asp Val Met Leu Met Gly Asp Phe Asn Ala
                405                 410                 415
Gly Cys Ser Tyr Val Arg Pro Ser Gln Trp Ser Ser Ile Arg Leu Trp
            420                 425                 430
Thr Ser Pro Thr Phe Gln Trp Leu Ile Pro Asp Ser Ala Asp Thr Thr
            435                 440                 445
Ala Thr Pro Thr His Cys Ala Tyr Asp Arg Ile Val Val Ala Gly Met
            450                 455                 460
Leu Leu Arg Gly Ala Val Val Pro Asp Ser Ala Leu Pro Phe Asn Phe
465                 470                 475                 480
Gln Ala Ala Tyr Gly Leu Ser Asp Gln Leu Ala Gln Ala Ile Ser Asp
                485                 490                 495
His Tyr Pro Val Glu Val Met Leu Lys
                500                 505

<210> SEQ ID NO 19
<211> LENGTH: 492
<212> TYPE: PRT
<213> ORGANISM: Artificial Sequence
<220> FEATURE:
<223> OTHER INFORMATION: Synthetic: DNASe-Fc (control construct)

<400> SEQUENCE: 19

Leu Lys Ile Ala Ala Phe Asn Ile Gln Thr Phe Gly Arg Thr Lys Met
1               5                   10                  15
Ser Asn Ala Thr Leu Val Ser Tyr Ile Val Gln Ile Leu Ser Arg Tyr
            20                  25                  30
Asp Ile Ala Leu Val Gln Glu Val Arg Asp Ser His Leu Thr Ala Val
        35                  40                  45
Gly Lys Leu Leu Asp Asn Leu Asn Gln Asp Ala Pro Asp Thr Tyr His
    50                  55                  60
Tyr Val Val Ser Glu Pro Leu Gly Arg Lys Ser Tyr Lys Glu Arg Tyr
65                  70                  75                  80
Leu Phe Val Tyr Arg Pro Asp Gln Val Ser Ala Val Asp Ser Tyr Tyr
                85                  90                  95
Tyr Asp Asp Gly Cys Glu Pro Cys Gly Asn Asp Thr Phe Asn Arg Glu
            100                 105                 110
Pro Phe Ile Val Arg Phe Phe Ser Arg Phe Thr Glu Val Arg Glu Phe
        115                 120                 125
Ala Ile Val Pro Leu His Ala Ala Pro Gly Asp Ala Val Ala Glu Ile
    130                 135                 140
Asp Ala Leu Tyr Asp Val Tyr Leu Asp Val Gln Glu Lys Trp Gly Leu
145                 150                 155                 160
Glu Asp Val Met Leu Met Gly Asp Phe Asn Ala Gly Cys Ser Tyr Val
                165                 170                 175
Arg Pro Ser Gln Trp Ser Ser Ile Arg Leu Trp Thr Ser Pro Thr Phe
            180                 185                 190
Gln Trp Leu Ile Pro Asp Ser Ala Asp Thr Thr Ala Lys Pro Thr His
        195                 200                 205
```

```
Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys Glu Pro Lys Ser Ser Asp Lys Thr His Thr Cys Pro
            260                 265                 270

Pro Cys Pro Ala Pro Glu Leu Leu Gly Gly Ser Ser Val Phe Leu Phe
        275                 280                 285

Pro Pro Lys Pro Lys Asp Thr Leu Met Ile Ser Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Ser Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490

<210> SEQ ID NO 20
<211> LENGTH: 260
<212> TYPE: PRT
<213> ORGANISM: Homo sapiens
<220> FEATURE:
<221> NAME/KEY: misc_feature
<222> LOCATION: (1)..(260)
<223> OTHER INFORMATION: Mature wild type Human DNase1

<400> SEQUENCE: 20

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
```

```
                65                  70                  75                  80
Leu Phe Val Tyr Arg Pro Asp Gln Val Ser Ala Val Asp Ser Tyr Tyr
                    85                  90                  95

Tyr Asp Asp Gly Cys Glu Pro Cys Gly Asn Asp Thr Phe Asn Arg Glu
                    100                 105                 110

Pro Ala Ile Val Arg Phe Phe Ser Arg Phe Thr Glu Val Arg Glu Phe
                    115                 120                 125

Ala Ile Val Pro Leu His Ala Ala Pro Gly Asp Ala Val Ala Glu Ile
                    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                    165                 170                 175

Arg Pro Ser Gln Trp Ser Ser Ile Arg Leu Trp Thr Ser Pro Thr Phe
                    180                 185                 190

Gln Trp Leu Ile Pro Asp Ser Ala Asp Thr Thr Ala Thr Pro Thr His
                    195                 200                 205

Cys Ala Tyr Asp Arg Ile Val Val Ala Gly Met Leu Leu Arg Gly Ala
                    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                    245                 250                 255

Val Met Leu Lys
                260

<210> SEQ ID NO 21
<211> LENGTH: 260
<212> TYPE: PRT
<213> ORGANISM: Homo sapiens
<220> FEATURE:
<221> NAME/KEY: misc_feature
<222> LOCATION: (1)..(260)
<223> OTHER INFORMATION: Mature human DNase1 A114F

<400> SEQUENCE: 21

Leu Lys Ile Ala Ala Phe Asn Ile Gln Thr Phe Gly Glu Thr Lys Met
1                   5                   10                  15

Ser Asn Ala Thr Leu Val Ser Tyr Ile Val Gln Ile Leu Ser Arg Tyr
                    20                  25                  30

Asp Ile Ala Leu Val Gln Glu Val Arg Asp Ser His Leu Thr Ala Val
                    35                  40                  45

Gly Lys Leu Leu Asp Asn Leu Asn Gln Asp Ala Pro Asp Thr Tyr His
                    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                    85                  90                  95

Tyr Asp Asp Gly Cys Glu Pro Cys Gly Asn Asp Thr Phe Asn Arg Glu
                    100                 105                 110

Pro Phe Ile Val Arg Phe Phe Ser Arg Phe Thr Glu Val Arg Glu Phe
                    115                 120                 125

Ala Ile Val Pro Leu His Ala Ala Pro Gly Asp Ala Val Ala Glu Ile
                    130                 135                 140

Asp Ala Leu Tyr Asp Val Tyr Leu Asp Val Gln Glu Lys Trp Gly Leu
145                 150                 155                 160
```

```
Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
                180                 185                 190

Gln Trp Leu Ile Pro Asp Ser Ala Asp Thr Thr Ala Thr Pro Thr His
                195                 200                 205

Cys Ala Tyr Asp Arg Ile Val Val Ala Gly Met Leu Leu Arg Gly Ala
                210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 22
<211> LENGTH: 260
<212> TYPE: PRT
<213> ORGANISM: Homo sapiens
<220> FEATURE:
<221> NAME/KEY: misc_feature
<222> LOCATION: (1)..(260)
<223> OTHER INFORMATION: Mature human DNase1 G105R

<400> SEQUENCE: 22

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
                20                  25                  30

Asp Ile Ala Leu Val Gln Glu Val Arg Asp Ser His Leu Thr Ala Val
                35                  40                  45

Gly Lys Leu Leu Asp Asn Leu Asn Gln Asp Ala Pro Asp Thr Tyr His
            50                  55                  60

Tyr Val Val Ser Glu Pro Leu Gly Arg Asn Ser Tyr Lys Glu Arg Tyr
65              70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Arg Asn Asp Thr Phe Asn Arg Glu
                100                 105                 110

Pro Ala Ile Val Arg Phe Phe Ser Arg Phe Thr Glu Val Arg Glu Phe
                115                 120                 125

Ala Ile Val Pro Leu His Ala Ala Pro Gly Asp Ala Val Ala Glu Ile
                130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
                180                 185                 190

Gln Trp Leu Ile Pro Asp Ser Ala Asp Thr Thr Ala Thr Pro Thr His
                195                 200                 205

Cys Ala Tyr Asp Arg Ile Val Val Ala Gly Met Leu Leu Arg Gly Ala
                210                 215                 220

Val Val Pro Asp Ser Ala Leu Pro Phe Asn Phe Gln Ala Ala Tyr Gly
225                 230                 235                 240
```

-continued

Leu Ser Asp Gln Leu Ala Gln Ala Ile Ser Asp His Tyr Pro Val Glu
            245                 250                 255

Val Met Leu Lys
            260

<210> SEQ ID NO 23
<211> LENGTH: 282
<212> TYPE: PRT
<213> ORGANISM: Homo sapiens
<220> FEATURE:
<221> NAME/KEY: misc_feature
<222> LOCATION: (1)..(282)
<223> OTHER INFORMATION: Precursor human DNase1

<400> SEQUENCE: 23

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
        275                 280

<210> SEQ ID NO 24
<211> LENGTH: 260
<212> TYPE: PRT
<213> ORGANISM: Homo sapiens
<220> FEATURE:
<221> NAME/KEY: misc_feature

```
<222> LOCATION: (1)..(260)
<223> OTHER INFORMATION: Mature human DNase1 N18S/N106S/A114F

<400> SEQUENCE: 24

Leu Lys Ile Ala Ala Phe Asn Ile Gln Thr Phe Gly Glu Thr Lys Met
1               5                   10                  15

Ser Ser Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Ser Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 25
<211> LENGTH: 260
<212> TYPE: PRT
<213> ORGANISM: Homo sapiens
<220> FEATURE:
<221> NAME/KEY: misc_feature
<222> LOCATION: (1)..(260)
<223> OTHER INFORMATION: Mature human DNase1 E13R/N74K/A114F/ T205K

<400> SEQUENCE: 25

Leu Lys Ile Ala Ala Phe Asn Ile Gln Thr Phe Gly Arg Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60
```

```
Tyr Val Val Ser Glu Pro Leu Gly Arg Lys Ser Tyr Lys Glu Arg Tyr
 65                  70                  75                  80

Leu Phe Val Tyr Arg Pro Asp Gln Val Ser Ala Val Asp Ser Tyr Tyr
                 85                  90                  95

Tyr Asp Asp Gly Cys Glu Pro Cys Gly Asn Asp Thr Phe Asn Arg Glu
                100                 105                 110

Pro Phe Ile Val Arg Phe Phe Ser Arg Phe Thr Glu Val Arg Glu Phe
                115                 120                 125

Ala Ile Val Pro Leu His Ala Ala Pro Gly Asp Ala Val Ala Glu Ile
                130                 135             140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
                180                 185                 190

Gln Trp Leu Ile Pro Asp Ser Ala Asp Thr Thr Ala Lys Pro Thr His
                195                 200                 205

Cys Ala Tyr Asp Arg Ile Val Val Ala Gly Met Leu Leu Arg Gly Ala
210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 26
<211> LENGTH: 260
<212> TYPE: PRT
<213> ORGANISM: Homo sapiens
<220> FEATURE:
<221> NAME/KEY: misc_feature
<222> LOCATION: (1)..(260)
<223> OTHER INFORMATION: Mature human DNase1 E13R/N74K/A114F/
      T205K/N18S/N106S

<400> SEQUENCE: 26

Leu Lys Ile Ala Ala Phe Asn Ile Gln Thr Phe Gly Arg Thr Lys Met
1               5                   10                  15

Ser Ser Ala Thr Leu Val Ser Tyr Ile Val Gln Ile Leu Ser Arg Tyr
                20                  25                  30

Asp Ile Ala Leu Val Gln Glu Val Arg Asp Ser His Leu Thr Ala Val
                35                  40                  45

Gly Lys Leu Leu Asp Asn Leu Asn Gln Asp Ala Pro Asp Thr Tyr His
            50                  55                  60

Tyr Val Val Ser Glu Pro Leu Gly Arg Lys Ser Tyr Lys Glu Arg Tyr
 65                  70                  75                  80

Leu Phe Val Tyr Arg Pro Asp Gln Val Ser Ala Val Asp Ser Tyr Tyr
                 85                  90                  95

Tyr Asp Asp Gly Cys Glu Pro Cys Gly Ser Asp Thr Phe Asn Arg Glu
                100                 105                 110

Pro Phe Ile Val Arg Phe Phe Ser Arg Phe Thr Glu Val Arg Glu Phe
                115                 120                 125

Ala Ile Val Pro Leu His Ala Ala Pro Gly Asp Ala Val Ala Glu Ile
                130                 135             140
```

```
Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Lys Pro Thr His
            195                 200                 205

Cys Ala Tyr Asp Arg Ile Val Val Ala Gly Met Leu Leu Arg Gly Ala
210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 27
<211> LENGTH: 128
<212> TYPE: PRT
<213> ORGANISM: Homo sapiens
<220> FEATURE:
<221> NAME/KEY: misc_feature
<222> LOCATION: (1)..(128)
<223> OTHER INFORMATION: Mature human RNase1

<400> SEQUENCE: 27

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30

Arg Asn Met Thr Gln Gly Arg Cys Lys Pro Val Asn Thr Phe Val His
            35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125

<210> SEQ ID NO 28
<211> LENGTH: 128
<212> TYPE: PRT
<213> ORGANISM: Homo sapiens
<220> FEATURE:
<221> NAME/KEY: misc_feature
<222> LOCATION: (1)..(128)
<223> OTHER INFORMATION: Mature human RNase1 N34S/N76S/N88S

<400> SEQUENCE: 28

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30
```

```
Arg Ser Met Thr Gln Gly Arg Cys Lys Pro Val Asn Thr Phe Val His
        35                  40                  45

Glu Pro Leu Val Asp Val Gln Asn Val Cys Phe Gln Glu Lys Val Thr
 50                  55                  60

Cys Lys Asn Gly Gln Gly Asn Cys Tyr Lys Ser Ser Ser Ser Met His
 65                  70                  75                  80

Ile Thr Asp Cys Arg Leu Thr Ser Gly Ser Arg Tyr Pro Asn Cys Ala
                85                  90                  95

Tyr Arg Thr Ser Pro Lys Glu Arg His Ile Ile Val Ala Cys Glu Gly
                    100                 105                 110

Ser Pro Tyr Val Pro Val His Phe Asp Ala Ser Val Glu Asp Ser Thr
            115                 120                 125
```

<210> SEQ ID NO 29
<211> LENGTH: 156
<212> TYPE: PRT
<213> ORGANISM: Homo sapiens
<220> FEATURE:
<221> NAME/KEY: misc_feature
<222> LOCATION: (1)..(156)
<223> OTHER INFORMATION: Precursor human RNase1

<400> SEQUENCE: 29

```
Met Ala Leu Glu Lys Ser Leu Val Arg Leu Leu Leu Leu Val Leu Ile
 1               5                  10                  15

Leu Leu Val Leu Gly Trp Val Gln Pro Ser Leu Gly Lys Glu Ser Arg
                20                  25                  30

Ala Lys Lys Phe Gln Arg Gln His Met Asp Ser Asp Ser Ser Pro Ser
            35                  40                  45

Ser Ser Ser Thr Tyr Cys Asn Gln Met Met Arg Arg Arg Asn Met Thr
 50                  55                  60

Gln Gly Arg Cys Lys Pro Val Asn Thr Phe Val His Glu Pro Leu Val
 65                  70                  75                  80

Asp Val Gln Asn Val Cys Phe Gln Glu Lys Val Thr Cys Lys Asn Gly
                85                  90                  95

Gln Gly Asn Cys Tyr Lys Ser Asn Ser Ser Met His Ile Thr Asp Cys
            100                 105                 110

Arg Leu Thr Asn Gly Ser Arg Tyr Pro Asn Cys Ala Tyr Arg Thr Ser
        115                 120                 125

Pro Lys Glu Arg His Ile Ile Val Ala Cys Glu Gly Ser Pro Tyr Val
    130                 135                 140

Pro Val His Phe Asp Ala Ser Val Glu Asp Ser Thr
145                 150                 155
```

<210> SEQ ID NO 30
<211> LENGTH: 15
<212> TYPE: PRT
<213> ORGANISM: Artificial Sequence
<220> FEATURE:
<223> OTHER INFORMATION: Synthetic: (Gly4Ser)3 linker

<400> SEQUENCE: 30

```
Gly Gly Gly Gly Ser Gly Gly Gly Gly Ser Gly Gly Gly Gly Ser
 1               5                  10                  15
```

<210> SEQ ID NO 31
<211> LENGTH: 17
<212> TYPE: PRT
<213> ORGANISM: Artificial Sequence
<220> FEATURE:

<223> OTHER INFORMATION: Synthetic: Gaussia luciferase signal peptide

<400> SEQUENCE: 31

Met Gly Val Lys Val Leu Phe Ala Leu Ile Cys Ile Ala Val Ala Glu
1               5                   10                  15

Ala

<210> SEQ ID NO 32
<211> LENGTH: 47
<212> TYPE: PRT
<213> ORGANISM: Artificial Sequence
<220> FEATURE:
<223> OTHER INFORMATION: Synthetic: Linker

<400> SEQUENCE: 32

Leu Glu Ala Glu Ala Ala Ala Lys Glu Ala Ala Ala Lys Glu Ala Ala
1               5                   10                  15

Ala Lys Glu Ala Ala Lys Ala Leu Glu Ala Glu Ala Ala Ala Lys
            20                  25                  30

Glu Ala Ala Ala Lys Glu Ala Ala Ala Lys Glu Ala Ala Ala Lys
        35                  40                  45

<210> SEQ ID NO 33
<211> LENGTH: 7
<212> TYPE: PRT
<213> ORGANISM: Artificial Sequence
<220> FEATURE:
<223> OTHER INFORMATION: Synthetic: O-linked glycosylation consensus
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is Thr or Ser

<400> SEQUENCE: 33

Cys Xaa Xaa Gly Gly Xaa Cys
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic: O-linked glycosylation consensus
<220> FEATURE:
<221> NAME/KEY: misc_feature
<222> LOCATION: (4)..(4)
<223> OTHER INFORMATION: Xaa is Glu or Asp

<400> SEQUENCE: 34

Asn Ser Thr Xaa Ala
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic: O-linked glycosylation consensus

<400> SEQUENCE: 35

Asn Ile Thr Gln Ser
1               5

```
<210> SEQ ID NO 36
<211> LENGTH: 5
<212> TYPE: PRT
<213> ORGANISM: Artificial Sequence
<220> FEATURE:
<223> OTHER INFORMATION: Synthetic: O-linked glycosylation consensus

<400> SEQUENCE: 36

Gln Ser Thr Gln Ser
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic: O-linked glycosylation consensus
<220> FEATURE:
<221> NAME/KEY: misc_feature
<222> LOCATION: (1)..(1)
<223> OTHER INFORMATION: Xaa is Asp or Glu
<220> FEATURE:
<221> NAME/KEY: misc_feature
<222> LOCATION: (4)..(4)
<223> OTHER INFORMATION: Xaa is Arg or Lys

<400> SEQUENCE: 37

Xaa Phe Thr Xaa Val
1               5

<210> SEQ ID NO 38
<211> LENGTH: 4
<212> TYPE: PRT
<213> ORGANISM: Artificial Sequence
<220> FEATURE:
<223> OTHER INFORMATION: Synthetic: O-linked glycosylation consensus
<220> FEATURE:
<221> NAME/KEY: misc_feature
<222> LOCATION: (2)..(2)
<223> OTHER INFORMATION: Xaa is Glu or Asp

<400> SEQUENCE: 38

Cys Xaa Ser Asn
1

<210> SEQ ID NO 39
<211> LENGTH: 5
<212> TYPE: PRT
<213> ORGANISM: Artificial Sequence
<220> FEATURE:
<223> OTHER INFORMATION: Synthetic: O-linked glycosylation consensus
<220> FEATURE:
<221> NAME/KEY: misc_feature
<222> LOCATION: (5)..(5)
<223> OTHER INFORMATION: Xaa is Lys or Arg

<400> SEQUENCE: 39

Gly Gly Ser Cys Xaa
1               5

<210> SEQ ID NO 40
<211> LENGTH: 20
<212> TYPE: PRT
<213> ORGANISM: Artificial Sequence
<220> FEATURE:
<223> OTHER INFORMATION: Synthetic: VK3 light chain signal peptide

<400> SEQUENCE: 40

Met Glu Thr Pro Ala Gln Leu Leu Phe Leu Leu Leu Leu Trp Leu Pro
```

```
1               5                   10                  15
Asp Thr Thr Gly
            20

<210> SEQ ID NO 41
<211> LENGTH: 18
<212> TYPE: PRT
<213> ORGANISM: Artificial Sequence
<220> FEATURE:
<223> OTHER INFORMATION: Synthetic: NLG linker

<400> SEQUENCE: 41

Val Asp Gly Ala Ser Ser Pro Val Asn Val Ser Ser Pro Ser Val Gln
1               5                   10                  15

Asp Ile

<210> SEQ ID NO 42
<211> LENGTH: 50
<212> TYPE: PRT
<213> ORGANISM: Artificial Sequence
<220> FEATURE:
<223> OTHER INFORMATION: Synthetic: linker

<400> SEQUENCE: 42

Leu Glu Ala Glu Ala Ala Ala Lys Glu Ala Ala Ala Lys Glu Ala Ala
1               5                   10                  15

Ala Lys Glu Ala Ala Lys Ala Leu Glu Ala Glu Ala Ala Ala Lys
            20                  25                  30

Glu Ala Ala Ala Lys Glu Ala Ala Lys Glu Ala Ala Ala Lys Ala
        35                  40                      45

Leu Glu
    50

<210> SEQ ID NO 43
<211> LENGTH: 4
<212> TYPE: PRT
<213> ORGANISM: Artificial Sequence
<220> FEATURE:
<223> OTHER INFORMATION: Synthetic: Linker

<400> SEQUENCE: 43

Gly Gly Ser Gly
1

<210> SEQ ID NO 44
<211> LENGTH: 4
<212> TYPE: PRT
<213> ORGANISM: Artificial Sequence
<220> FEATURE:
<223> OTHER INFORMATION: Synthetic: Linker

<400> SEQUENCE: 44

Gly Ser Ala Thr
1

<210> SEQ ID NO 45
<211> LENGTH: 232
<212> TYPE: PRT
<213> ORGANISM: Homo sapiens
<220> FEATURE:
<221> NAME/KEY: misc_feature
<222> LOCATION: (1)..(232)
<223> OTHER INFORMATION: Human wild-type IgG1 Fc domain

<400> SEQUENCE: 45
```

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 46
<211> LENGTH: 285
<212> TYPE: PRT
<213> ORGANISM: Homo sapiens
<220> FEATURE:
<221> NAME/KEY: misc_feature
<222> LOCATION: (1)..(285)
<223> OTHER INFORMATION: Mature human DNase1L3

<400> SEQUENCE: 46

Met Arg Ile Cys Ser Phe Asn Val Arg Ser Phe Gly Glu Ser Lys Gln
1               5                   10                  15

Glu Asp Lys Asn Ala Met Asp Val Ile Val Lys Val Ile Lys Arg Cys
            20                  25                  30

Asp Ile Ile Leu Val Met Glu Ile Lys Asp Ser Asn Asn Arg Ile Cys
                35                  40                  45

Pro Ile Leu Met Glu Lys Leu Asn Arg Asn Ser Arg Arg Gly Ile Thr
        50                  55                  60

Tyr Asn Tyr Val Ile Ser Ser Arg Leu Gly Arg Asn Thr Tyr Lys Glu
65                  70                  75                  80

Gln Tyr Ala Phe Leu Tyr Lys Glu Lys Leu Val Ser Val Lys Arg Ser
                85                  90                  95

Tyr His Tyr His Asp Tyr Gln Asp Gly Asp Ala Asp Val Phe Ser Arg
            100                 105                 110
```

```
Glu Pro Phe Val Val Trp Phe Gln Ser Pro His Thr Ala Val Lys Asp
            115                 120                 125

Phe Val Ile Ile Pro Leu His Thr Thr Pro Glu Thr Ser Val Lys Glu
130                 135                 140

Ile Asp Glu Leu Val Glu Val Tyr Thr Asp Val Lys His Arg Trp Lys
145                 150                 155                 160

Ala Glu Asn Phe Ile Phe Met Gly Asp Phe Asn Ala Gly Cys Ser Tyr
                165                 170                 175

Val Pro Lys Lys Ala Trp Lys Asn Ile Arg Leu Arg Thr Asp Pro Arg
            180                 185                 190

Phe Val Trp Leu Ile Gly Asp Gln Glu Asp Thr Thr Val Lys Lys Ser
            195                 200                 205

Thr Asn Cys Ala Tyr Asp Arg Ile Val Leu Arg Gly Gln Glu Ile Val
        210                 215                 220

Ser Ser Val Val Pro Lys Ser Asn Ser Val Phe Asp Phe Gln Lys Ala
225                 230                 235                 240

Tyr Lys Leu Thr Glu Glu Glu Ala Leu Asp Val Ser Asp His Phe Pro
                245                 250                 255

Val Glu Phe Lys Leu Gln Ser Ser Arg Ala Phe Thr Asn Ser Lys Lys
            260                 265                 270

Ser Val Thr Leu Arg Lys Lys Thr Lys Ser Lys Arg Ser
            275                 280                 285
```

<210> SEQ ID NO 47
<211> LENGTH: 369
<212> TYPE: PRT
<213> ORGANISM: Homo sapiens
<220> FEATURE:
<221> NAME/KEY: misc_feature
<222> LOCATION: (1)..(369)
<223> OTHER INFORMATION: Human Trex1

<400> SEQUENCE: 47

```
Met Gly Pro Gly Ala Arg Arg Gln Gly Arg Ile Val Gln Gly Arg Pro
1               5                   10                  15

Glu Met Cys Phe Cys Pro Pro Thr Pro Leu Pro Pro Leu Arg Ile
            20                  25                  30

Leu Thr Leu Gly Thr His Thr Pro Thr Pro Cys Ser Ser Pro Gly Ser
            35                  40                  45

Ala Ala Gly Thr Tyr Pro Thr Met Gly Ser Gln Ala Leu Pro Pro Gly
        50                  55                  60

Pro Met Gln Thr Leu Ile Phe Phe Asp Met Glu Ala Thr Gly Leu Pro
65                  70                  75                  80

Phe Ser Gln Pro Lys Val Thr Glu Leu Cys Leu Leu Ala Val His Arg
                85                  90                  95

Cys Ala Leu Glu Ser Pro Pro Thr Ser Gln Gly Pro Pro Pro Thr Val
            100                 105                 110

Pro Pro Pro Pro Arg Val Val Asp Lys Leu Ser Leu Cys Val Ala Pro
            115                 120                 125

Gly Lys Ala Cys Ser Pro Ala Ala Ser Glu Ile Thr Gly Leu Ser Thr
        130                 135                 140

Ala Val Leu Ala Ala His Gly Arg Gln Cys Phe Asp Asp Asn Leu Ala
145                 150                 155                 160

Asn Leu Leu Leu Ala Phe Leu Arg Arg Gln Pro Gln Pro Trp Cys Leu
                165                 170                 175

Val Ala His Asn Gly Asp Arg Tyr Asp Phe Pro Leu Leu Gln Ala Glu
```

-continued

```
                    180                 185                 190
Leu Ala Met Leu Gly Leu Thr Ser Ala Leu Asp Gly Ala Phe Cys Val
                195                 200                 205
Asp Ser Ile Thr Ala Leu Lys Ala Leu Glu Arg Ala Ser Ser Pro Ser
            210                 215                 220
Glu His Gly Pro Arg Lys Ser Tyr Ser Leu Gly Ser Ile Tyr Thr Arg
225                 230                 235                 240
Leu Tyr Gly Gln Ser Pro Pro Asp Ser His Thr Ala Glu Gly Asp Val
                245                 250                 255
Leu Ala Leu Leu Ser Ile Cys Gln Trp Arg Pro Gln Ala Leu Leu Arg
            260                 265                 270
Trp Val Asp Ala His Ala Arg Pro Phe Gly Thr Ile Arg Pro Met Tyr
        275                 280                 285
Gly Val Thr Ala Ser Ala Arg Thr Lys Pro Arg Pro Ser Ala Val Thr
    290                 295                 300
Thr Thr Ala His Leu Ala Thr Thr Arg Asn Thr Ser Pro Ser Leu Gly
305                 310                 315                 320
Glu Ser Arg Gly Thr Lys Asp Leu Pro Pro Val Lys Asp Pro Gly Ala
                325                 330                 335
Leu Ser Arg Glu Gly Leu Leu Ala Pro Leu Gly Leu Leu Ala Ile Leu
            340                 345                 350
Thr Leu Ala Val Ala Thr Leu Tyr Gly Leu Ser Leu Ala Thr Pro Gly
        355                 360                 365
Glu
```

<210> SEQ ID NO 48
<211> LENGTH: 360
<212> TYPE: PRT
<213> ORGANISM: Homo sapiens
<220> FEATURE:
<221> NAME/KEY: misc_feature
<222> LOCATION: (1)..(360)
<223> OTHER INFORMATION: Human DNase2 alpha (NP_001366.1)

<400> SEQUENCE: 48

```
Met Ile Pro Leu Leu Ala Ala Leu Leu Cys Val Pro Ala Gly Ala
1               5                   10                  15
Leu Thr Cys Tyr Gly Asp Ser Gly Gln Pro Val Asp Trp Phe Val Val
                20                  25                  30
Tyr Lys Leu Pro Ala Leu Arg Gly Ser Gly Glu Ala Ala Gln Arg Gly
            35                  40                  45
Leu Gln Tyr Lys Tyr Leu Asp Glu Ser Ser Gly Gly Trp Arg Asp Gly
        50                  55                  60
Arg Ala Leu Ile Asn Ser Pro Glu Gly Ala Val Gly Arg Ser Leu Gln
65                  70                  75                  80
Pro Leu Tyr Arg Ser Asn Thr Ser Gln Leu Ala Phe Leu Leu Tyr Asn
                85                  90                  95
Asp Gln Pro Pro Gln Pro Ser Lys Ala Gln Asp Ser Ser Met Arg Gly
            100                 105                 110
His Thr Lys Gly Val Leu Leu Leu Asp His Asp Gly Gly Phe Trp Leu
        115                 120                 125
Val His Ser Val Pro Asn Phe Pro Pro Ala Ser Ser Ala Ala Tyr
    130                 135                 140
Ser Trp Pro His Ser Ala Cys Thr Tyr Gly Gln Thr Leu Leu Cys Val
145                 150                 155                 160
```

```
Ser Phe Pro Phe Ala Gln Phe Ser Lys Met Gly Lys Gln Leu Thr Tyr
                165                 170                 175

Thr Tyr Pro Trp Val Tyr Asn Tyr Gln Leu Glu Gly Ile Phe Ala Gln
            180                 185                 190

Glu Phe Pro Asp Leu Glu Asn Val Val Lys Gly His His Val Ser Gln
            195                 200                 205

Glu Pro Trp Asn Ser Ser Ile Thr Leu Thr Ser Gln Ala Gly Ala Val
        210                 215                 220

Phe Gln Ser Phe Ala Lys Phe Ser Lys Phe Gly Asp Asp Leu Tyr Ser
225                 230                 235                 240

Gly Trp Leu Ala Ala Leu Gly Thr Asn Leu Gln Val Gln Phe Trp
                245                 250                 255

His Lys Thr Val Gly Ile Leu Pro Ser Asn Cys Ser Asp Ile Trp Gln
                260                 265                 270

Val Leu Asn Val Asn Gln Ile Ala Phe Pro Gly Pro Ala Gly Pro Ser
            275                 280                 285

Phe Asn Ser Thr Glu Asp His Ser Lys Trp Cys Val Ser Pro Lys Gly
        290                 295                 300

Pro Trp Thr Cys Val Gly Asp Met Asn Arg Asn Gln Gly Glu Glu Gln
305                 310                 315                 320

Arg Gly Gly Gly Thr Leu Cys Ala Gln Leu Pro Ala Leu Trp Lys Ala
                325                 330                 335

Phe Gln Pro Leu Val Lys Asn Tyr Gln Pro Cys Asn Gly Met Ala Arg
                340                 345                 350

Lys Pro Ser Arg Ala Tyr Lys Ile
            355                 360

<210> SEQ ID NO 49
<211> LENGTH: 361
<212> TYPE: PRT
<213> ORGANISM: Homo sapiens
<220> FEATURE:
<221> NAME/KEY: misc_feature
<222> LOCATION: (1)..(361)
<223> OTHER INFORMATION: human DNase2 beta

<400> SEQUENCE: 49

Met Lys Gln Lys Met Met Ala Arg Leu Leu Arg Thr Ser Phe Ala Leu
1               5                   10                  15

Leu Phe Leu Gly Leu Phe Gly Val Leu Gly Ala Ala Thr Ile Ser Cys
            20                  25                  30

Arg Asn Glu Glu Gly Lys Ala Val Asp Trp Phe Thr Phe Tyr Lys Leu
        35                  40                  45

Pro Lys Arg Gln Asn Lys Glu Ser Gly Glu Thr Gly Leu Glu Tyr Leu
    50                  55                  60

Tyr Leu Asp Ser Thr Thr Arg Ser Trp Arg Lys Ser Glu Gln Leu Met
65                  70                  75                  80

Asn Asp Thr Lys Ser Val Leu Gly Arg Thr Leu Gln Gln Leu Tyr Glu
                85                  90                  95

Ala Tyr Ala Ser Lys Ser Asn Asn Thr Ala Tyr Leu Ile Tyr Asn Asp
            100                 105                 110

Gly Val Pro Lys Pro Val Asn Tyr Ser Arg Lys Tyr Gly His Thr Lys
        115                 120                 125

Gly Leu Leu Leu Trp Asn Arg Val Gln Gly Phe Trp Leu Ile His Ser
    130                 135                 140

Ile Pro Gln Phe Pro Pro Ile Pro Glu Glu Gly Tyr Asp Tyr Pro Pro
```

```
                145                 150                 155                 160
        Thr Gly Arg Arg Asn Gly Gln Ser Gly Ile Cys Ile Thr Phe Lys Tyr
                        165                 170                 175

Asn Gln Tyr Glu Ala Ile Asp Ser Gln Leu Leu Val Cys Asn Pro Asn
                        180                 185                 190

Val Tyr Ser Cys Ser Ile Pro Ala Thr Phe His Gln Glu Leu Ile His
                        195                 200                 205

Met Pro Gln Leu Cys Thr Arg Ala Ser Ser Glu Ile Pro Gly Arg
                210                 215                 220

Leu Leu Thr Thr Leu Gln Ser Ala Gln Gly Gln Lys Phe Leu His Phe
        225                 230                 235                 240

Ala Lys Ser Asp Ser Phe Leu Asp Asp Ile Phe Ala Ala Trp Met Ala
                        245                 250                 255

Gln Arg Leu Lys Thr His Leu Leu Thr Glu Thr Trp Gln Arg Lys Arg
                        260                 265                 270

Gln Glu Leu Pro Ser Asn Cys Ser Leu Pro Tyr His Val Tyr Asn Ile
                        275                 280                 285

Lys Ala Ile Lys Leu Ser Arg His Ser Tyr Phe Ser Ser Tyr Gln Asp
                        290                 295                 300

His Ala Lys Trp Cys Ile Ser Gln Lys Gly Thr Lys Asn Arg Trp Thr
        305                 310                 315                 320

Cys Ile Gly Asp Leu Asn Arg Ser Pro His Gln Ala Phe Arg Ser Gly
                        325                 330                 335

Gly Phe Ile Cys Thr Gln Asn Trp Gln Ile Tyr Gln Ala Phe Gln Gly
                        340                 345                 350

Leu Val Leu Tyr Tyr Glu Ser Cys Lys
                        355                 360

<210> SEQ ID NO 50
<211> LENGTH: 232
<212> TYPE: PRT
<213> ORGANISM: Artificial Sequence
<220> FEATURE:
<223> OTHER INFORMATION: Synthetic: Fc region N83S

<400> SEQUENCE: 50

Glu Pro Lys Ser Cys Asp Lys Thr His Thr Cys Pro Pro Cys Pro Ala
        1               5                   10                  15

Pro Glu Leu Leu Gly Gly Pro Ser Val Phe Leu Phe Pro Pro Lys Pro
                        20                  25                  30

Lys Asp Thr Leu Met Ile Ser Arg Thr Pro Glu Val Thr Cys Val Val
                        35                  40                  45

Val Asp Val Ser His Glu Asp Pro Glu Val Lys Phe Asn Trp Tyr Val
                50                  55                  60

Asp Gly Val Glu Val His Asn Ala Lys Thr Lys Pro Arg Glu Glu Gln
        65                  70                  75                  80

Tyr Ser Ser Thr Tyr Arg Val Val Ser Val Leu Thr Val Leu His Gln
                        85                  90                  95

Asp Trp Leu Asn Gly Lys Glu Tyr Lys Cys Lys Val Ser Asn Lys Ala
                        100                 105                 110

Leu Pro Ala Pro Ile Glu Lys Thr Ile Ser Lys Ala Lys Gly Gln Pro
                        115                 120                 125

Arg Glu Pro Gln Val Tyr Thr Leu Pro Pro Ser Arg Asp Glu Leu Thr
                        130                 135                 140

Lys Asn Gln Val Ser Leu Thr Cys Leu Val Lys Gly Phe Tyr Pro Ser
```

```
                145                 150                 155                 160
Asp Ile Ala Val Glu Trp Glu Ser Asn Gly Gln Pro Glu Asn Asn Tyr
                    165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 51
<211> LENGTH: 232
<212> TYPE: PRT
<213> ORGANISM: Artificial Sequence
<220> FEATURE:
<223> OTHER INFORMATION: Synthetic: Fc region with SCC

<400> SEQUENCE: 51

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                    165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 52
<211> LENGTH: 232
<212> TYPE: PRT
<213> ORGANISM: Artificial Sequence
<220> FEATURE:
<223> OTHER INFORMATION: Synthetic: Fc region with SSS
```

<400> SEQUENCE: 52

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 53
<211> LENGTH: 50
<212> TYPE: PRT
<213> ORGANISM: Artificial Sequence
<220> FEATURE:
<223> OTHER INFORMATION: Synthetic: Linker

<400> SEQUENCE: 53

Leu Glu Ala Glu Ala Ala Ala Lys Glu Ala Ala Lys Glu Ala Ala
1               5                   10                  15

Ala Lys Glu Ala Ala Lys Ala Leu Glu Ala Glu Ala Ala Ala Lys
                20                  25                  30

Glu Ala Ala Ala Lys Glu Ala Ala Ala Lys Ala Ala Ala Lys Ala
            35                  40                  45

Leu Glu
    50

<210> SEQ ID NO 54
<211> LENGTH: 20
<212> TYPE: PRT
<213> ORGANISM: Artificial Sequence
<220> FEATURE:
<223> OTHER INFORMATION: Synthetic: VK3LP leader

<400> SEQUENCE: 54

Met Glu Thr Pro Ala Gln Leu Leu Phe Leu Leu Leu Trp Leu Pro
1               5                   10                  15

Asp Thr Thr Gly
            20

<210> SEQ ID NO 55
<211> LENGTH: 232
<212> TYPE: PRT
<213> ORGANISM: Artificial Sequence
<220> FEATURE:
<223> OTHER INFORMATION: Synthetic: Fc region with SCC, P238S, P331S
      mutations

<400> SEQUENCE: 55

Glu Pro Lys Ser Ser Asp Lys Thr His Thr Ser Pro Pro Ser Pro Ala
1               5                   10                  15

Pro Glu Leu Leu Gly Gly Ser Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 56
<211> LENGTH: 232
<212> TYPE: PRT
<213> ORGANISM: Artificial Sequence
<220> FEATURE:
<223> OTHER INFORMATION: Synthetic: Fc region with P238S, P331S
      mutations

<400> SEQUENCE: 56

Glu Pro Lys Cys Ser Asp Lys Thr His Thr Ser Pro Pro Ser Pro Ala
1               5                   10                  15

Pro Glu Leu Leu Gly Gly Ser Ser Val Phe Leu Phe Pro Pro Lys Pro
                20                  25                  30

```
Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 57
<211> LENGTH: 1023
<212> TYPE: PRT
<213> ORGANISM: Artificial Sequence
<220> FEATURE:
<223> OTHER INFORMATION: Synthetic: RSLV-327(RNase-linker-HSA-linker-
      DNase E13R/N74K/A114F/ T205K)

<400> SEQUENCE: 57

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
            35                  40                  45

Met Met Arg Arg Arg Asn Met Thr Gln Gly Arg Cys Lys Pro Val Asn
 50                  55                  60

Thr Phe Val His Glu Pro Leu Val Asp Val Gln Asn Val Cys Phe Gln
 65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
            115                 120                 125

Ala Cys Glu Gly Ser Pro Tyr Val Pro Val His Phe Asp Ala Ser Val
            130                 135                 140

Glu Asp Ser Thr Gly Gly Gly Gly Ser Gly Gly Gly Gly Ser Gly Gly
```

```
                145                 150                 155                 160
Gly Gly Ser Asp Ala His Lys Ser Glu Val Ala His Arg Phe Lys Asp
                    165                 170                 175

Leu Gly Glu Glu Asn Phe Lys Ala Leu Val Leu Ile Ala Phe Ala Gln
                    180                 185                 190

Tyr Leu Gln Gln Cys Pro Phe Glu Asp His Val Lys Leu Val Asn Glu
                    195                 200                 205

Val Thr Glu Phe Ala Lys Thr Cys Val Ala Asp Glu Ser Ala Glu Asn
        210                 215                 220

Cys Asp Lys Ser Leu His Thr Leu Phe Gly Asp Lys Leu Cys Thr Val
225                 230                 235                 240

Ala Thr Leu Arg Glu Thr Tyr Gly Glu Met Ala Asp Cys Cys Ala Lys
                    245                 250                 255

Gln Glu Pro Glu Arg Asn Glu Cys Phe Leu Gln His Lys Asp Asp Asn
                    260                 265                 270

Pro Asn Leu Pro Arg Leu Val Arg Pro Glu Val Asp Val Met Cys Thr
                    275                 280                 285

Ala Phe His Asp Asn Glu Glu Thr Phe Leu Lys Lys Tyr Leu Tyr Glu
        290                 295                 300

Ile Ala Arg Arg His Pro Tyr Phe Tyr Ala Pro Glu Leu Leu Phe Phe
305                 310                 315                 320

Ala Lys Arg Tyr Lys Ala Ala Phe Thr Glu Cys Cys Gln Ala Ala Asp
                    325                 330                 335

Lys Ala Ala Cys Leu Leu Pro Lys Leu Asp Glu Leu Arg Asp Glu Gly
                    340                 345                 350

Lys Ala Ser Ser Ala Lys Gln Arg Leu Lys Cys Ala Ser Leu Gln Lys
                    355                 360                 365

Phe Gly Glu Arg Ala Phe Lys Ala Trp Ala Val Ala Arg Leu Ser Gln
        370                 375                 380

Arg Phe Pro Lys Ala Glu Phe Ala Glu Val Ser Lys Leu Val Thr Asp
385                 390                 395                 400

Leu Thr Lys Val His Thr Glu Cys Cys His Gly Asp Leu Leu Glu Cys
                    405                 410                 415

Ala Asp Asp Arg Ala Asp Leu Ala Lys Tyr Ile Cys Glu Asn Gln Asp
                    420                 425                 430

Ser Ile Ser Ser Lys Leu Lys Glu Cys Cys Glu Lys Pro Leu Leu Glu
                    435                 440                 445

Lys Ser His Cys Ile Ala Glu Val Glu Asn Asp Glu Met Pro Ala Asp
        450                 455                 460

Leu Pro Ser Leu Ala Ala Asp Phe Val Glu Ser Lys Asp Val Cys Lys
465                 470                 475                 480

Asn Tyr Ala Glu Ala Lys Asp Val Phe Leu Gly Met Phe Leu Tyr Glu
                    485                 490                 495

Tyr Ala Arg Arg His Pro Asp Tyr Ser Val Val Leu Leu Leu Arg Leu
                    500                 505                 510

Ala Lys Thr Tyr Glu Thr Thr Leu Glu Lys Cys Cys Ala Ala Ala Asp
        515                 520                 525

Pro His Glu Cys Tyr Ala Lys Val Phe Asp Glu Phe Lys Pro Leu Val
        530                 535                 540

Glu Glu Pro Gln Asn Leu Ile Lys Gln Asn Cys Glu Leu Phe Glu Gln
545                 550                 555                 560

Leu Gly Glu Tyr Lys Phe Gln Asn Ala Leu Leu Val Arg Tyr Thr Lys
                    565                 570                 575
```

```
Lys Val Pro Gln Val Ser Thr Pro Thr Leu Val Glu Val Ser Arg Asn
            580                 585                 590

Leu Gly Lys Val Gly Ser Lys Cys Lys His Pro Glu Ala Lys Arg
        595                 600                 605

Met Pro Cys Ala Glu Asp Tyr Leu Ser Val Val Leu Asn Gln Leu Cys
            610                 615                 620

Val Leu His Glu Lys Thr Pro Val Ser Asp Arg Val Thr Lys Cys Cys
625                 630                 635                 640

Thr Glu Ser Leu Val Asn Arg Arg Pro Cys Phe Ser Ala Leu Glu Val
                645                 650                 655

Asp Glu Thr Tyr Val Pro Lys Glu Phe Asn Ala Glu Thr Phe Thr Phe
            660                 665                 670

His Ala Asp Ile Cys Thr Leu Ser Glu Lys Glu Arg Gln Ile Lys Lys
            675                 680                 685

Gln Thr Ala Leu Val Glu Leu Val Lys His Lys Pro Lys Ala Thr Lys
            690                 695                 700

Glu Gln Leu Lys Ala Val Met Asp Asp Phe Ala Ala Phe Val Glu Lys
705                 710                 715                 720

Cys Cys Lys Ala Asp Asp Lys Glu Thr Cys Phe Ala Glu Glu Gly Lys
                725                 730                 735

Lys Leu Val Ala Ala Ser Gln Ala Ala Leu Gly Leu Gly Gly Gly Gly
            740                 745                 750

Ser Gly Gly Gly Gly Ser Gly Gly Gly Gly Ser Leu Lys Ile Ala Ala
        755                 760                 765

Phe Asn Ile Gln Thr Phe Gly Arg Thr Lys Met Ser Asn Ala Thr Leu
            770                 775                 780

Val Ser Tyr Ile Val Gln Ile Leu Ser Arg Tyr Asp Ile Ala Leu Val
785                 790                 795                 800

Gln Glu Val Arg Asp Ser His Leu Thr Ala Val Gly Lys Leu Leu Asp
                805                 810                 815

Asn Leu Asn Gln Asp Ala Pro Asp Thr Tyr His Tyr Val Val Ser Glu
            820                 825                 830

Pro Leu Gly Arg Lys Ser Tyr Lys Glu Arg Tyr Leu Phe Val Tyr Arg
            835                 840                 845

Pro Asp Gln Val Ser Ala Val Asp Ser Tyr Tyr Tyr Asp Asp Gly Cys
850                 855                 860

Glu Pro Cys Gly Asn Asp Thr Phe Asn Arg Glu Pro Phe Ile Val Arg
865                 870                 875                 880

Phe Phe Ser Arg Phe Thr Glu Val Arg Glu Phe Ala Ile Val Pro Leu
                885                 890                 895

His Ala Ala Pro Gly Asp Ala Val Ala Glu Ile Asp Ala Leu Tyr Asp
            900                 905                 910

Val Tyr Leu Asp Val Gln Glu Lys Trp Gly Leu Glu Asp Val Met Leu
            915                 920                 925

Met Gly Asp Phe Asn Ala Gly Cys Ser Tyr Val Arg Pro Ser Gln Trp
        930                 935                 940

Ser Ser Ile Arg Leu Trp Thr Ser Pro Thr Phe Gln Trp Leu Ile Pro
945                 950                 955                 960

Asp Ser Ala Asp Thr Thr Ala Lys Pro Thr His Cys Ala Tyr Asp Arg
                965                 970                 975

Ile Val Val Ala Gly Met Leu Leu Arg Gly Ala Val Val Pro Asp Ser
            980                 985                 990
```

-continued

Ala Leu Pro Phe Asn Phe Gln Ala Ala Tyr Gly Leu Ser Asp Gln Leu
            995                 1000                1005

Ala Gln Ala Ile Ser Asp His Tyr Pro Val Glu Val Met Leu Lys
        1010                1015                1020

<210> SEQ ID NO 58
<211> LENGTH: 50
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(50)
<223> OTHER INFORMATION: "Gly Gly Gly Gly Ser" is present at least once
      but can repeat up to ten or more times

<400> SEQUENCE: 58

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 59
<211> LENGTH: 50
<212> TYPE: PRT
<213> ORGANISM: Artificial Sequence
<220> FEATURE:
<223> OTHER INFORMATION: Synthetic: linker

<400> SEQUENCE: 59

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 60
<211> LENGTH: 51
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (2)..(51)
<223> OTHER INFORMATION: "Gly Gly Gly Gly Ser" is present at least once
      but can repeat up to ten or more times

<400> SEQUENCE: 60

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser
    50

<210> SEQ ID NO 61
<211> LENGTH: 51
<212> TYPE: PRT
<213> ORGANISM: Artificial Sequence
<220> FEATURE:
<223> OTHER INFORMATION: Synthetic: linker

<400> SEQUENCE: 61

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser
    50

<210> SEQ ID NO 62
<211> LENGTH: 25
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(25)
<223> OTHER INFORMATION: "Gly Gly Gly Gly Ser" is present at least once
      but can repeat up to five times

<400> SEQUENCE: 62

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 63
<211> LENGTH: 20
<212> TYPE: PRT
<213> ORGANISM: Artificial Sequence
<220> FEATURE:
<223> OTHER INFORMATION: Synthetic: linker

<400> SEQUENCE: 63

Gly Gly Gly Gly Ser Gly Gly Gly Gly Ser Gly Gly Gly Gly Ser Gly
1               5                   10                  15

Gly Gly Gly Ser
            20

<210> SEQ ID NO 64
<211> LENGTH: 25
<212> TYPE: PRT
<213> ORGANISM: Artificial Sequence
<220> FEATURE:
<223> OTHER INFORMATION: Synthetic: linker

<400> SEQUENCE: 64

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

```
<210> SEQ ID NO 65
<211> LENGTH: 27
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (2)..(26)
<223> OTHER INFORMATION: "Glu Ala Ala Ala Lys" repeats at least two
      times and up to five times

<400> SEQUENCE: 65

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 66
<211> LENGTH: 10
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(10)
<223> OTHER INFORMATION: "Gly Ser" is present at least once and can
      repeat up to five times

<400> SEQUENCE: 66

Gly Ser Gly Ser Gly Ser Gly Ser Gly Ser
1               5                   10

<210> SEQ ID NO 67
<211> LENGTH: 20
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(20)
<223> OTHER INFORMATION: "Gly Gly Ser Gly" is present at least once and
      can repeat up to five times

<400> SEQUENCE: 67

Gly Gly Ser Gly Gly Gly Ser Gly Gly Gly Ser Gly Gly Gly Ser Gly
1               5                   10                  15

Gly Gly Ser Gly
            20

<210> SEQ ID NO 68
<211> LENGTH: 30
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(30)
<223> OTHER INFORMATION: "Gly Gly Ser Gly Gly Ser" is present at least
      once and can repeat up to five times

<400> SEQUENCE: 68

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30
```

```
<210> SEQ ID NO 69

<400> SEQUENCE: 69

000

<210> SEQ ID NO 70
<211> LENGTH: 4
<212> TYPE: PRT
<213> ORGANISM: Artificial Sequence
<220> FEATURE:
<223> OTHER INFORMATION: Synthetic: linker

<400> SEQUENCE: 70

Gly Gly Ser Gly
1
```